(12) United States Patent
Krieg et al.

(10) Patent No.: US 10,907,161 B2
(45) Date of Patent: Feb. 2, 2021

(54) SYNTHETIC RIG-I-LIKE RECEPTOR AGONISTS

(71) Applicant: Checkmate Pharmaceuticals, Inc., Cambridge, MA (US)

(72) Inventors: Arthur M. Krieg, Cambridge, MA (US); Aaron Jay Morris, Brighton, MA (US)

(73) Assignee: Checkmate Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 16/389,432

(22) Filed: Apr. 19, 2019

(65) Prior Publication Data

US 2020/0063141 A1 Feb. 27, 2020

Related U.S. Application Data

(60) Provisional application No. 62/659,999, filed on Apr. 19, 2018.

(51) Int. Cl.
*C12N 15/113* (2010.01)

(52) U.S. Cl.
CPC .... *C12N 15/1138* (2013.01); *C12N 2310/331* (2013.01); *C12N 2310/531* (2013.01)

(58) Field of Classification Search
None
See application file for complete search history.

(56) References Cited

U.S. PATENT DOCUMENTS

| | | | |
|---|---|---|---|
| 9,381,208 | B2 | 7/2016 | Hartmann et al. |
| 2011/0184045 | A1 | 7/2011 | Hartmann |
| 2012/0107272 | A1 | 5/2012 | Manoharan et al. |
| 2015/0017207 | A1 | 1/2015 | Gale, Jr. et al. |
| 2019/0184006 | A1 * | 6/2019 | Chan ............. A61K 39/145 |

FOREIGN PATENT DOCUMENTS

| | | |
|---|---|---|
| WO | 2006/063252 A2 | 6/2006 |
| WO | 2008/017473 A2 | 2/2008 |
| WO | 2009/095226 A2 | 8/2009 |
| WO | 2009/141146 A1 | 11/2009 |
| WO | 2012/130886 A1 | 10/2012 |
| WO | 2013/064584 A1 | 5/2013 |
| WO | 2013/097965 A1 | 7/2013 |
| WO | 2014/049079 A1 | 4/2014 |
| WO | 2014/124433 A1 | 8/2014 |
| WO | WO-2014159990 A1 * | 10/2014 ......... A61K 2300/00 |
| WO | 2015/091578 A1 | 6/2015 |
| WO | 2015/144736 A1 | 10/2015 |
| WO | 2016/011324 A2 | 1/2016 |
| WO | 2017/121494 A1 | 7/2017 |
| WO | 2017/173427 A1 | 10/2017 |
| WO | 2017/185180 A1 | 11/2017 |
| WO | WO-2019126240 A1 * | 6/2019 ............. A61K 47/64 |
| WO | WO-2019246450 A1 * | 12/2019 ............. A61K 45/06 |

OTHER PUBLICATIONS

Linehan et al. Supplementary Materials for A Minimal RNA ligand for potent RIG-I acticiation in living mice, Sci Adv. 4, e1701854 pp. 1-7 (Year: 2018).*
Liao et al. Plos One 6, e26463, pp. 1-14 (Year: 2011).*
Akke, M. et al., "Base Dynamics in a UUCG tetraloop RNA hairpin Characterized by 15N spin relaxation: Correlations with structure and stability," RNA, vol. 3:702-709 (1997).
Chiang, C. et al., "Sequence-specific modifications enhance the broad-spectrum antiviral response activated by RIG-I agonists," Journal of Virology, vol. 89(15):8011-8025 (2015).
Cui, S. et al., The C-Terminal Regulatory Domain Is the RNA 5'-Triphosphate Sensor of RIG-I, Molecular Cell, vol. 29:169-179 (2008).
Fitzgerald, M. et al., "Selective RNA targeting and regulated signaling by RIG-I is controlled by coordination of RNA and ATP binding," Nucleic Acids Research, vol. 45(3): 1442-1454 (2016).
Goubau, D. et al., "Antiviral immunity via RIG-I-mediated recognition of RNA bearing 5'-diphosphates," Nature, vol. 514(7522): 372-375 (2014).
Goulet, M. et al., "Systems analysis of a RIG-I agonist inducing broad spectrum inhibition of virus infectivity", PLOS Pathogens, vol. 9(4):p. e1003298: 25 pages (2013).
Hornung, V. et al., "5-Triphosphate RNA Is the Ligand for RIG-I," Science, vol. 314(10):994-997 (2006).
International Search Report and Written Opinion, PCT/US2019/028343, dated Aug. 19, 2019, 22 pages.
Jagath, J. et al., "Important role of the tetraloop region of 4.5S RNA in SRP binding to its receptor FtsY," RNA, vol. 7:293-301 (2001).
Jiang, F. et al., "Structural Basis of RNA Recognition and Activation by Innate Immune Receptor RIG-I," Nature. ; 479(7373): 423-427 (2012).
Kiliszek, A. et al., "Stabilization of RNA hairpins using non-nucleotide linkers and circularization," Nucleic Acids Research, vol. 45(10): e92 (2019).
Kim, I. et al., "Specific Recognition of HIV TAR RNA by the dsRNA Binding Domains (dsRBD1-dsRBD2) of PKR," J. Mol. Biol., vol. 358: 430-442 (2006).
Kohlway, A. et al., "Defining the Functional Determinants for RNA surveillance by RIG-I," EMBO Reports, vol. 14: 772-779 (2013).
Kowalinski, E. et al., "Structural Basis for the Activation of Innate Immune Pattern-Recognition Receptor RIG-I by Viral RNA," Cell, vol. 147: 423-435 (2011).
Linehan, M. et al., "A minimal RNA ligand for potent RIG-I activation in living mice," Sci. Adv., vol. 4: e1701854, 10 pages (2018).
Liu, G. et al., "Influenza A Virus panhandle structure is directly involved in RIG-I activation and Interferon induction", Journal of Virology, vol. 89(11):6067-6079 (2015).
Lu, C. et al., "The Structural Basis of 5' Triphosphate Double-Stranded RNA Recognition by RIG-I C-Terminal Domain," Structure, vol. 18: 1032-1043 (2010).

(Continued)

*Primary Examiner* — Brian Whiteman
(74) *Attorney, Agent, or Firm* — Nelson Mullins Riley & Scarborough LLP; Amy E. Mandragouras, Esq.

(57) ABSTRACT

The present disclosure relates to, inter alia, RNA molecules (e.g., RNA hairpin agonists) that bind to and agonize RIG-I-like receptors (RLRs), and to use of the molecules in methods for treating, or ameliorating one or more symptoms of, a disorder (e.g., cancer).

33 Claims, 1 Drawing Sheet
(1 of 1 Drawing Sheet(s) Filed in Color)

Specification includes a Sequence Listing.

(56) References Cited

OTHER PUBLICATIONS

Luo, D. et al., "Structural Insights into RNA Recognition by RIG-I," Cell, vol. 147: 409-422 (2011).

Luo, D. et al., "Visualizing the Determinants of Viral RNA Recognition by Innate Immune Sensor RIG-I," Structure, vol. 20 (Issue 11):1983-1988 (2012).

Luo, D. et al., "Visualizing the Determinants of Viral RNA Recognition by Innate Immune Sensor RIG-I," Supplemental Data. Structure, vol. 20 (Issue 11):10 pages (2012).

Marques, J.T. et al., "A structural basis for discriminating between self and nonself double-stranded RNAs in mammalian cells," Nature Biotechnology, vol. 24 (5):559-565 (2006).

Pichlmair, A. et al., "RIG-I-Mediated Antiviral Responses to Single-Stranded RNA Bearing 5' Phosphates," Science, vol. 314: 997-1001 (2006).

Ramos, A. et al., "RNA recognition by a Staufen double-stranded RNA-binding domain," The EMBO Journal, vol. 19(5):997-1009 (2000).

Ranoa, D. et al., "Cancer therapies activate RIG-I-like receptor pathway through endogenous non-coding RNAs," Oncotarget, vol. 7 (18):26496-26515 (2016).

Rawling, D. et al., "Establishing the role of ATP for the function of the RIG-I innate immune sensor," eLife, vol. 4: e09391, 21 pages (2015).

Schlee, M. et al., "The Chase for the RIG-I Ligand-Recent Advances," The American Society of Gene & Cell Therapy, vol. 18 (7):1254-1262 (2010).

Schlee, M., "Master sensors of pathogenic RNA—RIG-I like receptors," Immunobiology vol. 218: 1322-1335 (2013).

Schlee, M., et al., "Discriminating self from non-self in Nucleic acid sensing," Nat Rev Immunol., vol. 16:566-580 (2016).

Schlee, M., et al., "Approaching the RNA ligand for RIG-I?" Immunological Reviews, vol. 227: 66-74 (2009).

Schlee, M., et al., "Recognition of 5' Triphosphate by RIG-I Helicase Requires Short Blunt Double-Stranded RNA as Contained in Panhandle of Negative-Strand Virus," Immunity, vol. 31: 25-34 (2009).

Schmidt, A. et al., "5' triphosphate RNA requires base-paired structures to activate antiviral signaling via RIG-I," PNAS, vol. 106 (29):12067-12072 (2009).

Wang, Y. et al., "Structural and functional insights into pattern recognition by the innate immune receptor RIG-I," Nat Struct Mol Biol., vol. 17(7): 781-787 (2010).

Baek, Y-M, et al., "Dependence of RIG-I Nucleic Acid-Binding and ATP Hydrolysis on Activation of Type I Interferon Response," Immune Netw., vol. 16(4):249-255 (2016).

Besch, R. et al., "Proapoptotic signaling induced by RIG-I and MDA-5 results in type I interferon-independent apoptosis in human melanoma cells," J Clin Invest., vol. 119:2399-2411 (2009).

Civril, F. et al., "The RIG-I ATPase domain structure reveals insights into ATP-dependent antiviral signaling," EMBO Reports, vol. 12:1127-1134 (2011).

Ellermeier, J. et al., "Therapeutic efficacy of bifunctional siRNA combining TGF-β1 silencing with RIG-I activation in pancreatic cancer," Cancer Res., vol. 73(6):1709-1720 (2013).

Hwang, S-Y., et al., "5'-Triphosphate-RNA-independent activation of RIG-I via RNA aptamer with enhanced antiviral activity," Nucleic Acids Res., vol. 40(6):2724-2733 (2012).

Kato, H. et al., "Differential roles of MDA5 and RIG-I helicases in the recognition of RNA viruses," Nature, vol. 441:101-105 (2006).

Kell, A. et al., "RIG-I in RNA virus recognition," Virology, vol. 479-480:110-121 (2015).

Lee, M-K, et al., "Structural features of influenza A virus panhandle RNA enabling the activation of RIG-I independently of 5'-triphosphate," Nucleic Acids Res., vol. 44(17):8407-8416 (2016).

Loo, Y-M. et al., "Distinct RIG-I and MDA5 signaling by RNA viruses in innate immunity," J Virol., vol. 82:335-345 (2008).

Peisley, A. et al., "Multi-level regulation of cellular recognition of viral dsRNA," Cell Mol Life Sci, vol. 70(11):1949-1963 (2013).

Poeck, H. et al., "Recognition of RNA virus by RIG-I results in activation of CARD9 and inflammasome signaling for interleukin 1 beta production," Nat Immunol., vol. 11:63-69(2010).

Roers, A. et al., "Recognition of Endogenous Nucleic Acids by the Innate Immune System," Immunity, vol. 44(4):739-754(2016).

Schlee, M. et al., "The chase for the RIG-I ligand—recent advances," Mol Therapy, vol. 18:1254-1262 (2010).

Shah, N. et al., "Combined roles of ATP and small hairpin RNA in the activation of RIG-I revealed by solution-based analysis," Nucleic Acids Res., vol. 46(6):3169-3186 (2018).

Simon, A. et al., "RNA conformational changes in the life cycles of RNA viruses, viroids, and virus-associated RNAs," Biochim Biophys Acta, vol. 1789(9-10):571-583(2009).

* cited by examiner

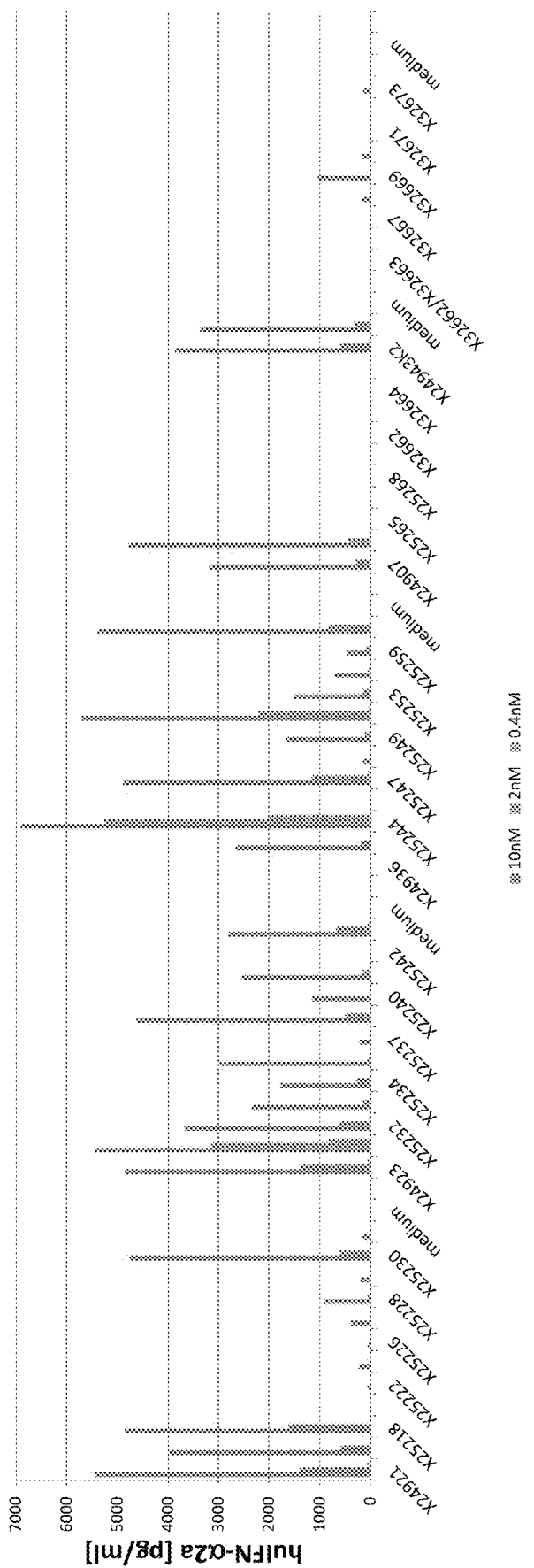

US 10,907,161 B2

SYNTHETIC RIG-I-LIKE RECEPTOR AGONISTS

RELATED APPLICATIONS

This application claims the benefit of U.S. Provisional Application No. 62/659,999, filed on Apr. 19, 2018. The entire content of the aforementioned application is incorporated herein by this reference.

SEQUENCE LISTING

The instant application contains a Sequence Listing which has been submitted electronically in ASCII format and is hereby incorporated by reference in its entirety. Said ASCII copy, created Nov. 5, 2019, is named "CMN-002_Sequence-Listing" and is 46937 bytes in size.

BACKGROUND

Exogenous nucleic acids, particularly viral nucleic acids, introduced into cells induce an innate immune response, resulting in, among other events, interferon (IFN) production and cell death. Upon sensing viral RNA, RIG-I-like receptors induce type I interferon (IFN) secretion leading to upregulation of antiviral IFN-induced proteins in the infected and neighboring cells, which inhibits virus replication. Further downstream events attract immune cells and trigger the adaptive immune response. In addition, RIG-I ligands have been reported to induce the apoptosis of many different types of tumor cells, but not of normal cells.

There remains a need for additional and improved compositions and methods to modulate the activity of immunomodulatory proteins. Such agents can be used for cancer immunotherapy and treatment of other conditions, such as chronic infection. There is a need to develop improved RIG-I-like receptor ligands for diverse therapeutic immunomodulatory applications.

SUMMARY OF THE DISCLOSURE

The present disclosure is based, at least in part, on the discovery of synthetic RNA molecules that function as RIG-I-like receptor agonists.

In some aspects, the disclosure provides a synthetic RIG-I-like receptor (RLR) agonist that specifically binds to a RIG-I-like receptor (RLR), wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof, and wherein the agonist comprises a sequence motif that provides at least one improved biological activity mediated by the RLR relative to an agonist that does not comprise the sequence motif. In some embodiments, the first polynucleotide comprises the sequence motif.

In some embodiments the RLR agonists of the disclosure comprise a sequence motif selected from the group consisting of:
  (i) a GT-repeat motif;
  (ii) a GA-repeat motif;
  (iii) a AUCG-repeat motif;
  (iv) an AU-repeat motif;
  (v) a dipyrimidine motif;
  (vi) a dipurine motif;
  (vii) a pyrimidine triplet motif;
  (viii) a purine triplet motif;
  (ix) a palindromic sequence motif; and
  (x) a combination of any of (i)-(ix).

In some embodiments, the RLR agonists of the disclosure comprise a combination of sequence motifs. In some embodiments the combination of sequence motifs is a GT-repeat motif and a purine triplet motif. In some embodiments, the combination of sequence motifs is an AUCG-repeat motif and a dipyrimidine motif. In some embodiments, the combination of sequence motifs is an AUGC-repeat motif and a dipurine motif.

In some embodiments, the RLR agonists of the disclosure comprise a sequence motif that provides at least one improved biological activity mediated by the RLR relative to an agonist that does not comprise the sequence motif, wherein the at least one improved biological activity is selected from:
  (i) an increase in RLR-mediated cytokine production;
  (ii) an increase in RLR-mediated expression of interferon-stimulated genes;
  (iii) an increase in RLR-mediated intracellular signaling;
  (iv) an increase in binding affinity to RLRs; and
  (v) a combination of any of (i)-(iv).

In some embodiments, the RLR agonists of the disclosure comprise a sequence motif that increases RLR-mediated type I interferon (e.g., IFN-α, IFN-(3) production relative to an agonist that does not comprise the sequence motif. In some embodiments, the RLR agonists of the disclosure comprise a sequence motif that increases RLR-mediated IL-1β production relative to an agonist that does not comprise the sequence motif. In some embodiments, the RLR agonists of the disclosure comprise a sequence motif that increases RLR-mediated IP-10 production relative to an agonist that does not comprise the sequence motif. In some embodiments, the RLR agonists of the disclosure comprise a sequence motif that increases RLR-mediated IL-6, IL-12p70, MCP-1 and/or MIP-1β production relative to an agonist that does not comprise the sequence motif.

In some embodiments, the RLR agonists of the disclosure comprise a sequence motif, wherein the sequence motif is a GT-repeat motif (e.g., GTGTGT) comprising a sequence of <19, about 15-18, about 15, about 10-15, about 10, about 5-10, about 5, about 4, 18, 17, 16, 15, 14, 13, 12, 11, 10, 9, 8, 7, 6, 5, or 4 guanine and thymine nucleotides, or derivatives or analogs thereof. In some embodiments, the sequence motif is a GT-repeat motif comprising a sequence of <19 guanine and thymine nucleotides, or derivatives or analogs thereof. In some embodiments, the sequence motif is a GT-repeat motif comprising a sequence of about 15-18 guanine and thymine nucleotides, or derivatives or analogs thereof. In some embodiments, the sequence motif is a GT-repeat motif comprising a sequence of about 15 guanine and thymine nucleotides, or derivatives or analogs thereof. In some embodiments, the sequence motif is a GT-repeat motif comprising a sequence of about 10-15 guanine and thymine nucleotides, or derivatives or analogs thereof. In some embodiments, the sequence motif is a GT-repeat motif comprising a sequence of about 10 guanine and thymine nucleotides, or derivatives or analogs thereof. In some embodiments, the sequence motif is a GT-repeat motif comprising a sequence of about 5-10 guanine and thymine nucleotides, or derivatives or analogs thereof. In some embodiments, the sequence motif is a GT-repeat motif comprising a sequence of about 5 guanine and thymine nucleotides, or derivatives or analogs thereof. In some embodiments, the sequence motif is a GT-repeat motif comprising a sequence of about 4 guanine and thymine nucleotides, or derivatives or analogs thereof. In some aspects, the GT-repeat motif provides an improved biological activity in the RLR agonist, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In some embodiments, the RLR agonists of the disclosure comprise a sequence motif, wherein the sequence motif is a GT-repeat motif comprising a sequence of 18, 17, 16, 15, 14, 13, 12, 11, 10, 9, 8, 7, 6, 5, or 4 guanine and thymine nucleotides, or derivatives or analogs thereof. In some embodiments, the sequence motif is a GT-repeat motif comprising a sequence of 18 guanine and thymine nucleotides, or derivatives or analogs thereof. In some embodiments, the sequence motif is a GT-repeat motif comprising a sequence of 16 guanine and thymine nucleotides, or derivatives or analogs thereof. In some embodiments, the sequence motif is a GT-repeat motif comprising a sequence of 14 guanine and thymine nucleotides, or derivatives or analogs thereof. In some embodiments, the sequence motif is a GT-repeat motif comprising a sequence of 12 guanine and thymine nucleotides, or derivatives or analogs thereof. In some embodiments, the sequence motif is a GT-repeat motif comprising a sequence of 10 guanine and thymine nucleotides, or derivatives or analogs thereof. In some embodiments, the sequence motif is a GT-repeat motif comprising a sequence of 8 guanine and thymine nucleotides, or derivatives or analogs thereof. In some embodiments, the sequence motif is a GT-repeat motif comprising a sequence of 6 guanine and thymine nucleotides, or derivatives or analogs thereof. In some embodiments, the sequence motif is a GT-repeat motif comprising a sequence of 4 guanine and thymine nucleotides, or derivatives or analogs thereof. In some embodiments, the RLR agonists of the disclosure comprise a sequence motif, wherein the sequence motif is a GT-repeat motif, wherein the GT-repeat motif is $[GT]_n$, wherein n=2 to 9, 3-7, or 4-8. In some aspects, the GT-repeat motif provides an improved biological activity in the RLR agonist, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In some aspects, the disclosure provides an RLR agonist that specifically binds to an RLR, wherein the agonist comprises a blunt-ended, hairpin RNA comprising a first polynucleotide connected to (operably linked to) a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof, wherein the agonist comprises a sequence motif that provides at least one improved biological activity mediated by the RLR relative to an agonist that does not comprise the sequence motif, wherein the first polynucleotide comprises the sequence motif, and wherein the sequence motif is a GT-repeat motif comprising a sequence of about 14 guanine and thymine nucleotides. In some embodiments, the sequence motif is a GT-repeat motif, wherein the GT-repeat motif is $[GT]_7$. In some aspects, the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In some aspects, the disclosure provides an RLR agonist that specifically binds to an RLR, wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof, wherein the agonist comprises a sequence motif that provides at least one improved biological activity mediated by the RLR relative to an agonist that does not comprise the sequence motif, wherein the first polynucleotide comprises the sequence motif, and wherein the sequence motif is a GT-repeat motif comprising a sequence of 6 guanine and thymine nucleotides. In some embodiments, the sequence motif is a GT-repeat motif, wherein the GT-repeat motif is $[GT]_3$. In some embodiments, the sequence motif is a GT-repeat motif, wherein the GT-repeat motif is $[GT]_3$, and wherein the GT-repeat is followed by a purine triplet and UCG, respectively. In some embodiments, the purine triplet is GGA. In some aspects, the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In some embodiments, the RLR agonists of the disclosure comprise a sequence motif, wherein the sequence motif is a GA-repeat motif (e.g., GAGAGA) comprising a sequence of <19, about 15-18, about 15, about 10-15, about 10, about 5-10, about 5, about 4, 18, 17, 16, 15, 14, 13, 12, 11, 10, 9, 8, 7, 6, 5, or 4 guanine and adenine nucleotides, or derivatives or analogs thereof. In some embodiments, the sequence motif is a GA-repeat motif comprising a sequence of <19 guanine and adenine nucleotides, or derivatives or analogs thereof. In some embodiments, the sequence motif is a GA-repeat motif comprising a sequence of about 15-18 guanine and adenine nucleotides, or derivatives or analogs thereof. In some embodiments, the sequence motif is a GA-repeat motif comprising a sequence of about 15 guanine and adenine nucleotides, or derivatives or analogs thereof. In some embodiments, the sequence motif is a GA-repeat motif comprising a sequence of about 10-15 guanine and adenine nucleotides, or derivatives or analogs thereof. In some embodiments, the sequence motif is a GA-repeat motif comprising a sequence of about 10 guanine and adenine nucleotides, or derivatives or analogs thereof. In some embodiments, the sequence motif is a GA-repeat motif comprising a sequence of about 5-10 guanine and adenine nucleotides, or derivatives or analogs thereof. In some embodiments, the sequence motif is a GA-repeat motif comprising a sequence of about 5 guanine and adenine nucleotides, or derivatives or analogs thereof. In some embodiments, the sequence motif is a GA-repeat motif comprising a sequence of about 4 guanine and adenine nucleotides, or derivatives or analogs thereof. In some aspects, the GA-repeat motif provides an improved biological activity in the RLR agonist, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In some embodiments, the RLR agonists of the disclosure comprise a sequence motif is a GA-repeat motif comprising a sequence of 18, 17, 16, 15, 14, 13, 12, 11, 10, 9, 8, 7, 6, 5, or 4 guanine and adenine nucleotides, or derivatives or analogs thereof. In some embodiments, the sequence motif is a GA-repeat motif comprising a sequence of 18 guanine and adenine nucleotides, or derivatives or analogs thereof. In some embodiments, the sequence motif is a GA-repeat motif comprising a sequence of 16 guanine and adenine nucleotides, or derivatives or analogs thereof. In some embodiments, the sequence motif is a GA-repeat motif comprising a sequence of 14 guanine and adenine nucleotides, or derivatives or analogs thereof. In some embodiments, the sequence motif is a GA-repeat motif comprising a sequence of 12 guanine and adenine nucleotides, or derivatives or analogs thereof. In some embodiments, the sequence motif is a GA-repeat motif comprising a sequence of 8 guanine and adenine nucleotides, or derivatives or analogs thereof. In some embodiments, the sequence motif is a GA-repeat motif comprising a sequence of 6 guanine and adenine nucleotides, or derivatives or analogs thereof. In some embodiments, the sequence motif is a GA-repeat motif comprising a sequence of 4 guanine and adenine nucleotides, or derivatives or analogs thereof.

In some embodiments, the RLR agonists of the disclosure comprise a sequence motif, wherein the sequence motif is a GA-repeat motif, wherein the GA-repeat motif is $[GA]_n$, where n=2 to 9, 3 to 7 or 4 to 8. In some aspects, the GA-repeat motif provides an improved biological activity in the RLR agonist, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In some aspects, the disclosure provides an RLR agonist that specifically binds to an RLR, wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof, wherein the agonist comprises a sequence motif that provides at least one improved biological activity mediated by the RLR relative to an agonist that does not comprise the sequence motif, wherein the first polynucleotide comprises the sequence motif, and wherein the sequence motif is a GA-repeat motif comprising a sequence of about 14 guanine and adenine nucleotides. In some embodiments, the sequence motif is a GA-repeat motif, wherein the GA-repeat motif is $[GA]_7$. In some aspects, the GA-repeat motif provides an improved biological activity in the RLR agonist, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In some embodiments, the RLR agonists of the disclosure comprise a sequence motif, wherein the sequence motif is a AUCG-repeat motif (e.g., AUCGAUCG) comprising a sequence of <19, about 16, about 12-16, about 12, about 8-12, about 6, 16, 12, 8 adenine, uracil, cytosine, and guanine nucleotides, or derivatives or analogs thereof. In some embodiments, the sequence motif is a AUCG-repeat motif comprising a sequence of <19 adenine, uracil, cytosine, and guanine nucleotides, or derivatives or analogs thereof. In some embodiments, the sequence motif is a AUCG-repeat motif comprising a sequence of about 16 adenine, uracil, cytosine, and guanine nucleotides, or derivatives or analogs thereof. In some embodiments, the sequence motif is a AUCG-repeat motif comprising a sequence of about 12-16 adenine, uracil, cytosine, and guanine nucleotides, or derivatives or analogs thereof. In some embodiments, the sequence motif is a AUCG-repeat motif comprising a sequence of about 12 adenine, uracil, cytosine, and guanine nucleotides, or derivatives or analogs thereof. In some embodiments, the sequence motif is a AUCG-repeat motif comprising a sequence of about 8-12 adenine, uracil, cytosine, and guanine nucleotides, or derivatives or analogs thereof. In some embodiments, the sequence motif is a AUCG-repeat motif comprising a sequence of about 6 adenine, uracil, cytosine, and guanine nucleotides, or derivatives or analogs thereof. In some embodiments, the sequence motif is a AUCG-repeat motif comprising a sequence of 16 adenine, uracil, cytosine, and guanine nucleotides, or derivatives or analogs thereof. In some embodiments, the sequence motif is a AUCG-repeat motif comprising a sequence of 12 adenine, uracil, cytosine, and guanine nucleotides, or derivatives or analogs thereof. In some embodiments, the sequence motif is a AUCG-repeat motif comprising a sequence of 8 adenine, uracil, cytosine, and guanine nucleotides, or derivatives or analogs thereof. In some aspects, the AUCG-repeat motif provides an improved biological activity in the RLR agonist, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In some embodiments, the RLR agonists of the disclosure comprise a sequence motif, wherein the sequence motif is an AUCG-repeat motif, wherein the AUCG-repeat motif is $[AUCG]_n$, where n=2 to 4 or 2, 3 or 4. In some aspects, the AUCG-repeat motif provides an improved biological activity in the RLR agonist, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In some aspects, the disclosure provides an RLR agonist that specifically binds to an RLR, wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof, wherein the agonist comprises a sequence motif that provides at least one improved biological activity mediated by the RLR relative to an agonist that does not comprise the sequence motif, wherein the first polynucleotide comprises the sequence motif, and wherein the sequence motif is a AUCG-repeat motif comprising a sequence of about 12 guanine and adenine nucleotides. In some embodiments, the AUCG-repeat motif is $[AUCG]_3$. In some aspects, the AUCG-repeat motif provides an improved biological activity in the RLR agonist, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In some embodiments, the RLR agonists of the disclosure comprise a AUCG-repeat motif, wherein the motif is preceded by a CG or a dipyrimidine motif. In some embodiments, the AUCG-repeat motif is preceded by a CG. In some embodiments, the AUCG-repeat motif is [AUCG]$_3$ and is preceded by a CG. In some embodiments, the AUCG-repeat motif is [AUCG]$_3$ and is preceded by the dipyrimidine motif CC.

In some embodiments, the RLR agonists of the disclosure comprise an AUCG-repeat motif, wherein the motif is preceded by a dipurine motif. In some embodiments, the dipurine motif is GA. In some embodiments, the AUCG-repeat motif is [AUCG]$_3$ and is preceded by the dipurine motif GA. In some embodiments, the AUCG-repeat motif is preceded by the dipurine motif II.

In some embodiments, the RLR agonists of the disclosure comprise an AUCG-repeat motif, wherein one or more uridine nucleosides (U) are substituted with a modified nucleoside. In some embodiments, wherein the modified nucleoside is ribothymidine (T). In some embodiments, the AUGC-repeat motif is [AUCG]$_3$, wherein the one or more uridine nucleosides (U) comprising the AUCG-repeat motif are substituted with a modified nucleoside, wherein the modified nucleoside is ribothymidine (T). In some embodiments, the AUGC-repeat motif is [AUCG]$_3$, wherein the one or more uridine nucleosides (U) comprising the AUCG-repeat motif are substituted with a modified nucleoside, wherein the modified nucleoside is ribothymidine (T), and wherein the AUGC-repeat motif is preceded by GG.

In some embodiments, the RLR agonists of the disclosure comprise an AUCG-repeat motif, wherein one or more guanosine nucleosides (G) are substituted with a modified nucleoside. In some embodiments, the modified nucleoside is inosine (I). In some embodiments, the AUGC-repeat motif is [AUCG]$_3$, wherein the one or more guanosine nucleosides (G) comprising the AUCG-repeat motif are substituted with a modified nucleoside, wherein the modified nucleoside is ribothymidine (T), and wherein the AUGC-repeat motif is preceded by GG.

In some embodiments, the RLR agonists of the disclosure comprise a AUCG-repeat motif, wherein the motif is preceded by a IG. In some embodiments, the AUCG-repeat motif is [AUCG]$_3$ and is preceded by a IG.

In some embodiments, the RLR agonists of the disclosure comprise an AUCG-repeat, wherein one or more guanosine nucleosides (G) are substituted with an inosine (I), wherein the AUCG-repeat is preceded by an inosine (I). In some embodiments, the guanosine nucleosides (G) comprising the AUCG-repeat are substituted with an inosine (I), wherein the AUCG-repeat is preceded by an inosine (I), wherein the 5' most nucleotide of the first polynucleotide comprises inosine (I).

In some embodiments, the RLR agonists of the disclosure comprise an AUCG-repeat motif, wherein the AUCG-repeat motif is [AUCG]$_2$. In some embodiments, the sequence motif is an AUCG-repeat motif, wherein the AUCG-repeat motif is [AUCG]$_2$, and wherein the AUCG-repeat motif is preceded by a dipurine motif. In some embodiments, the sequence motif is an AUCG-repeat motif, wherein the AUCG-repeat motif is [AUCG]$_2$, wherein the AUCG-repeat motif is preceded by a dipurine motif, and wherein the dipurine motif is GG.

In some embodiments, the RLR agonists of the disclosure comprise an AUCG-repeat motif, wherein the AUCG-repeat motif is [AUCG]$_2$, and wherein the AUCG-repeat motif is preceded by a purine triplet motif. In some embodiments, the purine triplet motif is GGG. In some embodiments, the sequence motif is an AUCG-repeat motif, wherein the AUCG-repeat motif is [AUCG]$_2$, wherein the AUCG-repeat motif is preceded by a purine triplet motif, and wherein the purine triplet motif is GGG. In some embodiments, the sequence motif is an AUCG-repeat motif, wherein the AUCG-repeat motif is [AUCG]$_2$, and wherein the AUCG-repeat motif is preceded by CCCCCG. In some embodiments, the sequence motif is an AUCG-repeat motif, wherein the AUCG-repeat motif is [AUCG]$_2$, and wherein the AUCG-repeat motif is preceded by TCGUCG.

In some embodiments, the RLR agonists of the disclosure comprise a sequence motif, wherein the sequence motif is a palindromic sequence comprising a sequence of <19, about 15-18, about 15, about 10-15, about 10, about 18, 17, 16, 15, 14, 13, 12, 11, 10, 9, 8, 7, 6, 5, or 4 nucleotides, or derivatives or analogs thereof, linked in any order that results in a palindrome. In some embodiments, the sequence motif is a palindromic sequence comprising a sequence of <19 nucleotides, or derivatives or analogs thereof, linked in any order that results in a palindrome. In some embodiments, the sequence motif is a palindromic sequence comprising a sequence of about 15-18 nucleotides, or derivatives or analogs thereof, linked in any order that results in a palindrome. In some embodiments, the sequence motif is a palindromic sequence comprising a sequence of about 15 nucleotides, or derivatives or analogs thereof, linked in any order that results in a palindrome. In some embodiments, the sequence motif is a palindromic sequence comprising a sequence of about 10-15 nucleotides, or derivatives or analogs thereof, linked in any order that results in a palindrome. In some embodiments, the sequence motif is a palindromic sequence comprising a sequence of about 10 nucleotides, or derivatives or analogs thereof, linked in any order that results in a palindrome. In some embodiments, the sequence motif is a palindromic sequence comprising a sequence of 18 nucleotides, or derivatives or analogs thereof, linked in any order that results in a palindrome. In some embodiments, the sequence motif is a palindromic sequence comprising a sequence 17 nucleotides, or derivatives or analogs thereof, linked in any order that results in a palindrome. In some embodiments, the sequence motif is a palindromic sequence comprising a sequence of 16 nucleotides, or derivatives or analogs thereof, linked in any order that results in a palindrome. In some embodiments, the sequence motif is a palindromic sequence comprising a sequence of 15 nucleotides, or derivatives or analogs thereof, linked in any order that results in a palindrome. In some embodiments, the sequence motif is a palindromic sequence comprising a sequence of 14 nucleotides, or derivatives or analogs thereof, linked in any order that results in a palindrome. In some embodiments, the sequence motif is a palindromic sequence comprising a sequence of 13 nucleotides, or derivatives or analogs thereof, linked in any order that results in a palindrome. In some embodiments, the sequence motif is a palindromic sequence comprising a sequence of 12 nucleotides, or derivatives or analogs thereof, linked in any order that results in a palindrome. In some embodiments, the sequence motif is a palindromic sequence comprising a sequence of 11 nucleotides, or derivatives or analogs thereof, linked in any order that results in a palindrome. In some embodiments, the sequence motif is a palindromic sequence comprising a sequence of 10 nucleotides, or derivatives or analogs thereof, linked in any order that results in a palindrome. In some embodiments, the sequence motif is a palindromic sequence comprising a sequence of 9 nucleotides, or derivatives or analogs thereof, linked in any order that results in a palindrome. In some embodiments, the sequence motif is a palindromic sequence comprising a sequence of 8 nucleotides, or derivatives or analogs thereof, linked in any order that results in a palindrome. In some embodiments, the sequence motif is a palindromic sequence comprising a sequence of 7 nucleotides, or derivatives or analogs thereof, linked in any order that results in a palindrome. In some embodiments, the sequence motif is a palindromic sequence comprising a sequence of 6 nucleotides, or derivatives or analogs thereof, linked in any order that results in a palindrome. In some embodiments, the sequence motif is a palindromic sequence comprising a sequence of 5 nucleotides, or derivatives or analogs thereof, linked in any order that results in a palindrome. In some embodiments, the sequence motif is a palindromic sequence comprising a sequence of 4 nucleotides, or derivatives or analogs thereof, linked in any order that results in a palindrome.

In some embodiments, the RLR agonists of the disclosure comprise a linker, wherein the linker is flanked by AU. In some embodiments, the linker is flanked by an AU-repeat motif, wherein the AU-repeat motif is $[AU]_n$, where n=2 to 3. In some embodiments, the AU-repeat motif is $[AU]_2$.

In some aspects, the disclosure provides an RLR agonist that specifically binds to RLRs, wherein the agonist comprises a blunt-ended, hairpin RNA comprising the formula:

5'-($N_1$-$N_2$-$X_1$)-L-($X_2$-$N_3$-$N_4$)-3', wherein ($N_1$-$N_2$-$X_1$) comprises a first polynucleotide comprising linked nucleotides $N_1$, $N_2$ and $X_1$;

(ii) ($X_2$-$N_3$-$N_4$) comprises a second polynucleotide comprising linked nucleotides $X_2$, $N_3$ and $N_4$;

(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;

(iv) $N_1$ base pairs with $N_4$;

(v) N2 base pairs with $N_3$;

(vi) $N_1$ comprises a 5' diphosphate or triphosphate moiety, or derivative or analog thereof;

(vii) $X_1$ and $X_2$ are each oligonucleotides comprising nucleosides selected from the group consisting of: adenosine, guanosine, cytidine, 5-methyluridine, uridine and inosine;

(viii) $X_1$ is complementary to $X_2$;

(ix) $X_1$ and $X_2$ are each 12 nucleotides to 16 nucleotides in length and are the same length, and;

(x) L is a linker that operably links the first polynucleotide and the second polynucleotide, wherein at least one of N1, N2, N3, and N4 is inosine and/or at least one of X1 and/or X2 comprises at least one inosine nucleoside, and wherein the inosine nucleoside base pairs with cytidine in the hairpin RNA. In some aspects, the RLR agonist of the disclosure has an improved biological activity, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In some aspects, the disclosure provides an RLR agonist that specifically binds to RLRs, wherein the agonist comprises a blunt-ended, hairpin RNA comprising a non-nucleotide linker, and wherein the agonist comprises the formula:

5'-($N_1$-$N_2$-$X_1$)-L-($X_2$-$N_3$-$N_4$)-3', wherein (i) ($N_1$-$N_2$-$X_1$) comprises a first polynucleotide comprising linked nucleotides $N_1$, $N_2$ and $X_1$;

(ii) (X2-$N_3$-$N_4$) comprises a second polynucleotide comprising linked nucleotides $X_2$, $N_3$ and $N_4$;

(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;

(iv) $N_1$ base pairs with $N_4$;

(v) $N_2$ base pairs with $N_3$;

(vi) $N_1$ comprises a 5' diphosphate or triphosphate moiety, or derivative or analog thereof;

(vii) $X_1$ and $X_2$ are each oligonucleotides comprising nucleosides selected from the group consisting of: adenosine, guanosine, cytidine, 5-methyluridine, uridine and inosine;

(viii) $X_1$ is complementary to $X_2$;

(ix) $X_1$ and $X_2$ are each 12 nucleotides to 16 nucleotides in length and are the same length, and;

(x) L is the non-nucleotide linker that covalently links the first polynucleotide and the second polynucleotide, wherein inosine, if present, base pairs with cytidine. In some aspects, the RLR agonist of the disclosure has an improved biological activity, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In some embodiments, N1 comprises inosine and N4 comprises cytidine. In some embodiments, N1 comprises inosine and N4 comprises cytidine and X1 and X2 are each 12 nucleotides in length. In some embodiments, N1 comprises cytidine and N4 comprises inosine. In some embodiments, N2 comprise inosine and N3 comprises cytidine. In some embodiments, N2 comprises cytidine and N3 comprises inosine. In some embodiments, N1 comprises guanosine. In some embodiments, N2 comprises guanosine. In some embodiments, N1 comprises cytidine. In some embodiments, N2 comprises cytidine. In some embodiments, N1 and N2 comprise guanosine and $N_3$ and $N_4$ comprise cytidine. In some embodiments, N1 and N2 comprise cytidine and $N_3$ and $N_4$ comprise guanosine. In some embodiments, N1 and N2 comprise inosine and $N_3$ and $N_4$ comprise cytidine. In some embodiments, N1 and N2 comprise cytidine and $N_3$ and $N_4$ comprise inosine.

In some embodiments, the RLR agonists of the disclosure comprise the formula:

5'-($N_1$-$N_2$-X1)-L-($X_2$-$N_3$-$N_4$)-3', wherein (i) ($N_1$-$N_2$-$X_1$) comprises a first polynucleotide comprising linked nucleotides $N_1$, $N_2$ and $X_1$;

(ii) ($X_2$-$N_3$-$N_4$) comprises a second polynucleotide comprising linked nucleotides $X_2$, $N_3$ and $N_4$;

(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;

(iv) $N_1$ base pairs with $N_4$;

(v) $N_2$ base pairs with $N_3$;

(vi) $N_1$ comprises a 5' diphosphate or triphosphate moiety, or derivative or analog thereof;

(vii) $X_1$ and $X_2$ are each oligonucleotides comprising nucleosides selected from the group consisting of: adenosine, guanosine, cytidine, 5-methyluridine, uridine and inosine;

(viii) $X_1$ is complementary to $X_2$;

(ix) $X_1$ and $X_2$ are each 12 nucleotides to 16 nucleotides in length and are the same length, and;

(x) L is the non-nucleotide linker that covalently links the first polynucleotide and the second polynucleotide, wherein inosine, if present, base pairs with cytidine, and wherein N1 comprises inosine and N4 comprises cytidine, and X1 and/or X2 each comprise at least one inosine. In some embodiments, N2 comprises inosine and N3 comprises cytidine, and X1 and/or X2 each comprise at least one inosine. In some embodiments, N1 and N2 comprise guanosine $N_3$ and $N_4$ comprise cytidine, and X1 and/or X2 each comprise at least one inosine. In some embodiments, N1 and N2 comprise guanosine and $N_3$ and $N_4$ comprise cytidine, and X1 and X2 each comprise at least one inosine. In some embodiments, N1 and N2 comprise guanosine and N3 and N4 comprise cytidine, X1 and X2 each comprise at least one inosine, and X1 and X2 are each 12 nucleotides in length. In some embodiments, N1 and N2 comprise cytidine and N3 and N4 comprise guanosine, and X1 and X2 each comprise at least one inosine. In some embodiments, N1 and N2 comprise guanosine and N3 and N4 comprise cytidine, and X1 and X2 each comprise inosine and no guanosine nucleosides. In some embodiments, N1 and N2 comprise guanosine and N3 and N4 comprise cytidine, X1 and X2 each comprise at least one inosine, and X1 and X2 are each 12 nucleotides in length. In some embodiments, N1 and N2 comprise cytidine and N3 and N4 comprise guanosine, and X1 and X2 each comprise inosine and no guanosine nucleosides. In some aspects, the RLR agonist of the disclosure has an improved biological activity, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In some embodiments, the RLR agonists of the disclosure comprise the formula:

5'-($N_1$-$N_2$-$X_1$)-L-($X_2$-$N_3$-$N_4$)-3', wherein (i) ($N_1$-$N_2$-$X_1$) comprises a first polynucleotide comprising linked nucleotides $N_1$, $N_2$ and $X_1$;

(ii) ($X_2$-$N_3$-$N_4$) comprises a second polynucleotide comprising linked nucleotides $X_2$, $N_3$ and $N_4$;

(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;

(iv) $N_1$ base pairs with $N_4$;

(v) $N_2$ base pairs with $N_3$;

(vi) $N_1$ comprises a 5' diphosphate or triphosphate moiety, or derivative or analog thereof;

(vii) $X_1$ and $X_2$ are each oligonucleotides comprising nucleosides selected from the group consisting of: adenosine, guanosine, cytidine, 5-methyluridine, uridine and inosine;

(viii) $X_1$ is complementary to $X_2$;

(ix) $X_1$ and $X_2$ are each 12 nucleotides to 16 nucleotides in length and are the same length, and;

(x) L is the non-nucleotide linker that covalently links the first polynucleotide and the second polynucleotide, wherein inosine, if present, base pairs with cytidine, and wherein N1 and N2 comprise inosine and $N_3$ and $N_4$ comprise cytidine, and X1 and/or X2 each comprise at least one inosine. In some embodiments, N1 and N2 comprise inosine and $N_3$ and $N_4$ comprise cytidine, X1 and X2 each comprise at least one inosine, and X1 and X2 are each 12 nucleotides in length. In some embodiments, N1 and N2 comprise inosine and $N_3$ and $N_4$ comprise cytidine, and X1 and X2 each comprise at least one inosine. In some embodiments, N1 and N2 comprise inosine and N3 and N4 comprise cytidine, X1 and X2 each comprise at least one inosine, and X1 and X2 are each 12 nucleotides in length. In some embodiments, N1 and N2 comprise cytidine and N3 and N4 comprise inosine, and X1 and/or X2 each comprise at least one inosine. In some embodiments, N1 and N2 comprise inosine and $N_3$ and $N_4$ comprise cytidine, and X1 and X2 comprise inosine and no guanosine nucleosides. In some embodiments, N1 and N2 comprise cytidine and $N_3$ and $N_4$ comprise inosine, and X1 and X2 comprise inosine and no guanosine nucleosides. In some aspects, the RLR agonist of the disclosure has an improved biological activity, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In some embodiments, the RLR agonists of the disclosure comprise the formula:

5'-($N_1$-$N_2$-$X_1$)-L-($X_2$-$N_3$-$N_4$)-3', wherein X1 and X2 are each 12 nucleotides and comprise 1, 2, 3 or 4 inosine nucleosides. In some embodiments, X1 and X2 are each 13 nucleotides and comprise 1, 2, 3, 4 or 5 inosine nucleosides. In some embodiments, X1 and X2 are each 14 nucleotides and comprise 1, 2, 3, 4, 5 or 6 inosine nucleosides. In some embodiments, X1 and X2 are each 15 nucleotides and comprise 1, 2, 3, 4, 5, 6, or 7 inosine nucleosides. In some embodiments, X1 and X2 are each 16 nucleotides and each comprise 1, 2, 3, 4, 5, 6, 7, or 8 inosine nucleosides. In some embodiments, X1 and X2 are each 12 nucleotides and comprise at least 10%, 20%, 30% or 40% inosine nucleosides. In some aspects, the RLR agonist of the disclosure has an improved biological activity, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In some aspects, the disclosure provides an RLR agonist that specifically binds to RLRs, wherein the agonist comprises a blunt-ended, hairpin RNA comprising the formula:

5'-($N_1$-$N_2$-$X_1$)-L-($X_2$-$N_3$-$N_4$)-3', wherein ($N_1$-$N_2$-$X_1$) comprises a first polynucleotide comprising linked nucleotides $N_1$, $N_2$ and $X_1$, (ii) ($X_2$-$N_3$-$N_4$) comprises a second polynucleotide comprising linked nucleotides $X_2$, $N_3$ and $N_4$;

(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;

(iv) $N_1$ base pairs with $N_4$;

(v) $N_2$ base pairs with $N_3$;

(vi) $N_2$ comprises a 5' diphosphate or triphosphate moiety, or derivative or analog thereof;

(vii) $X_1$ comprises a sequence motif $[AUCN_5]_x$, wherein $N_5$ is comprises guanosine or inosine, wherein x is an integer whose value indicates the number of sequence motifs, and wherein x=3 or 4;

(viii) X$_2$ comprises a sequence motif [CN$_6$AU]$_y$, wherein N6 comprises guanosine or inosine, wherein y is an integer whose value indicates the number of sequence motifs, and wherein y=3 or 4;

(ix) L is a linker that operably links the first polynucleotide and the second polynucleotide, optionally, wherein at least one of N1, N2, N3, and N4 is inosine, and wherein the inosine nucleoside base pairs with cytidine in the hairpin RNA.

In some embodiments, N5 comprises inosine and N6 comprises inosine. In some embodiments, N5 comprises guanosine and N6 comprises inosine. In some embodiments, N5 comprises inosine and N6 comprises guanosine. In some embodiments, N5 comprises guanosine (G) and N6 comprises guanosine (G). In some embodiments, x=3 and y=3. In some embodiments, x=4 and y=4. In some embodiments, N1 comprises inosine (I) and N4 comprises cytidine (C). In some embodiments, N2 comprises inosine (I) and N3 comprises cytidine (C). In some embodiments, N3 comprises inosine (I) and N2 comprises cytidine (C). In some embodiments, N4 comprises inosine (I) and N1 comprises cytidine (C). In some embodiments, N1 comprises guanosine (G). In some embodiments, N2 comprises guanosine (G). In some embodiments, N1 comprises cytidine (C). In some embodiments, N2 comprises cytidine (C). In some embodiments, N1 and N2 comprise guanosine (G) and N$_3$ and N$_4$ comprise cytidine (C). In some embodiments, N1 and N2 comprise cytidine (C) and N$_3$ and N$_4$ comprise guanosine (G). In some embodiments, N1 and N2 comprise inosine (I) and N$_3$ and N$_4$ comprise cytidine (C). In some embodiments, N1 and N2 comprise cytidine (C) and N$_3$ and N$_4$ comprise inosine (I). In some aspects, the RLR agonist of the disclosure has an improved biological activity, wherein the improved biological activity is an increase in RLR-mediated cytokine production; an increase in RLR-mediated expression of interferon-stimulated genes; an increase in RLR-mediated intracellular signaling; an increase in binding affinity to RLRs; and a combination of any of the foregoing.

In some embodiments of the RLR agonist of the disclosure comprises a linker, wherein the linker is a nucleotide linker or a non-nucleotide linker. In some embodiments, the linker is a non-nucleotide linker. In some embodiments, the linker is a nucleotide linker. In some embodiments, the nucleotide linker comprises a tetraloop, wherein the nucleotide sequence of the tetraloop is selected from the group consisting of:

(a) UNCG, wherein N=A, C, G, or U;
(b) GNRA, wherein N=A, C, G, or U, and wherein R=A or G;
(c) ANYA, wherein N=A, C, G, or U, and wherein Y=C or T;
(d) CUYG, wherein Y=C or T;
(e) UMAC, wherein M=A or C; and
(f) CUUG.

In some embodiments, the sequence of the tetraloop is UUCG. In some embodiments, the sequence of the tetraloop is GAUC.

In some embodiments, the RLR agonist of the disclosure comprises a nucleotide linker, wherein the nucleotide linker comprises the nucleotide sequence UUUGAU or UGUUU. In some embodiments, the nucleotide linker comprises the nucleotide sequence UUUGAU. In some embodiments, the nucleotide linker comprises the nucleotide sequence UGUUU.

In some embodiments, the RLR agonist of the disclosure comprises a non-nucleotide linker, wherein the non-nucleotide linker is selected from the group consisting of:

(a) an ethylene glycol linker; and
(b) an alkyl linker.

In some embodiments, the non-nucleotide linker is a hexaethylene glycol linker. In some embodiments, the non-nucleotide linker is a C9 alkyl linker.

In some embodiments, the RLR agonist of the disclosure comprises a 5' diphosphate moiety, or a derivative or analog thereof. In some embodiments, the agonist comprises a 5' triphosphate moiety, or a derivative or analog thereof. In some embodiments, the derivative or analog thereof comprises a phosphate bioisostere is selected from: a phosphonate, a thiophosphonate, a phosphorothioate, a sulfate, a sulfonate, a sulfamate, a thiazolidinone, a carboxylate, a malonate, a boronic acid, a benzoxaborole, a boranophosphate, a squaramide.

In some embodiments, the agonist comprises a modified nucleotide, a modified nucleoside, or a modified nucleobase, or a combination thereof. In some embodiments, the agonist comprises a modification to the internucleotide linkages or to the polynucleotide backbone.

In some embodiments, the RLR agonist of the disclosure exhibits one or more of the following properties:
(a) specifically binds to one or more RLRs (e.g. RIG-1, MDA5 and/or LGP2);
(b) increases RLR-mediated cytokine production;
(c) increases RLR-mediated expression of interferon-stimulated genes (ISGs);
(d) increases RLR-dependent intracellular signaling;
(e) increases stability of the duplex;
(f) increases binding affinity to RLRs;
(g) decreases off-target binding;
(h) increases biological half-life;
(i) increases biodistribution and bioavailability;
(j) increases and/or enhances uptake into cells and/or tissues;
(k) decreases immunogenicity; and
(l) a combination of any of (a)-(k).

In some aspects, the disclosure provides an RLR agonist that specifically binds to RLRs, wherein the agonist comprises a blunt-ended, hairpin RNA comprising the formula:

5'-(N$_1$-N$_2$-X$_1$)-L-(X$_2$-N$_3$-N$_4$)-3', wherein (i) (N$_1$-N$_2$-X$_1$) comprises a first polynucleotide comprising linked nucleotides N$_1$, N$_2$ and X$_1$,
(ii) (X2-N$_3$-N$_4$) comprises a second polynucleotide comprising linked nucleotides X$_2$, N$_3$ and N$_4$;
(iii) N$_1$, N$_2$, N$_3$ and N$_4$ each comprise a single nucleotide comprising a nucleoside selected from the group consisting of: adenosine, guanosine, cytidine, 5-methyluridine, uridine and inosine;
(iv) N$_1$ base pairs with N$_4$;
(v) N$_2$ base pairs with N$_3$;
(vi) N$_1$ comprises a 5' diphosphate or triphosphate moiety, or derivative or analog thereof;
(vii) X$_1$ and X$_2$ are each oligonucleotides comprising nucleosides selected from the group consisting of: adenosine, guanosine, cytidine, 5-methyluridine, uridine and inosine;
(viii) X$_1$ is complementary to X$_2$;
(ix) X$_1$ and X$_2$ are each 12 nucleotides to 16 nucleotides in length and are the same length, and;
(x) L is a linker that operably links the first polynucleotide and the second polynucleotide, wherein N1 and N2 each comprise guanosine, wherein N$_3$ and N$_4$ each comprise cytidine, wherein X1 and X2 are each 12 nucleotides in length, wherein X1 and X2 each comprise at least one inosine nucleoside, wherein the inosine nucleoside base pairs with cytidine in the hairpin RNA, and wherein L comprises a nucleotide linker comprising a tetraloop, wherein the nucleotide sequence of the tetraloop is UUCG.

In some aspects, the disclosure provides an RLR agonist that specifically binds to RLRs, wherein the agonist comprises a blunt-ended, hairpin RNA comprising the formula:

5'-(N$_1$-N$_2$-X$_1$)-L-(X$_2$-N$_3$-N$_4$)-3', wherein (i) (N$_1$-N$_2$-X$_1$) comprises a first polynucleotide comprising linked nucleotides N$_1$, N$_2$ and X$_1$;
(ii) (X$_2$-N$_3$-N$_4$) comprises a second polynucleotide comprising linked nucleotides X$_2$, N$_3$ and N$_4$;
(iii) N$_1$, N$_2$, N$_3$ and N$_4$ each comprise a single nucleotide comprising a nucleoside selected from the group consisting of: adenosine, guanosine, cytidine, 5-methyluridine, uridine and inosine;
(iv) N$_1$ base pairs with N$_4$;
(v) N$_2$ base pairs with N$_3$;
(vi) N$_1$ comprises a 5' diphosphate or triphosphate moiety, or derivative or analog thereof;
(vii) X$_1$ and X$_2$ are each oligonucleotides comprising nucleosides selected from the group consisting of: adenosine, guanosine, cytidine, 5-methyluridine, uridine and inosine;
(viii) X$_1$ is complementary to X$_2$;
(ix) X$_1$ and X$_2$ are each 12 nucleotides to 16 nucleotides in length and are the same length, and;
(x) L is a linker that operably links the first polynucleotide and the second polynucleotide,
wherein N1 comprises inosine and N2 comprise guanosine, wherein N3 and N4 each comprise cytidine, wherein X1 and X2 are each 12 nucleotides in length, wherein X1 and X2 each comprise at least one inosine nucleoside, wherein the inosine nucleoside base pairs with cytidine in the hairpin RNA, and wherein L comprises a nucleotide linker comprising a tetraloop, wherein the nucleotide sequence of the tetraloop is UUCG.

In some aspects, the disclosure provides an RLR agonist that specifically binds to RLRs, wherein the agonist comprises a blunt-ended, hairpin RNA comprising the formula:

5'-(N$_1$-N$_2$-X$_1$)-L-(X$_2$-N$_3$-N$_4$)-3', wherein (i) (N$_1$-N$_2$-X$_1$) comprises a first polynucleotide comprising linked nucleotides N$_1$, N$_2$ and
(ii) (X$_2$-N$_3$-N$_4$) comprises a second polynucleotide comprising linked nucleotides X$_2$, N$_3$ and N$_4$;
(iii) N$_1$, N$_2$, N$_3$ and N$_4$ each comprise a single nucleotide comprising a nucleoside selected from the group consisting of: adenosine, guanosine, cytidine, 5-methyluridine, uridine and inosine;
(iv) N$_1$ base pairs with N$_4$;
(v) N$_2$ base pairs with N$_3$;
(vi) N$_1$ comprises a 5' diphosphate or triphosphate moiety, or derivative or analog thereof;
(vii) X$_1$ and X$_2$ are each oligonucleotides comprising nucleosides selected from the group consisting of: adenosine, guanosine, cytidine, 5-methyluridine, uridine and inosine;
(viii) X$_1$ is complementary to X$_2$;
(ix) X$_1$ and X$_2$ are each 12 nucleotides to 16 nucleotides in length and are the same length, and;
(x) L is a linker that operably links the first polynucleotide and the second polynucleotide,
wherein N1 and N2 comprise inosine and N3 and N4 comprise cytidine, wherein X1 and X2 are each 12 nucleotides in length, wherein X1 and X2 each comprise at least one inosine nucleoside, wherein the inosine nucleoside base pairs with cytidine in the hairpin RNA, and wherein L comprises a nucleotide linker comprising a tetraloop, wherein the nucleotide sequence of the tetraloop is UUCG.

In some aspects, the disclosure provides an RLR agonist that specifically binds to RLRs, wherein the agonist comprises a blunt-ended, hairpin RNA comprising a non-nucleotide linker, and wherein the agonist comprises the formula:

5'-(N$_1$-N$_2$-X$_1$)-L-(X$_2$-N$_3$-N$_4$)-3', wherein (N$_1$-N$_2$-X$_1$) comprises a first polynucleotide comprising linked nucleotides N$_1$, N$_2$ and X$_1$;
(ii) (X$_2$-N$_3$-N$_4$) comprises a second polynucleotide comprising linked nucleotides X$_2$, N$_3$ and N$_4$;
(iii) N$_1$, N$_2$, N$_3$ and N$_4$ each comprise a single nucleotide comprising a nucleoside selected from the group consisting of: adenosine, guanosine, cytidine, 5-methyluridine, uridine and inosine;
(iv) N$_1$ base pairs with N$_4$;
(v) N$_2$ base pairs with N$_3$;
(vi) N$_1$ comprises a 5' diphosphate or triphosphate moiety, or derivative or analog thereof;
(vii) X$_1$ and X$_2$ are each oligonucleotides comprising nucleosides selected from the group consisting of: adenosine, guanosine, cytidine, 5-methyluridine, uridine and inosine;
(viii) X$_1$ is complementary to X$_2$;
(ix) X$_1$ and X$_2$ are each 12 nucleotides to 16 nucleotides in length and are the same length, and;
(x) L is the non-nucleotide linker that covalently links the first polynucleotide and the second polynucleotide,
wherein N1 and N2 comprise guanosine, wherein N3 and N4 comprise cytidine, wherein X1 and X2 are each 12 nucleotides in length, and wherein the non-nucleotide linker is a C9 alkyl linker.

In some aspects, the disclosure provides an RLR agonist that specifically binds to RLRs, wherein the agonist comprises a blunt-ended, hairpin RNA comprising a non-nucleotide linker, and wherein the agonist comprises the formula:

5'-(N$_1$-N$_2$-X$_1$)-L-(X$_2$-N$_3$-N$_4$)-3', wherein (i) (N$_1$-N$_2$-X$_1$) comprises a first polynucleotide comprising linked nucleotides N$_1$, N$_2$ and X$_1$;
(ii) (X$_2$-N$_3$-N$_4$) comprises a second polynucleotide comprising linked nucleotides X$_2$, N$_3$ and N$_4$;
(iii) N$_1$, N$_2$, N$_3$ and N$_4$ each comprise a single nucleotide comprising a nucleoside selected from the group consisting of: adenosine, guanosine, cytidine, 5-methyluridine, uridine and inosine;
(iv) N$_1$ base pairs with N$_4$;
(v) N$_2$ base pairs with N$_3$;
(vi) N$_1$ comprises a 5' diphosphate or triphosphate moiety, or derivative or analog thereof;
(vii) X$_1$ and X$_2$ are each oligonucleotides comprising nucleosides selected from the group consisting of: adenosine, guanosine, cytidine, 5-methyluridine, uridine and inosine;
(viii) X$_1$ is complementary to X$_2$;
(ix) X$_1$ and X$_2$ are each 12 nucleotides to 16 nucleotides in length and are the same length, and;
(x) L is the non-nucleotide linker that covalently links the first polynucleotide and the second polynucleotide,
wherein N1 and N2 comprise guanosine, wherein N3 and N4 comprise cytidine, wherein X1 and X2 are each 12 nucleotides in length, and wherein the non-nucleotide linker is a hexaethylene glycol linker.

In some aspects, the disclosure provides an RLR agonist that specifically binds to RLR, wherein the 5' most nucleotide of the agonist comprises a 5' diphosphate or triphosphate moiety, or derivative or analog thereof, and wherein the agonist comprises the nucleotide sequence selected from the group consisting of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and 36.

In some aspects, the disclosure provides an RLR agonist that specifically binds to RLRs, wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof, wherein the agonist comprises a sequence motif that provides at least one improved biological activity mediated by the RLR relative to an agonist that does not comprise the sequence motif, and wherein the first polynucleotide and the second polynucleotide comprise the nucleotide sequences selected from the group consisting of:
  (i) SEQ ID NO: 37 and 68, respectively;
  (ii) SEQ ID NO: 38 and 69, respectively;
  (iii) SEQ ID NO: 39 and 70, respectively;
  (iv) SEQ ID NO: 40 and 71, respectively;
  (v) SEQ ID NO: 41 and 72, respectively;
  (vi) SEQ ID NO: 42 and 73, respectively;
  (vii) SEQ ID NO: 43 and 74, respectively;
  (viii) SEQ ID NO: 44 and 75, respectively;
  (ix) SEQ ID NO: 45 and 76, respectively;
  (x) SEQ ID NO: 46 and 77, respectively;
  (xi) SEQ ID NO: 47 and 78, respectively;
  (xii) SEQ ID NO: 48 and 79, respectively;
  (xiii) SEQ ID NO: 49 and 80, respectively;
  (xiv) SEQ ID NO: 50 and 81, respectively;
  (xv) SEQ ID NO: 51 and 82, respectively;
  (xvi) SEQ ID NO: 52 and 83, respectively;
  (xvii) SEQ ID NO: 53 and 84, respectively;
  (xviii) SEQ ID NO: 54 and 85, respectively;
  (xix) SEQ ID NO: 55 and 86, respectively;
  (xx) SEQ ID NO: 56 and 87, respectively;
  (xxi) SEQ ID NO: 57 and 88, respectively;
  (xxii) SEQ ID NO: 58 and 89, respectively;
  (xxiii) SEQ ID NO: 59 and 89, respectively;
  (xxiv) SEQ ID NO: 60 and 90, respectively;
  (xxv) SEQ ID NO: 61 and 91, respectively;
  (xxvi) SEQ ID NO: 62 and 92, respectively;
  (xxvii) SEQ ID NO: 63 and 91, respectively;
  (xxviii) SEQ ID NO: 64 and 93, respectively;
  (xxix) SEQ ID NO: 65 and 94, respectively;
  (xxx) SEQ ID NO: 66 and 95, respectively;
  (xxxi) SEQ ID NO: 67 and 96, respectively; and
  (xxxii) SEQ ID NO: 63 and 97, respectively.

In some aspects, the disclosure provides an RLR agonist that specifically binds to RLRs, wherein the agonist comprises a blunt-ended, hairpin RNA comprising at least one or more nucleotides comprising inosine which base pairs with cytidine, and wherein the agonist comprises the nucleotide sequence selected from the group consisting of SEQ ID NOs: 22, 23 and 25.

In some aspects, the disclosure provides an RLR agonist that specifically binds to RLRs, wherein the agonist comprises a blunt-ended, hairpin RNA comprising at least one or more nucleotides comprising inosine which base pairs with cytidine, wherein the agonist comprises the formula 5'-($N_1$-$N_2$-$X_1$)-L-($X_2$-$N_3$-$N_4$)-3', wherein ($N_1$-$N_2$-$X_1$) comprises a first polynucleotide and ($X_2$-$N_3$-$N_4$) comprises a second polynucleotide, and wherein the first polynucleotide and the second polynucleotide comprise the nucleotide sequences selected from the group consisting of:
  (i) SEQ ID NO: 58 and 89, respectively;
  (ii) SEQ ID NO: 59 and 89, respectively; and
  (iii) SEQ ID NO: 61 and 91, respectively.

In some aspects, the disclosure provides an RLR agonist that specifically binds to RLRs, wherein the agonist comprises a blunt-ended, hairpin RNA comprising a non-nucleotide linker, wherein the agonist comprises the formula 5'-($N_1$-$N_2$-$X_1$)-L-($X_2$-$N_3$-$N_4$)-3', wherein ($N_1$-$N_2$-$X_1$) comprises a first polynucleotide and ($X_2$-$N_3$-$N_4$) comprises a second polynucleotide, and wherein the first polynucleotide and the second polynucleotide comprise the nucleotide sequences selected from the group consisting of:
  (i) SEQ ID NO: 37 and 68, respectively;
  (ii) SEQ ID NO: 38 and 69, respectively;
  (iii) SEQ ID NO: 39 and 70, respectively;
  (iv) SEQ ID NO: 40 and 71, respectively;
  (v) SEQ ID NO: 41 and 72, respectively;
  (vi) SEQ ID NO: 42 and 73, respectively;
  (vii) SEQ ID NO: 43 and 74, respectively;
  (viii) SEQ ID NO: 44 and 75, respectively;
  (ix) SEQ ID NO: 45 and 76, respectively;
  (x) SEQ ID NO: 46 and 77, respectively;
  (xi) SEQ ID NO: 47 and 78, respectively;
  (xii) SEQ ID NO: 48 and 79, respectively;
  (xiii) SEQ ID NO: 49 and 80, respectively;
  (xiv) SEQ ID NO: 50 and 81, respectively;
  (xv) SEQ ID NO: 51 and 82, respectively;
  (xvi) SEQ ID NO: 52 and 83, respectively;
  (xvii) SEQ ID NO: 53 and 84, respectively;
  (xviii) SEQ ID NO: 54 and 85, respectively;
  (xix) SEQ ID NO: 55 and 86, respectively;
  (xx) SEQ ID NO: 56 and 87, respectively;
  (xxi) SEQ ID NO: 57 and 88, respectively;
  (xxii) SEQ ID NO: 58 and 89, respectively;
  (xxiii) SEQ ID NO: 59 and 89, respectively;
  (xxiv) SEQ ID NO: 60 and 90, respectively;
  (xxv) SEQ ID NO: 61 and 91, respectively;
  (xxvi) SEQ ID NO: 62 and 92, respectively;
  (xxvii) SEQ ID NO: 63 and 91, respectively;
  (xxviii) SEQ ID NO: 64 and 93, respectively;
  (xxix) SEQ ID NO: 65 and 94, respectively;
  (xxx) SEQ ID NO: 66 and 95, respectively;
  (xxxi) SEQ ID NO: 67 and 96, respectively; and
  (xxxii) SEQ ID NO: 63 and 97, respectively.

In some embodiments of the RLR agonists provided by the disclosure, the nucleotide sequence comprising the RLR agonist is not complementary to a genomic DNA sequence or mRNA sequence, wherein the RLR agonist does not participate in RNA interference, and wherein the RLR agonist does not silence gene expression.

In some aspects, the disclosure provides a pharmaceutical composition for stimulating an immune response, treating or delaying progression of a cancer, or reducing or inhibiting tumor growth in a subject in need thereof, comprising an RLR agonist provided by the disclosure, and a pharmaceutically acceptable carrier. In some embodiments, the RLR agonist is formulated in a polyethylenimine (PEI) carrier. In some embodiments, the PEI carrier is JetPEI®.

In some aspects, the disclosure provides a method to increase RLR-mediated production of one or more cytokines in a cell, the method comprising contacting the cell with an RLR agonist provided by the disclosure, wherein the RLR agonist increases RLR-mediated cytokine production in a cell. In some embodiments, the RLR agonist increases RLR-mediated type I interferon (e.g., IFN-α, IFN-β) production in a cell. In some embodiments, the RLR agonist increases RLR-mediated IL-1β production in a cell. In some embodiments, the RLR agonist increases RLR-mediated IP-10 production in a cell. In some embodiments, the RLR agonist increases RLR-mediated IL-6, IL-12p70, MCP-1 and/or MIP-1β production in a cell.

In some aspects, the disclosure provides a method to increase RLR-mediated expression of one or more interferon-stimulated genes in a cell, the method comprising contacting the cell with an RLR agonist provided by the disclosure, wherein the agonist increases RLR-mediated expression of one or more interferon-stimulated genes in a cell.

In some aspects, the disclosure provides method to increase RLR-dependent intracellular signaling in a cell, the method comprising contacting the cell with an RLR agonist provided by the disclosure, wherein the agonist increases RLR-dependent intracellular signaling.

In some aspects, the disclosure provides a method of stimulating an immune response in a subject, the method comprising administering to the subject an effective amount of an RLR agonist or a pharmaceutical composition provided by the disclosure.

In some aspects, the disclosure provides a method of treating or delaying progression of a cancer in a subject, the method comprising administering to the subject an effective amount of an RLR agonist or a pharmaceutical composition provided by the disclosure.

In some aspects, the disclosure provides a method of reducing or inhibiting tumor growth in a subject in need thereof, the method comprising administering to the subject an effective amount of an RLR agonist or a pharmaceutical composition provided by the disclosure.

In some aspects, the disclosure provides a method for stimulating an immune response, treating or delaying progression of a cancer, or inhibiting tumor growth in a subject in need thereof, the method comprising administering to the subject an effective amount of an RLR agonist or a pharmaceutical composition provided by the disclosure, wherein the agonist, or the pharmaceutical composition, increases RLR-mediated production of one or more cytokines in a cell, increases RLR-mediated expression of one or more interferon-stimulated genes in a cell, and or increases RLR-dependent intracellular signaling in a cell, thereby stimulating the immune response, treating or delaying progression of the cancer, or inhibiting growth of the tumor.

In some embodiments of the methods provided by the disclosure, an RLR agonist or pharmaceutical composition provided by the disclosure is administered in combination with one or more additional therapeutic agents, wherein the one or more additional therapeutic agents is selected from the group consisting of: a chemotherapy, a targeted anti-cancer therapy, an oncolytic drug, a cell death-inducing agent, an opsonizing agent (e.g., an opsonizing antibody) a cytotoxic agent, an immune-based therapy, a cytokine, an activator or agonist of a costimulatory molecule, an inhibitor of an inhibitory molecule, a vaccine, a cellular immunotherapy, or a combination thereof.

In some embodiments, an RLR agonist or pharmaceutical composition provided by the disclosure is administered preceding or subsequent to administration of the one or more additional therapeutic agents or wherein the one or more additional therapeutic agents is administered concurrently with, preceding or subsequent to the administration of the agonist or pharmaceutical composition.

In some embodiments, the one or more additional therapeutic agents is a PD-1/PD-L1 antagonist, a TIM-3 antagonist, a VISTA antagonist, an adenosine A2AR antagonist, a B7-H3 antagonist, a B7-H4 antagonist, a BTLA antagonist, a CTLA-4 antagonist, an IDO antagonist, a KIR antagonist, a LAG-3 antagonist, a Toll-like receptor 3 (TLR3) agonist, a Toll-like receptor 7 (TLR7) agonist, a Toll-like receptor 9 (TLR9) agonist.

In some embodiments, the one or more additional therapeutic agents is an agonist comprising an polypeptide (e.g., antibody, or antigen binding portion thereof) that specifically binds to CD137 (4-1BB).

In some embodiments, the one or more additional therapeutic agents is an agonist comprising an polypeptide (e.g., antibody, or antigen binding portion thereof) that specifically binds to CD134 (OX40).

In some embodiments, the one or more additional therapeutic agents is a PD-1/PD-L1 antagonist. In some embodiments, the PD-1/PD-L1 antagonist is selected from the group consisting of: PDR001, KEYTRUDA® (pembrolizumab), OPDIVO® (nivolumab), pidilizumab, MEDI0680, REGN2810, TSR-042, PF-06801591, and AMP-224. In some embodiments, the PD-1/PD-L1 antagonist is selected from the group consisting of: FAZ053, TENCENTRIQ® (atezolizumab), BAVENCIO® (avelumab), IMFINZI® (durvalumab), and BMS-936559.

In some embodiments, the one or more additional therapeutic agents is a TIM-3 antagonist.

In some embodiments, the one or more additional therapeutic agents is a VISTA antagonist.

In some embodiments, the one or more additional therapeutic agents is an adenosine A2AR antagonist.

In some embodiments, the one or more additional therapeutic agents is a B7-H3 antagonist.

In some embodiments, the one or more additional therapeutic agents is a B7-H4 antagonist.

In some embodiments, the one or more additional therapeutic agents is a BTLA antagonist.

In some embodiments, the one or more additional therapeutic agents is a CTLA-4 antagonist.

In some embodiments, the one or more additional therapeutic agents is a IDO antagonist.

In some embodiments, the one or more additional therapeutic agents is a KIR antagonist.

In some embodiments, the one or more additional therapeutic agents is a LAG-3 antagonist.

In some embodiments, the one or more additional therapeutic agents is a Toll-like receptor 3 (TLR3) agonist. In some embodiments, the TLR3 agonist is polyinosinic:polycytidylic acid (poly I:C). In some embodiments, the TLR3 agonist is HILTONOL® (poly ICLC). In some embodiments, the TLR3 agonist is polyadenylic-polyuridylic acid (poly A:U). In some embodiments, the TLR3 agonist is RIBOXXIM® (RGIC®100). In some embodiments, the TLR3 agonist is RIBOXXON® (RGIC®50 bioconjugate). In some embodiments, the TLR3 agonist is RIBOXXOL (RGIC®50).

In some embodiments, the one or more additional therapeutic agents is a Toll-like receptor 7 (TLR7) agonist. In some embodiments, the TLR7 agonist is GS-9620 (Vesatolimod). In some embodiments, the TLR7 agonist is imiquimod (ALDARA™). In some embodiments, the TLR7 agonist is resiquimod (R-848).

In some embodiments, the one or more additional therapeutic agents is a Toll-like receptor 9 (TLR9) agonist. In some embodiments, the TLR9 agonist is a CpG oligodeoxynucleotide (CpG ODN). In some embodiments, the CpG ODN is a Class A CpG ODN (CpG-A ODN). In some embodiments, the CpG ODN is a Class B CpG ODN (CpG-B ODN). In some embodiments, the CpG ODN is a Class C CpG ODN (CpG-C ODN).

In some aspects, the disclosure provides a use of an RLR agonist or of a pharmaceutical composition provided by the disclosure, for stimulating an immune response, treating or delaying progression of a cancer, or inhibiting tumor growth in a subject in need thereof, optionally for use in combination with one or more additional therapeutic agents.

In some aspects, the disclosure provides a use of an RLR agonist or a pharmaceutical composition provided by the disclosure, in the manufacture of a medicament for stimulating an immune response, treating or delaying progression of a cancer, or inhibiting tumor growth in a subject in need thereof, optionally for use in combination with one or more additional therapeutic agents.

In some aspects, the disclosure provides a kit comprising an RLR agonist or a pharmaceutical composition provided by the disclosure and instructions for use in stimulating an immune response in a subject, or treating or delaying progression of a cancer, or inhibiting tumor growth in a subject, optionally with instructions for use in combination with one or more additional therapeutic agents.

In some embodiments of a use or a kit provided by the disclosure, an RLR agonist or a pharmaceutical composition provided by the disclosure is administered in combination with one or more additional therapeutic agents, wherein the one or more additional therapeutic agents is selected from the group consisting of: a chemotherapy, a targeted anti-cancer therapy, an oncolytic drug, a cell death-inducing agent, an opsonizing agent (e.g., an opsonizing antibody) a cytotoxic agent, an immune-based therapy, a cytokine, an activator of a costimulatory molecule, an inhibitor of an inhibitory molecule, a vaccine, a cellular immunotherapy, or a combination thereof.

In some embodiments of a use or a kit provided by the disclosure, an RLR agonist or a pharmaceutical composition provided by the disclosure is administered preceding or subsequent to administration of the one or more additional therapeutic agents or wherein the one or more additional therapeutic agents is administered concurrently with, preceding or subsequent to the administration of the agonist or pharmaceutical composition.

In some embodiments of a use or a kit provided by the disclosure, the one or more additional therapeutic agents is a PD-1/PD-L1 antagonist, a TIM-3 antagonist, a VISTA antagonist, an adenosine A2AR antagonist, a B7-H3 antagonist, a B7-H4 antagonist, a BTLA antagonist, a CTLA-4 antagonist, an IDO antagonist, a KIR antagonist, a LAG-3 antagonist, a Toll-like receptor 3 (TLR3) agonist, a Toll-like receptor 7 (TLR7) agonist, a Toll-like receptor 9 (TLR9) agonist.

In some embodiments of a use or kit provided by the disclosure, the one or more additional therapeutic agents is an agonist comprising an polypeptide (e.g., antibody, or antigen binding portion thereof) that specifically binds to CD137 (4-1BB).

In some embodiments of a use or kit provided by the disclosure, the disclosure the one or more additional therapeutic agents is an agonist comprising an polypeptide (e.g., antibody, or antigen binding portion thereof) that specifically binds to CD134 (OX40).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 provides a bar graph depicting the quantification of IFN-a secretion from human PBMC treated with 3 different concentrations of RIG-I-like receptor agonists comprising various modifications.

DETAILED DESCRIPTION

Overview

The RIG-I-like receptors (RLRs) are a family of cytosolic pattern recognition receptors that are essential for detecting viral RNA and initiating the innate immune response. The RLR family includes three members: Retinoic acid-inducible gene I (RIG-I), Melanoma differentiation-associated gene 5 (MDA5), and Laboratory of genetics and physiology 2 (LGP2). These receptors are expressed in both immune and non-immune cell types and regulate signaling pathways that promote the IRF3-, IRF7-dependent expression of type I and type III interferons (IFNs), and the NF-kappa B-dependent expression of pro-inflammatory cytokines.

All three RLR family receptors have a DExD/H box RNA helicase domain with ATPase activity. This domain along with the adjacent C-terminal domain is required for RNA binding. In addition, the C-terminal domains of RIG-I and LGP2 have been shown to act as repressor domains, ensuring that the receptors remain in an inactive conformation until they are bound by an activating RNA.

The present disclosure provides RLR agonists comprising synthetic RNA molecules that fold to form a duplexed, dsRNA and that comprise one or more sequence motifs that provides one or more improved biological activities.

Definitions

Terms used in the claims and specification are defined as set forth below unless otherwise specified. In the case of direct conflict with a term used in a parent provisional patent application, the term used in the instant application shall control.

It must be noted that, as used in the specification and the appended claims, the singular forms "a," "an" and "the" include plural referents unless the context clearly dictates otherwise. Further, unless otherwise required by context, singular terms shall include pluralities and plural terms shall include the singular.

About: As used herein, the term "about" (alternatively "approximately") will be understood by persons of ordinary skill and will vary to some extent depending on the context in which it is used. If there are uses of the term which are not clear to persons of ordinary skill given the context in which it is used, "about" will mean up to plus or minus 10% of the particular value.

Agonist: As used herein, the term "agonist" is used in its broadest sense and encompasses any molecule or compound that partially or fully promotes, induces, increases, and/or activates a biological activity of a native polypeptide disclosed herein. Agonist molecules according to the disclosure may include nucleic acids (e.g., oligonucleotides, polynucleotides), antibodies or antigen-binding fragments, fragments or amino acid sequence variants of native polypeptides, peptides, oligonucleotides, lipids, carbohydrates, and small organic molecules. In some embodiments, activation in the presence of the agonist is observed in a dose-dependent manner. In some embodiments, the measured signal (e.g., biological activity) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% higher than the signal measured with a negative control under comparable conditions. Also disclosed herein, are methods of identifying agonists suitable for use in the methods of the disclosure. For example, these methods include, but are not limited to, binding assays such as enzyme-linked immuno-absorbent assay (ELISA), Forte Bio© systems, fluorescence polarization (FP) assay, and radioimmunoassay (RIA). These assays determine the ability of an agonist to bind the polypeptide of interest (e.g., a receptor or ligand) and therefore indicate the ability of the agonist to promote, increase or activate the activity of the polypeptide. Efficacy of an agonist can also be determined using functional assays, such as the ability of an agonist to activate or promote the function of the polypeptide. For example, a functional assay may comprise contacting a polypeptide with a candidate agonist molecule and measuring a detectable change in one or more biological activities normally associated with the polypeptide. The potency of an agonist is usually defined by its $EC_{50}$ value (concentration required to activate 50% of the agonist response). The lower the $EC_{50}$ value the greater the potency of the agonist and the lower the concentration that is required to activate the maximum biological response.

Ameliorating: As used herein, the term "ameliorating" refers to any therapeutically beneficial result in the treatment of a disease state, e.g., cancer, including prophylaxis, lessening in the severity or progression, remission, or cure thereof.

Amino acid: As used herein, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

Amino acid substitution: As used herein, an "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, larger "peptide insertions," can also be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

Base Composition: As used herein, the term "base composition" refers to the proportion of the total nucleotides of a nucleic acid (e.g., an RNA) consisting of guanine (or hypoxanthine)+cytosine and/or uracil (or thymine)+adenine nucleobases.

Base Pair: As used herein, the term "base pair" refers to two nucleobases on opposite complementary polynucleotide strands, or regions of the same strand, that interact via the formation of specific hydrogen bonds. As used herein, the term "Watson-Crick base pairing", used interchangeably with "complementary base pairing", refers to a set of base pairing rules, wherein a purine always binds with a pyrimidine such that the nucleobase adenine (A) forms a complementary base pair with thymine (T) and guanine (G) forms a complementary base pair with cytosine (C) in DNA molecules. In RNA molecules, thymine is replaced by uracil (U), which, similar to thymine (T), forms a complementary base pair with adenine (A). The complementary base pairs are bound together by hydrogen bonds and the number of hydrogen bonds differs between base pairs. As in known in the art, guanine (G)-cytosine (C) base pairs are bound by three (3) hydrogen bonds and adenine (A)-thymine (T) or uracil (U) base pairs are bound by two (2) hydrogen bonds.

Base pairing interactions that do not follow these rules can occur in natural, non-natural, and synthetic nucleic acids and are referred to herein as "non-Watson-Crick base pairing" or alternatively "non-canonical base pairing". A "wobble base pair" is a pairing between two nucleobases in RNA molecules that does not follow Watson-Crick base pair rules. For example, inosine is a nucleoside that is structurally similar to guanosine, but is missing the 2-amino group. Inosine is able to form two hydrogen bonds with each of the four natural nucleobases (Oda et al., (1991) Nucleic Acids Res 19:5263-5267) and it is often used by researchers as a "universal" base, meaning that it can base pair with all the naturally-occurring or canonical bases. The four main wobble base pairs are the guanine-uracil (G-U) base pair, the hypoxanthine-uracil (I-U) base pair, the hypoxanthine-adenine (I-A) base pair, and the hypoxanthine-cytosine (I-C) base pair. In order to maintain consistency of nucleic acid nomenclature, "I" is used for hypoxanthine because hypoxanthine is the nucleobase of inosine; nomenclature otherwise follows the names of nucleobases and their corresponding nucleosides (e.g., "G" for both guanine and guanosine—as well as for deoxyguanosine). The thermodynamic stability of a wobble base pair is comparable to that of a Watson-Crick base pair. Wobble base pairs play a role in the formation of secondary structure in RNA molecules.

In one aspect, the disclosure provides synthetic RNA molecules that agonize or activate one or more RIG-I-like receptors (RLRs), wherein inosine can only be inserted at positions where it will base pair with cytidine (I-C base pair); that is, inosine can be substituted for guanosine but cannot be substituted for the other nucleosides.

Biologically active: As used herein, the phrase "biologically active" refers to a characteristic of any substance that has activity in a biological system and/or organism. For instance, a substance that, when administered to an organism, has a biological effect on that organism, is considered to be biologically active and thus have "biological activity". In particular embodiments, where a nucleic acid is biologically active, a portion of that nucleic acid that shares at least one biological activity of the whole nucleic acid is typically referred to as a "biologically active" portion.

Covalently linked: As used herein, the term "covalently linked" (alternatively "conjugated", "linked," "attached," "fused", or "tethered"), when used with respect to two or more moieties, means that the moieties are physically associated or connected with one another, by whatever means including chemical conjugation, recombinant techniques or enzymatic activity, either directly or via one or more additional moieties that serves as a linking agent, to form a structure that is sufficiently stable so that the moieties remain physically associated under the conditions in which the structure is used, e.g., physiological conditions.

Complementary: As used herein, the term "complementary" or "complementarity" refers to a relationship between the sequence of nucleotides comprising two polynucleotide strands, or regions of the same polynucleotide strand, and the formation of a duplex comprising the strands or regions, wherein the extent of consecutive base pairing between the two strands or regions is sufficient for the generation of a duplex structure. It is known that adenine (A) forms specific hydrogen bonds, or "base pairs", with thymine (T) or uracil (U). Similarly, it is known that a cytosine (C) base pairs with guanine (G). It is also known that non-canonical nucleobases (e.g., inosine) can hydrogen bond with natural bases. A sequence of nucleotides comprising a first strand of a polynucleotide, or a region, portion or fragment thereof, is said to be "sufficiently complementary" to a sequence of nucleotides comprising a second strand of the same or a different nucleic acid, or a region, portion, or fragment thereof, if, when the first and second strands are arranged in an antiparallel fashion, the extent of base pairing between the two strands maintains the duplex structure under the conditions in which the duplex structure is used (e.g., physiological conditions in a cell). It should be understood that complementary strands or regions of polynucleotides can include some base pairs that are non-complementary. Complementarity may be "partial," in which only some of the nucleobases comprising the polynucleotide are matched according to base pairing rules. Or, there may be "complete" or "total" complementarity between the nucleic acids. Although the degree of complementarity between polynucleotide strands or regions has significant effects on the efficiency and strength of hybridization between the strands or regions, it is not required for two complementary polynucleotides to base pair at every nucleotide position. In some embodiments, a first polynucleotide is 100% or "fully" complementary to a second polynucleotide and thus forms a base pair at every nucleotide position. In some embodiments, a first polynucleotide is not 100% complementary (e.g., is 90%, or 80% or 70% complementary) and contains mismatched nucleotides at one or more nucleotide positions. While perfect complementarity is often desired, some embodiments can include one or more but preferably 6, 5, 4, 3, 2, or 1 mismatches.

Contacting: As used herein, the term "contacting" means establishing a physical connection between two or more entities. For example, contacting a cell with an agent (e.g. an RNA, a lipid nanoparticle composition, or other pharmaceutical composition of the disclosure) means that the cell and the agent are made to share a physical connection. Methods of contacting cells with external entities both in vivo, in vitro, and ex vivo are well known in the biological arts. In exemplary embodiments of the disclosure, the step of contacting a mammalian cell with a composition (e.g., an isolated RNA, nanoparticle, or pharmaceutical composition of the disclosure) is performed in vivo. For example, contacting a lipid nanoparticle composition and a cell (for example, a mammalian cell) which may be disposed within an organism (e.g., a mammal) may be performed by any suitable administration route (e.g., parenteral administration to the organism, including intravenous, intramuscular, intradermal, and subcutaneous administration). For a cell present in vitro, a composition (e.g., a lipid nanoparticle or an isolated RNA) and a cell may be contacted, for example, by adding the composition to the culture medium of the cell and may involve or result in transfection. Moreover, more than one cell may be contacted by an agent.

Denaturation: As used herein, the term "denaturation" refers to the process by which the hydrogen bonding between base paired nucleotides in a nucleic acid is disrupted, resulting in the loss of secondary and/or tertiary nucleic acid structure (e.g. the separation of previously annealed strands). Denaturation can occur by the application of an external substance, energy, or biochemical process to a nucleic acid.

Antigen presenting cell: The term "antigen presenting cell" or "APC" is a cell that displays foreign antigen complexed with MHC on its surface. T cells recognize this complex using T cell receptor (TCR). Examples of APCs include, but are not limited to, dendritic cells (DCs), peripheral blood mononuclear cells (PBMC), monocytes (such as THP-1), B lymphoblastoid cells (such as C1R.A2, 1518 B-LCL) and monocyte-derived dendritic cells (DCs). Some APCs internalize antigens either by phagocytosis or by receptor-mediated endocytosis.

Apoptosis: As used herein, the term "apoptosis" refers to the process of programmed cell death that occurs in multicellular organisms (e.g. humans). The highly-regulated biochemical and molecular events that result in apoptosis can lead to observable and characteristic morphological changes to a cell, including membrane blebbing, cell volume shrinkage, chromosomal DNA condensation and fragmentation, and mRNA decay. A common method to identify cells, including T cells, undergoing apoptosis is to expose cells to a fluorophore-conjugated protein (Annexin V). Annexin V is commonly used to detect apoptotic cells by its ability to bind to phosphatidylserine on the outer leaflet of the plasma membrane, which is an early indicator that the cell is undergoing the process of apoptosis.

Blunt-end: As used herein, the term "blunt-end" "blunt-ended" refers to the structure of an end of a duplexed or double-stranded nucleic acid, wherein both complementary strands comprising the duplex terminate, at least at one end, in a base pair. Hence, neither strand comprising the duplex extends further from the end than the other.

Cancer antigen: As used herein, "cancer antigen" refers to (i) tumor-specific antigens, such as neoantigens, (ii) tumor-associated antigens, (iii) cells that express tumor-specific antigens, (iv) cells that express tumor-associated antigens, (v) embryonic antigens on tumors, (vi) autologous tumor cells, (vii) tumor-specific membrane antigens, (viii) tumor-associated membrane antigens, (ix) growth factor receptors, (x) growth factor ligands, and (xi) any other type of antigen or antigen-presenting cell or material that is associated with a cancer.

Carcinoma: As used herein, the term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The RIG-I-like receptor (RLR) agonists described herein can be used to treat patients who have, who are suspected of having, or who may be at high risk for developing any type of cancer, including renal carcinoma or melanoma. Exemplary carcinomas include those forming from tissue of the cervix, lung, prostate, breast, head and neck, colon and ovary. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

Cytotoxic T lymphocyte (CTL) response: As used herein, the term "cytotoxic T lymphocyte (CTL) response" refers to an immune response induced by cytotoxic T cells. CTL responses are mediated primarily by CD8+ T cells.

Duplex: As used herein, the term "duplex" refers to a structure formed by complementary strands of a double-stranded polynucleotide, or complementary regions of a single-stranded polynucleotide that folds back on itself. The duplex structure of a nucleic acid arises as a consequence of complementary nucleotide sequences being bound together, or hybridizing, by base pairing interactions.

$EC_{50}$: As used herein, the term "$EC_{50}$" refers to the concentration of an agonist which induces a response, either in an in vitro or an in vivo assay, which is 50% of the maximal response, i.e., halfway between the maximal response and the baseline.

Effective dose: As used herein, the term "effective dose" or "effective dosage" is defined as an amount sufficient to achieve or at least partially achieve the desired effect.

Hairpin RNA: As used herein, the term "hairpin RNA" or "RNA hairpin" refers to a self-complementary RNA comprising a double-stranded RNA (dsRNA) stem comprised of complementary nucleotide strands that base pair to form a duplex that terminates at one end in a nucleotide linker comprising a loop of unpaired nucleotides (e.g., a tetraloop) comprising unpaired nucleotides or in a non-nucleotide linker comprising a flexible chemical moiety (e.g., ethylene glycol), either of which connects the complementary nucleotide strands. RNA hairpins may differ in the length of the stem, the size and/or composition of the loop and/or linker, the number of base pair mismatches within the stem, and in the actual nucleotide sequence. RNA hairpins may provide one or more functions, including, but not limited to, guiding the overall folding of an RNA molecule comprising the hairpin, determining interactions in a ribozyme, protecting messenger RNA (e.g., mRNA) from degradation, serving as a recognition motif or structure for RNA binding proteins and acting as a substrate for enzymatic reactions. Further description of RNA hairpin structures and functions can be found in Svoboda and Di Cara (2006) Cell Mol Life Sci 63(7-8):901-908, and references contained therein. In some embodiments, the stem regions of the hairpin RNAs comprising the RLR agonists provided by the disclosure terminate in a blunt end with a 5' triphosphate or diphosphate.

In need: As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with a composition comprising a RIG-I-like receptor agonist).

Linker: As used herein, the term "linker" (alternatively "tether" or "spacer") refers to a moiety that covalently connects, attaches or couples two polynucleotide strands or regions together. As used herein, a linker comprising nucleotides is referred to as a "nucleotide linker" (e.g. a tetraloop). As used herein, the term "non-nucleotide linker" refers to a linker comprising a chemical moiety and that does not comprise a nucleotide. Non-limiting examples of non-nucleotide linkers include linkers comprising ethylene glycol (e.g. hexaethylene glycol), alkyl chains (e.g. C9 alkyl linker), and stilbene diether. Further description of linkers can be found in Paredes et al., (2011) Methods 54:251-259, which is incorporated herein by reference in its entirety.

LGP2: As used herein, the term "LGP2" refers to the Laboratory of Genetics and Physiology 2 polypeptide, a specific member of the RIG-I-like receptor family and is encoded by the DHX58 gene in humans. Alternative names and acronyms for LGP2 in the art include DHX58, D11LGP2, D11lgp2e, and RLR-3. An exemplary amino acid sequence of full-length human LGP2 is set forth in Table 4 (SEQ ID NO: 100) and here:

```
(NCBP Accession Number: NP_077024.2)
MELRSYQWEVIMPALEGKNIIIWLPTGAGKTRAAAYVAKRHLETVDGAKV

VVLVNRVHLVTQHGEEFRRMLDGRWTVTTLSGDMGPRAGFGHLARCHDLL

ICTAELLQMALTSPEEEEHVELTVFSLIVVDECHHTHKDTVYNVIMSQYL

ELKLQRAQPLPQVLGLTASPGTGGASKLDGAINHVLQLCANLDTWCIMSP

QNCCPQLQEHSQQPCKQYNLCHRRSQDPFGDLLKKLMDQIHDHLEMPELS

RKFGTQMYEQQVVKLSEAAALAGLQEQRVYALHLRRYNDALLIHDTVRAV

DALAALQDFYHREHVTKTQILCAERRLLALFDDRKNELAHLATHGPENPK

LEMLEKILQRQFSSSNSPRGIIFTRTRQSAHSLLLWLQQQQGLQTVDIRA

QLLIGAGNSSQSTHMTQRDQQEVIQKFQDGTLNLLVATSVAEEGLDIPHC

NVVVRYGLLTNEISMVQARGRARADQSVYAFVATEGSRELKRELINEALE

TLMEQAVAAVQKMDQAEYQAKIRDLQQAALTKRAAQAAQRENQRQQFPVE

HVQLLCINCMVAVGHGSDLRKVEGTHHVNVNPNFSNYYNVSRDPVVINKV

FKDWKPGGVISCRNCGEVWGLQMIYKSVKLPVLKVRSMLLETPQGRIQAK

KWSRVPFSVPDFDFLQHCAENLSDLSLD
```

Local administration: As used herein, "local administration" or "local delivery," refers to delivery that does not rely upon transport of the composition or agent to its intended target tissue or site via the vascular system. For example, the composition may be delivered by injection or implantation of the composition or agent or by injection or implantation of a device containing the composition or agent. Following local administration in the vicinity of a target tissue or site, the composition or agent, or one or more components thereof, may diffuse to the intended target tissue or site.

MDA5: As used herein, the term "MDA5" refers to the Melanoma Differentiation-Associated Protein 5 polypeptide, a specific member of the RIG-I-like receptor family and is encoded by the IFIH1 gene in humans. Alternative names and acronyms for MDA5 in the art include AGS7, Hlcd, IDDM19, MDA-5, RLR-2, SGMRT1, and interferon induced with helicase C domain 1. An exemplary amino acid sequence of full-length human MDA5 is set forth in Table 4 (SEQ ID NO: 99) and here:

```
(NCBI Accession Number: NP_071451.2)
MSNGYSTDENFRYLISCFRARVKMYIQVEPVLDYLTFLPAEVKEQIQRTV

ATSGNMQAVELLLSTLEKGVWHLGWTREFVEALRRTGSPLAARYMNPELT

DLPSPSFENAHDEYLQLLNLLQPTLVDKLLVRDVLDKCMEEELLTIEDRN
```

-continued

```
RIAAAENNGNESGVRELLKRIVQKENWFSAFLNVLRQTGNNELVQELTGS

DCSESNAEIENLSQVDGPQVEEQLLSTTVQPNLEKEVWGMENNSSESSFA

DSSVVSESDTSLAEGSVSCLDESLGHNSNMGSDSGTMGSDSDEENVAARA

SPEPELQLRPYQMEVAQPALEGKNIICLPTGSGKTRVAVYIAKDHLDKK

KKASEPGKVIVLVNKVLLVEQLFRKEFQPFLKKWYRVIGLSGDTQLKISF

PEVVKSCDIIISTAQILENSLLNLENGEDAGVQLSDFSLIIIDECHHTNK

EAVYNNIMRHYLMQKLKNNRLKKENKPVIPLPQILGLTASPGVGGATKQA

KAEEHILKLCANLDAFTIKTVKENLDQLKNQIQEPCKKFAIADATREDPF

KEKLLEIMTRIQTYCQMSPMSDFGTQPYEQWAIQMEKKAAKEGNRKERVC

AEHLRKYNEALQINDTIRMIDAYTHLETFYNEEKDKKFAVIEDDSDEGGD

DEYCDGDEDEDDLKKPLKLDETDRFLMTLFFENNKMLKRLAENPEYENEK

LTKLRNTIMEQYTRTEESARGIIFTKTRQSAYALSQWITENEKFAEVGVK

AHHLIGAGHSSEFKPMTQNEQKEVISKFRTGKINLLIATTVAEEGLDIKE

CNIVIRYGLVTNEIAMVQARGRARADESTYVLVAHSGSGVIEHETVNDFR

EKMMYKAIHCVQNMKPEEYAHKILELQMQSIMEKKMKTKRNIAKHYKNNP

SLITFLCKNCSVLACSGEDIHVIEKMHHVNMTPEFKELYIVRENKALQKK

CADYQINGEIICKCGQAWGTMMVHKGLDLPCLKIRNFVVVFKNNSTKKQY

KKWVELPITFPNLDYSECCLFSDED
```

Modified: As used herein "modified" or "modification" refers to a changed state or change in structure resulting from a modification of a polynucleotide, e.g., RNA. Polynucleotides may be modified in various ways including chemically, structurally, and/or functionally. For example, the RNA molecules of the present disclosure may be modified by the incorporation of a non-natural base or a sequence motif, comprising a functional sequence or secondary structure, that provides a biological activity. In one embodiment, the RNA is modified by the introduction of non-natural or chemically-modified bases, nucleosides and/or nucleotides, e.g., as it relates to the natural ribonucleotides A, U, G, and C.

Naturally-occurring: As used herein, the term "naturally-occurring" as applied to an object refers to the fact that an object can be found in nature. For example, a polypeptide or polynucleotide sequence, or components thereof such as amino acids or nucleotides, that is present in an organism (including viruses) that can be isolated from a source in nature and which has not been intentionally modified by man in the laboratory is naturally-occurring.

Nucleic acid: As used herein, the term "nucleic acid" refers to deoxyribonucleotides or ribonucleotides and polymers or oligomers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Polymers of nucleotides are referred to as "polynucleotides". Exemplary nucleic acids or polynucleotides of the disclosure include, but are not limited to, ribonucleic acids (RNAs), deoxyribonucleic acids (DNAs), DNA-RNA hybrids, RNAi-inducing agents, RNAi agents, siRNAs, shRNAs, miRNAs, antisense RNAs, ribozymes, catalytic DNA, RNAs that induce triple helix formation, threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

Polynucleotides used herein can be composed of any polyribonucleotide or polydeoxribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases. "Modified nucleosides" include, for example, as inosine and thymine, when the latter is found in or comprises RNA. A variety of modifications can be made to DNA and RNA; thus, "polynucleotide" embraces chemically, enzymatically, or metabolically modified forms.

Nucleic Acid Structure: As used herein, the term "nucleic acid structure" refers to the arrangement or organization of atoms, chemical constituents, elements, motifs, and/or sequence of nucleobases that comprise a nucleic acid (e.g. an RNA) and/or can refer to the two-dimensional or three-dimensional state of a nucleic acid. Accordingly, the term "RNA structure" refers to the arrangement or organization of atoms, chemical constituents, elements, motifs, and/or sequence of nucleobases comprising an RNA molecule (e.g. an mRNA) and/or can refer to the two-dimensional and/or three dimensional state of an RNA molecule. Nucleic acid structure can be further demarcated into four organizational categories referred to herein as "molecular structure", "primary structure", "secondary structure", and "tertiary structure" based on increasing organizational complexity.

Nucleobase: As used herein, the term "nucleobase" (alternatively "nucleotide base" or "nitrogenous base") refers to a purine or pyrimidine heterocyclic compound found in nucleic acids, including any derivatives or analogs of the naturally occurring purines and pyrimidines that confer improved properties (e.g. binding affinity, nuclease resistance, chemical stability) to a nucleic acid or a portion or segment thereof. Adenine, cytosine, guanine, thymine, and uracil are the primary or canonical nucleobases predominately found in natural nucleic acids. Other natural, non-natural, non-canonical and/or synthetic nucleobases, can be incorporated into nucleic acids, such as those disclosed herein.

Nucleoside/Nucleotide: As used herein, the term "nucleoside" refers to a compound containing a sugar molecule (e.g., a ribose in RNA or a deoxyribose in DNA), or derivative or analog thereof, covalently linked to a nucleobase (e.g., a purine or pyrimidine), or a derivative or analog thereof (also referred to herein as "nucleobase"). As used herein, the term "nucleotide" refers to a nucleoside covalently linked to a phosphate group. As used herein, the term "ribonucleoside" refers to a nucleoside that comprise a ribose and a nucleobase (e.g., adenosine (A), cytidine (C), guanosine (G), 5-methyluridine ($m^5U$), uridine (U), or inosine (I)).

Operably linked: As used herein, a nucleic acid, or fragment or portion thereof, such as a polynucleotide or oligonucleotide is "operably linked" when it is placed into a functional relationship with another nucleic acid sequence, or fragment or portion thereof.

Polynucleotide/oligonucleotide: As used herein, the terms "polynucleotide" and "oligonucleotide" are used interchangeably and refer to a single-stranded or double-stranded polymer or oligomer of nucleotides or nucleoside monomers consisting of naturally-occurring bases, sugars and inter-sugar (backbone) linkages. The terms "polynucleotide" and "oligonucleotide" also includes polymers and oligomers comprising non-naturally occurring bases, sugars and inter-sugar (backbone) linkages, or portions thereof, which function similarly. Polynucleotides are not limited to any particular length of nucleotide sequence, as the term "polynucleotides" encompasses polymeric forms of nucleotides of any length. Short polynucleotides are typically referred to in the art as "oligonucleotides". In the context of the present disclosure, such modified or substituted polynucleotides and oligonucleotides are often preferred over native forms because the modification increases one or more desirable or beneficial biological properties or activities including, but not limited to, increased cytokine production, enhanced cellular uptake and/or increased stability in the presence of nucleases. In some embodiments, the agonists of the disclosure comprise polynucleotides and oligonucleotides that contain at least one region of modified nucleotides that confers one or more beneficial properties or increases biological activity (e.g., increased nuclease resistance, increased uptake into cells, increased duplex stability, increased binding affinity to a target polypeptide).

Palindromic sequence: As used herein, the term "palindromic sequence" (alternatively "palindrome") refers to a sequence of nucleotides that is self-complementary; wherein the sequence of nucleotides in the 5' to 3' direction is the same as the sequence of nucleotides comprising the complementary strand, when read in the 5' to 3'. For example, the sequence 5'-ACCTAGGT-3' is a palindromic sequence because its complementary sequence, 3'-TGGATCCA-5', when read in the 5' to 3' direction, is the same as the original sequence. In contrast, the sequence 5'-AGTGGCTG-3' is not a palindromic sequence because its complementary sequence, 3'-TCACCGAC-5', when read in the 5' to 3' direction, is not the same as the original sequence.

In one embodiment, the agonist is comprised of a first oligonucleotide, wherein the sequence of the first oligonucleotide is a palindromic sequence. In another embodiment, the agonist is comprised of a first oligonucleotide, wherein the first oligonucleotide comprises a palindromic sequence.

Palindromic sequences in preferred oligonucleotides of the invention preferably include both the 5' end of the oligonucleotide and the 3' end of the oligonucleotide, thus forming a blunt end. In one embodiment of the invention the oligonucleotide comprises a single palindromic sequence and in another more preferred embodiment of the invention the oligonucleotide comprises two complementary palindromes interrupted by an intervening sequence, spacer, or linker that connects the 2 palindromes within 1 or 2 different oligonucleotides so as to form a hairpin duplex with a blunt end.

Parenteral administration: As used herein, "parenteral administration," "administered parenterally," and other grammatically equivalent phrases, refer to modes of administration other than enteral and topical administration, usually by injection, and include, without limitation, intravenous, intranasal, intraocular, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

Patient: As used herein, the term "patient" includes human and other mammalian subjects that receive either prophylactic or therapeutic treatment.

Percent identity: As used herein, the term "percent identity," in the context of two or more nucleic acid or polypeptide sequences, refers to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausub el et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website. The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and)(BLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. See http://www.ncbi.nlm.nih.gov.

Pharmaceutically acceptable: As used herein, the term "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

Pharmaceutically acceptable carrier: As used herein, the term "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) J Pharm Sci 66:1-19).

Phosphate: The term "phosphate" as used herein means a salt or ester of phosphoric acid. Polyphosphates are salts or esters of polymeric oxyanions formed from tetrahedral $PO_4$ (phosphate) structural units linked together by sharing oxygen atoms. As used herein, the term "diphosphate" refers to a polyphosphate comprising two phosphate structural units. As used herein, the term "triphosphate" refers to a polyphosphate comprising three phosphate structural units. In some embodiments, the disclosure provides a RIG-I-like receptor agonist comprising a diphosphate moiety, or a derivative or analog thereof, linked to the 5' terminus. In some embodiments, the disclosure provides a RIG-I-like receptor agonist comprising a triphosphate moiety, or a derivative or analog thereof, linked to the 5' terminus. In some embodiments, the derivative or analog thereof is a phosphate bioisostere.

Phosphate bioisostere: As used herein, the term "phosphate bioisostere" (alternatively "phosphate mimic") refers to chemical substituents or groups with similar physical or chemical properties to phosphate and which produce broadly similar biological properties to phosphate, including biphosphate and triphosphate moieties. In drug design, the purpose of exchanging one bioisostere for another is to enhance the desired biological or physical properties of a compound without making significant changes in chemical structure. The use of bioisosteres is widespread in drug development and is used, for example, to reduce toxicity, change bioavailability, or modify the activity or metabolism of the parental or lead compound (see e.g., Rye and Baell (2005) Curr Med Chem 12(26):3127-3141; Elliot et al., (2012) MedChemCom 3(7):735-751, which are incorporated herein by reference in their entirety).

Polypeptide: As used herein, the terms "polypeptide," "peptide", and "protein" are used interchangeably to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

Preventing: As used herein, the term "preventing" when used in relation to a condition, refers to administration of a composition which reduces the frequency of, or delays the onset of, symptoms of a medical condition in a subject relative to a subject which does not receive the composition.

Purified: As used herein, the term "purified" or "isolated" as applied to any of the proteins (antibodies or fragments) described herein refers to a polypeptide that has been separated or purified from components (e.g., proteins or other naturally-occurring biological or organic molecules) which naturally accompany it, e.g., other proteins, lipids, and nucleic acid in a prokaryote expressing the proteins. Typically, a polypeptide is purified when it constitutes at least 60 (e.g., at least 65, 70, 75, 80, 85, 90, 92, 95, 97, or 99) %, by weight, of the total protein in a sample.

Reference ligand: As used herein, the term "reference ligand" (used interchangeably with "reference agonist") or "reference molecule" refers to a RIG-I-like receptor ligand and is used to establish a relationship between itself and one or more distinct RIG-I-like receptor ligands, wherein the relationship is the relative agonistic effect of the reference ligand and the one or more distinct RIG-I-like receptor ligands. As used herein, the term connotes a RIG-I-like receptor ligand or agonist that is useful in a test or assay, such as those described herein, (e.g., an IFN induction assay), as a competitor, wherein the assay is useful for the discovery, identification or development, of one or more distinct agonists that bind to RIG-I-like receptors.

RIG-I: As used herein, the term "RIG-I" refers to the Retinoic Acid-Inducible Gene I polypeptide, a specific member of the RIG-I-like receptor family and is encoded by the DDX58 gene in humans. Alternative names and acronyms for RIG-I in the art include DEAD box polypeptide 58, RIGI, RLR-1, SGMRT2, and DEXD/H-box helicase 58. An exemplary amino acid sequence of full-length human RIG-I is set forth in Table 4 (SEQ ID NO: 98) and here:

```
(NCBI Accession Number: NP_055129.2)
MTTEQRRSLQAFQDYIRKTLDPTYILSYMAPWFREEEVQYIQAEKNNKGP

MEAATLFLKFLLELQEEGWFRGFLDALDHAGYSGLYEAIESWDFKKIEKL

EEYRLLLKRLQPEFKTRIIPTDIISDLSECLINQECEEILQICSTKGMMA

GAEKLVECLLRSDKENWPKTLKLALEKERNKFSELWIVEKGIKDVETEDL

EDKMETSDIQIFYQEDPECQNLSENSCPPSEVSDTNLYSPFKPRNYQLEL

ALPAMKGKNTIICAPTGCGKTFVSLLICEHHLKKFPQGQKGKVVFFANQI

PVYEQQKSVFSKYFERHGYRVTGISGATAENVPVEQIVENNDIIILTPQI
```

-continued

```
LVNNLKKGTIPSLSIFTLMIFDECHNTSKQHPYNMIMFNYLDQKLGGSSG

PLPQVIGLTASVGVGDAKNTDEALDYICKLCASLDASVIATVKHNLEELE

QVVYKPQKFFRKVESRISDKFKYIIAQLMRDTESLAKRICKDLENLSQIQ

NREFGTQKYEQWIVTVQKACMVFQMPDKDEESRICKALFLYTSHLRKYND

ALIISEHARMKDALDYLKDFFSNVRAAGFDEIEQDLTQRFEEKLQELESV

SRDPSNENPKLEDLCFILQEEYHLNPETITILFVKTRALVDALKNWIEGN

PKLSFLKPGILTGRGKTNQNTGMTLPAQKCILDAFKASGDHNILIATSVA

DEGIDIAQCNLVILYEYVGNVIKMIQTRGRGRARGSKCFLLTSNAGVIEK

EQINMYKEKMMNDSILRLQTWDEAVFREKILHIQTHEKFIRDSQEKPKPV

PDKENKKLLCRKCKALACYTADVRVIEECHYTVLGDAFKECFVSRPHPKP

KQFSSFEKRAKIFCARQNCSHDWGIHVKYKTFEIPVIKIESFVVEDIATG

VQTLYSKWKDFHFEKIPFDPAEMSK
```

RIG-I-like receptor: As used herein, the term "RIG-I-like receptor" (abbreviate as "RLR") refers to any member of a family of DExD/H box RNA helicases that function as cytoplasmic pattern recognition sensors of pathogen-associated molecular patterns (PAMPs) typically found in viral RNA. Upon ligand binding, RLRs signal downstream transcription factor activation to drive type 1 interferon (IFN) production and antiviral gene expression that elicits an intracellular immune response to control virus infection. Three RLR members have been identified: RIG-I (retinoic acid-inducible gene I), MDA5 (melanoma differentiation associated factor 5), and LGP2 (laboratory of genetics and physiology 2 and a homolog of mouse D11lgp2) (Loo and Gale (2011) Immunity 34(5):680-692).

RIG-I-like receptor agonist: As used herein, the term "RIG-I-like receptor agonist" (used interchangeably with the term "RLR agonist") refers to a nucleic acid (e.g., an RNA) that binds to RIG-I-like receptors (RLRs) and partially or fully promotes, induces, increases, and/or activates a biological activity, response, and/or downstream pathway(s) mediated by RLR signaling or other RLR-mediated function. Examples of RIG-I-receptor agonists are provided herein.

Stable RNA secondary structure: As used herein, the term "stable RNA secondary structure" refers to a structure, fold, or conformation adopted by an RNA molecule, or local segment or portion thereof, that is persistently maintained under physiological conditions and characterized by a low free energy state. Typical examples of stable RNA secondary structures include duplexes, hairpins, and stem-loops. Stable RNA secondary structures are known in the art to exhibit various biological activities. The term "stable" as used in reference to a polynucleotide duplex, means that the duplex remains hybridized, structured or annealed essentially exclusively in the form of a duplex under physiological conditions or under typical salt and temperature conditions used in nucleic acid diagnostic or therapeutic applications.

Subject: As used herein, the term "subject" includes any human or non-human animal. For example, the methods and compositions of the present invention can be used to treat a subject with an immune disorder. The term "non-human animal" includes all vertebrates, e.g., mammals and non-mammals, such as non-human primates, sheep, dog, cow, chickens, amphibians, reptiles, etc.

T cell: The term "T cell" refers to a type of white blood cell that can be distinguished from other white blood cells by the presence of a T cell receptor on the cell surface. There are several subsets of T cells, including, but not limited to, T helper cells (a.k.a. TH cells or CD4+ T cells) and subtypes, including TH1, TH2, TH3, TH17, TH9, and TFH cells, cytotoxic T cells (a.k.a TC cells, CD8+ T cells, cytotoxic T lymphocytes, T-killer cells, killer T cells), memory T cells and subtypes, including central memory T cells (TCM cells), effector memory T cells (TEM and TEMRA cells), and resident memory T cells (TRM cells), regulatory T cells (a.k.a. Treg cells or suppressor T cells) and subtypes, including CD4+ FOXP3+ Treg cells, CD4+FOXP3-Treg cells, Tr1 cells, Th3 cells, and Treg17 cells, natural killer T cells (a.k.a. NKT cells), mucosal associated invariant T cells (MAITs), and gamma delta T cells (γδ T cells), including Vγ9/Vδ2 T cells. Any one or more of the aforementioned or unmentioned T cells may be the target cell type for a method of use of the invention.

T cell activation: As used herein, the term "T cell activation" or "activation of T cells" refers to a cellular process in which mature T cells, which express antigen-specific T cell receptors on their surfaces, recognize their cognate antigens and respond by entering the cell cycle, secreting cytokines or lytic enzymes, and initiating or becoming competent to perform cell-based effector functions. T cell activation requires at least two signals to become fully activated. The first occurs after engagement of the T cell antigen-specific receptor (TCR) by the antigen-major histocompatibility complex (MEW), and the second by subsequent engagement of co-stimulatory molecules (e.g., CD28). These signals are transmitted to the nucleus and result in clonal expansion of T cells, upregulation of activation markers on the cell surface, differentiation into effector cells, induction of cytotoxicity or cytokine secretion, induction of apoptosis, or a combination thereof.

T cell-mediated response: As used herein, the term "T cell-mediated response" refers to any response mediated by T cells, including, but not limited to, effector T cells (e.g., CD8+ cells) and helper T cells (e.g., CD4+ cells). T cell mediated responses include, for example, T cell cytotoxicity and proliferation.

Tetraloop: As used herein, the term "tetraloop" refers to a type of four-base loop motif found in hairpin or stem-loop RNA secondary structures that cap duplexes at one end, linking the two strands comprising the duplex, and provide stability to the hairpin structure.

Therapeutic agent: As used herein, the term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the terms "therapeutically effective amount" or "therapeutically effective dose," or similar terms used herein are intended to mean an amount of an agent (e.g., a synthetic RIG-I-like receptor agonist) that will elicit the desired biological or medical response, such as, for example, curing or at least partially arresting the condition or disease and its complications in a patient already suffering from the disease (e.g., an improvement in one or more symptoms of a cancer). Amounts effective for this use will depend on the severity of the disorder being treated and the general state of the patient's own immune system.

Treat: The terms "treat," "treating," and "treatment," as used herein, refer to therapeutic or preventative measures described herein. The methods of "treatment" employ administration to a subject, in need of such treatment, a human antibody of the present disclosure, for example, a subject in need of an enhanced immune response against a particular antigen or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

Tumor microenvironment: As used herein, the term "tumor microenvironment" (alternatively "cancer microenvironment"; abbreviated TME) refers to the cellular environment or milieu in which the tumor or neoplasm exists, including surrounding blood vessels as well as non-cancerous cells including, but not limited to, immune cells, fibroblasts, bone marrow-derived inflammatory cells, and lymphocytes. Signaling molecules and the extracellular matrix also comprise the TME. The tumor and the surrounding microenvironment are closely related and interact constantly. Tumors can influence the microenvironment by releasing extracellular signals, promoting tumor angiogenesis and inducing peripheral immune tolerance, while the immune cells in the microenvironment can affect the growth and evolution of tumor cells.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Equivalents and Scope

Those skilled in the art will recognize, or be able to ascertain using no more than routine experimentation, many equivalents to the specific embodiments, described herein. The scope of the present disclosure is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process. Furthermore, it is to be understood that the disclosure encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein.

It is also noted that the term "comprising" is intended to be open and permits but does not require the inclusion of additional elements or steps. When the term "comprising" is used herein, the term "consisting of" is thus also encompassed and disclosed Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

RIG-I-Like Receptors and Their Ligands

The present disclosure provides synthetic RNA ligands that specifically bind to RIG-I-like receptors (RLRs) and agonize RLRs (RLR agonists). In some aspects, the disclosure provides RLR agonists that are useful for the treatment of cancer. In some aspects, the disclosure provides RLR agonists that are useful for the treatment of infectious disease. In some embodiments, the RLR agonists induce cytokine production. In some embodiments, the RLR agonists increase the number of CD8+ T cells in the tumor microenvironment. In some embodiments, the RLR agonists induce protective anti-tumor immunity RIG-I-like receptors (RLRs) comprise a family of DExD/H box RNA helicases that function as cytosolic pattern recognition receptors (PRRs) that sense the presence of pathogenic agents via the recognition of pathogen-associated molecular patterns (PAMPs). In particular, the intracellular presence of non-self (e.g., viral) RNA is sensed by an infected cell via binding of the RNA to RLRs and results in the initiation and modulation of antiviral immunity. Like most viral RNAs, endogenous mRNA and RNA polymerase III transcripts are also 5'-triphosphorylated, but eukaryotic mRNAs possess a 5' cap structure linked to a guanosine methylated at N7 that prevents RIG-I activation. These structural differences between viral and self RNAs, together with differences in intracellular localization, are thought to enable the effective function of RIG-I as a defense against viral infection by the preferential detection of viral RNA. The molecular recognition and binding of non-self RNA ligands to RLRs propagates specific intracellular signal events culminating in the activation of transcription factors that drive type 1 interferon (IFN) production and antiviral gene expression. The RLR-mediated induction of IFN and inflammatory cytokines production as well as antiviral gene expression elicits an immune response to control virus infection (Yoneyama et al., (2015) Curr Opin Immunol 32:48-53).

Three RLR family members have been identified: RIG-I (retinoic acid-inducible gene I)—the founding member and best characterized of RLR family, MDA5 (melanoma differentiation associated factor 5), and LGP2 (laboratory of genetics and physiology 2 and a homolog of mouse D11lgp2). RIG-I is an important component of the innate immune system and plays a critical role in the defense against infection by RNA viruses. In contrast to the Toll-like receptors TLR3, TLR7, TLR8, and TLR9, that detect nucleic acids in the endosomes of a subset of immune cells, RIG-I is a cytosolic innate immune receptor that is expressed in all cell types (Kato et al., (2006) Nature 441(7089):101-105; Loo et al., (2008) J Virol 82(1):335-345). Two early studies independently established that RIG-I specifically detects and is activated by viral RNAs (Hornung et al., (2006) Science 314(5801):994-997; Pichlmair et al., (2006) Science 314 (5801):997-1001).

High-resolution structures of RIG-I/ligand complexes have provided the molecular detail of RIG-I binding to RNA ligands, specifically to the activating ligand, double-stranded 5'-triphosphorylated RNA (ppp-dsRNA) (Civril et al., (2011) EMBO Reports 12(11):1127-1134; Jiang et al., (2011) Nature 479(7373):423-427; Kowalinski et al., (2011) Cell 147(2):423-435; Lu et al., (2010) Structure 18(8): 1032-1043; Luo et al., (2011) Cell 147(2) 409-422; Wang et al., (2010) Nature Structural & Molecular Biology 17(7): 781-787; Hornung et al., (2006) Science 314(5801):994-997; Pichlmair et al., (2006) Science 314(5801):997-1001; Schlee et al., (2009) Immunity 31(1):25-34).). The crystal structures of RIG-I RNA complexes show protein binding to the backbone, not the bases, suggesting that the RNA sequence may not affect RIG-I binding or that RNA sequence may exhibit as of yet uncharacterized effects or activity. To date, evidence for sequence-dependent differential interaction or affinity with, and activation of, RIG-I-like receptors is not described in the art (Schlee and Hartmann (2010) Molecular Therapy 18(7): 1254-1262).

Accordingly, the disclosure provides synthetic RIG-I-like receptor (RLR) agonists comprising non-naturally occurring, synthetic, and or engineered RLR RNA ligands. In some aspects, the disclosure provides an RLR agonist that specifically binds to a RIG-I-like receptor (RLR), wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof, and wherein the agonist comprises a sequence motif that provides at least one improved biological activity mediated by the RLR relative to an agonist that does not comprise the sequence motif.

In some embodiments, the RLR agonists of the disclosure comprise a sequence motif, wherein the sequence motif is selected from the group consisting of:
(i) a GT-repeat motif;
(ii) a GA-repeat motif;
(iii) a AUCG-repeat motif;
(iv) an AU-repeat motif;
(v) a dipyrimidine motif;
(vi) a dipurine motif;
(vii) a pyrimidine triplet motif;
(viii) a purine triplet motif;
(ix) a palindromic sequence motif; and
(x) a combination of any of (i)-(ix).

In some embodiments, the RLR agonists of the disclosure comprise at least one improved biological activity, wherein the improved biological activity is selected from:
(i) an increase in RLR-mediated cytokine production;
(ii) an increase in RLR-mediated expression of interferon-stimulated genes;
(iii) an increase in RLR-mediated intracellular signaling;
(iv) an increase in binding affinity to RLRs; and
(v) a combination of any of (i)-(iv).

In some embodiments, the RLR agonists of the disclosure comprise a sequence motif, wherein the sequence motif is a GT-repeat motif comprises a sequence of <19, about 15-18, about 15, about 10-15, about 10, about 5-10, about 5, about 4 about 18, 17, 16, 15, 14, 13, 12, 11, 10, 9, 8, 7, 6, 5, or 4 guanine and thymine nucleotides, or derivatives or analogs thereof. In some embodiments, the GT-repeat motif is $[GT]_n$, wherein n=2 to 9. In some embodiments, the GT-repeat motif is $[GT]_7$. In some embodiments, the GT-repeat motif is $[GT]_3$, and wherein the GT-repeat motif is followed by a purine triplet and UCG, respectively. In some embodiments, the purine triplet is GGA.

In some embodiments, the sequence motif is a GA-repeat motif comprises a sequence of <19, about 15-18, about 15, about 10-15, about 10, about 5-10, about 5, about 4 about 18, 17, 16, 15, 14, 13, 12, 11, 10, 9, 8, 7, 6, 5, or 4 guanine and adenine nucleotides, or derivatives or analogs thereof. In some embodiments, the GA-repeat motif is $[GA]_n$, where n=2 to 9. In some embodiments, the GA-repeat motif is $[GA]_7$.

In some embodiments, the RLR agonists of the disclosure comprise a sequence motif, wherein the sequence motif is a AUCG-repeat motif comprising a sequence of <19, about 16, about 12-16, about 12, about 8-12, about 6, about 16, 12, 8 adenine, uracil, cytosine, and guanine nucleotides, or derivatives or analogs thereof.

In some embodiments, the AUCG-repeat motif is $[AUCG]_n$, where n=2 to 4. In some embodiments, the AUCG-repeat motif is $[AUCG]_3$.

In some embodiments, the AUCG-repeat motif is preceded by a CG or a dipyrimidine motif. In some embodiments, the AUCG-repeat motif is preceded by a CG. In some embodiments, the dipyrimidine motif is CC. In some embodiments, the AUCG-repeat motif is preceded by a dipurine motif. In some embodiments, the dipurine motif is GA. In some embodiments, the dipurine motif is GG.

In some embodiments, the RLR agonists of the disclosure comprise an AUCG-repeat motif, wherein one or more uridine nucleosides (U) are substituted with a modified nucleoside. In some embodiments, wherein the modified nucleoside is ribothymidine (T). In some embodiments, the AUGC-repeat motif is $[AUCG]_3$, wherein the one or more uridine nucleosides (U) comprising the AUCG-repeat motif are substituted with a modified nucleoside, wherein the modified nucleoside is ribothymidine (T). In some embodiments, the AUGC-repeat motif is $[AUCG]_3$, wherein the one or more uridine nucleosides (U) comprising the AUCG-repeat motif are substituted with a modified nucleoside, wherein the modified nucleoside is ribothymidine (T), and wherein the AUGC-repeat motif is preceded by GG.

In some embodiments, the RLR agonists of the disclosure comprise an AUCG-repeat motif, wherein one or more guanosine nucleosides (G) are substituted with a modified nucleoside. In some embodiments, the modified nucleoside is inosine (I). In some embodiments, the AUGC-repeat motif is $[AUCG]_3$, wherein the one or more guanosine nucleosides (G) comprising the AUCG-repeat motif are substituted with a modified nucleoside, wherein the modified nucleoside is ribothymidine (T), and wherein the AUGC-repeat motif is preceded by GG.

In some embodiments, the RLR agonists of the disclosure comprise a AUCG-repeat motif, wherein the motif is preceded by a IG. In some embodiments, the AUCG-repeat motif is $[AUCG]_3$ and is preceded by a IG.

In some embodiments, the RLR agonists of the disclosure comprise an AUCG-repeat, wherein one or more guanosine nucleosides (G) are substituted with an inosine (I), wherein the AUCG-repeat is preceded by an inosine (I). In some embodiments, the guanosine nucleosides (G) comprising the AUCG-repeat are substituted with an inosine (I), wherein the AUCG-repeat is preceded by an inosine (I), wherein the 5' most nucleotide of the first polynucleotide comprises inosine (I).

In some embodiments, the 5' most nucleotide of the first oligonucleotide comprises inosine (I).

In some embodiments, the RLR agonists of the disclosure comprise a AUCG-repeat sequence motif, wherein the AUCG-repeat motif is $[AUCG]_2$. In some embodiments, the AUCG-repeat motif is preceded by a dipurine motif. In some embodiments, the dipurine motif is GG. In some embodiments, the AUCG-repeat motif is preceded by a purine triplet. In some embodiments, the purine triplet is GGG. In some embodiments, the AUCG-repeat motif is preceded by CCCCCG. In some embodiments, the AUCG-repeat motif is preceded by TCGUCG.

In some embodiments, the RLR agonists of the disclosure comprise a palindromic sequence, wherein the palindromic sequence comprises a sequence of <19, about 15-18, about 15, about 10-15, about 10, about 18, 17, 16, 15, 14, 13, 12, 11, 10, 9, 8, 7, 6, 5, or 4 nucleotides, or derivatives or analogs thereof, linked in any order that results in a palindrome.

In some embodiments, the linker is flanked by AU. In some embodiments, the linker is flanked by an AU-repeat motif, wherein the AU-repeat motif is $[AU]_n$, where n=2 to 3. In some embodiments, the AU-repeat motif is $[AU]_2$.

In some aspects, the disclosure provides an RLR agonist that specifically binds to a RLRs, wherein the agonist comprises a blunt-ended, hairpin RNA comprising at least one or more nucleotides comprising inosine which base pairs with cytidine, and wherein the agonist comprises the formula:

$5'$-$(N_1$-$N_2$-$X_1)$-$L$-$(X_2$-$N_3$-$N_4)$-$3'$, wherein (i) $(N_1$-$N_2$-$X_1)$ comprises a first polynucleotide comprising linked nucleotides $N_1$, $N_2$ and $X_1$;
(ii) $(X_2$-$N_3$-$N_4)$ comprises a second polynucleotide comprising linked nucleotides $X_2$, $N_3$ and $N_4$;
(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;
(iv) $N_1$ base pairs with $N_4$;
(v) $N_2$ base pairs with $N_3$;
(vi) $N_1$ comprises a 5' diphosphate or triphosphate moiety, or derivative or analog thereof;
(vii) $X_1$ and $X_2$ are each oligonucleotides comprising nucleosides selected from the group consisting of: adenosine, guanosine, cytidine, 5-methyluridine, uridine and inosine;
(viii) $X_1$ is complementary to X2;
(ix) $X_1$ and $X_2$ are each 12 nucleotides to 16 nucleotides in length and are the same length, and;
(x) L is a linker that covalently links the first polynucleotide and the second polynucleotide.

In other aspects, the disclosure provides a synthetic RIG-I-like receptor (RLR) agonist that specifically binds to RIG-I-like receptors (RLRs), wherein the agonist comprises a blunt-ended, hairpin RNA comprising a non-nucleotide linker, and wherein the agonist comprises the formula:

$5'$-$(N_1$-$N_2$-$X_1)$-$L$-$(X_2$-$N_3$-$N_4)$-$3'$, wherein (i) $(N_1$-$N_2$-$X_1)$ comprises a first polynucleotide comprising linked nucleotides $N_1$, $N_2$ and $X_1$;
(ii) $(X_2$-$N_3$-$N_4)$ comprises a second polynucleotide comprising linked nucleotides $X_2$, $N_3$ and $N_4$;
(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;
(iv) $N_1$ base pairs with $N_4$;
(v) $N_2$ base pairs with $N_3$;
(vi) $N_1$ comprises a 5' diphosphate or triphosphate moiety, or derivative or analog thereof;
(vii) $X_1$ and $X_2$ are each oligonucleotides comprising nucleosides selected from the group consisting of: adenosine, guanosine, cytidine, 5-methyluridine, uridine and inosine;
(viii) $X_1$ is complementary to $X_2$;
(ix) $X_1$ and $X_2$ are each 12 nucleotides to 16 nucleotides in length and are the same length, and;
(x) L is the non-nucleotide linker that covalently links the first polynucleotide and the second polynucleotide.

In some embodiments, inosine, if present in the RLR agonist, base pairs with cytidine.

In some embodiments, the linker (L) is a nucleotide linker or a non-nucleotide linker.

In some aspects, the disclosure provides an RLR agonist that specifically binds to RLRs, wherein the agonist comprises a blunt-ended, hairpin RNA comprising a nucleotide or non-nucleotide linker. RNA hairpins are among the most common RNA secondary structural elements, wherein the hybridized portion or "stem" of the hairpin are frequently capped by RNA tetraloops. RNA tetraloops are composed of characteristic four-loop nucleotides that form a compact and stable structure. While they can be formed by many different nucleotide sequences, UNCG (N=A, C, G, or U), GNRA (R=A or G), and CUUG tetraloops are found most often. Tetraloops usually help initiate RNA-folding processes and provide sites for tertiary contacts within or between RNAs and for protein binding, thereby facilitating the assembly of ribonucleoprotein particles. Further description of tetraloops can be found in Cheong, H., Kim, N. and Cheong, C. (2015). RNA Structure: Tetraloops. In eLS, John Wiley & Sons, Ltd (Ed.), which is incorporated herein by reference in its entirety.

Accordingly, in some embodiments, the RLR agonists of the disclosure comprise a nucleotide linker comprising a tetraloop. In some embodiments, the nucleotide sequence of the tetraloop is selected from the group consisting of:
(a) UNCG, wherein N=A, C, G, or U;
(b) GNRA, wherein N=A, C, G, or U, and wherein R=A or G;
(c) ANYA, wherein N=A, C, G, or U, and wherein Y=C or T;
(d) CUYG, wherein Y=C or T;
(e) UMAC, wherein M=A or C; and
(f) CUUG.

In some embodiments, the nucleotide linker comprises the nucleotide sequence UUUGAU or UGUUU. In some embodiments, the sequence of the tetraloop is UUCG. In some embodiments, the sequence of the tetraloop is GAUC. In some embodiments, the nucleotide linker comprises the nucleotide sequence UUUGAU. In some embodiments, the nucleotide linker comprises the nucleotide sequence UGUUU.

In other aspects, the RLR agonists of the disclosure comprise a non-nucleotide linker. As described herein nucleic acid loops (e.g., tetraloops) are a common element found in nucleic acid secondary structure. Nucleotide loops arise in folded domains occurring in intrastrand duplexes. Synthetic nucleic acids designed to contain hairpin loops comprising non-nucleotide linking groups (e.g., non-nucleotide linkers) can replace several nucleotides bridging a folded duplex structure. Non-nucleotide groups have been used as linkers in non-folded structures as well. Such linking groups may be useful replacements of natural nucleotide linkers (e.g., tetraloops). For example, they can shorten the synthesis of nucleic acid with a desired secondary structure by several steps, since one relatively long non-nucleotide linking group replaces several individual nucleotides which may normally constitute a loop. Such non-natural loops or linkers (e.g., non-nucleotide linkers) can confer resistance to degradation by nucleases which would ordinarily act on a natural loop structure in biological contexts (e.g., in a cell or in the circulation of a subject upon administration). A non-nucleotide linking group also has the potential to provide a more stable folded structure than occurs with the nucleotide loops and or linkers. Further description of non-nucleotide linkers can be found in Rumney and Kool (1995) J Am Chem Soc 117:5635-5646, which is incorporated herein by reference in its entirety.

Accordingly, in some embodiments, the RLR agonists of the disclosure comprise a non-nucleotide linker selected from the group consisting of:
(a) an ethylene glycol linker; and
(b) an alkyl linker.

In some embodiments, the non-nucleotide linker is a hexaethylene glycol linker. In some embodiments, the non-nucleotide linker is a C9 alkyl linker.

In some embodiments, the RLR agonist comprises a 5' diphosphate moiety, or a derivative or analog thereof. In some embodiments, the agonist comprises a 5' triphosphate moiety, or a derivative or analog thereof. In some embodiments, the derivative or analog thereof comprises a phosphate bioisostere is selected from: a phosphonate, a thiophosphonate, a phosphorothioate, a sulfate, a sulfonate, a sulfamate, a thiazolidinone, a carboxylate, a malonate, a boronic acid, a benzoxaborole, a boranophosphate, a squaramide.

In some embodiments, the agonist comprises a modified nucleotide, a modified nucleoside, or a modified nucleobase, or a combination thereof. In some embodiments, the agonist comprises a modification to the internucleotide linkages or to the polynucleotide backbone.

In some aspects, the RLR agonist of the disclosure exhibits at least one or more of the following properties:
(a) specifically binds to one or more RLRs (e.g. RIG-I, MDA5 and/or LGP2);
(b) increases RLR-mediated cytokine production;
(c) increases RLR-mediated expression of interferon-stimulated genes (ISGs);
(d) increases RLR-dependent intracellular signaling;
(e) increases stability of the duplex;
(f) increases binding affinity to RLRs;
(g) decreases off-target binding;
(h) increases biological half-life;
(i) increases biodistribution and bioavailability;
(j) increases and/or enhances uptake into cells and/or tissues;
(k) decreases immunogenicity; and
(l) a combination of any of (a)-(k).

In some aspects, the disclosure provides a synthetic RIG-I-like receptor (RLR) agonist that specifically binds to a RIG-I-like receptor (RLR), wherein the agonist comprises a blunt-ended, hairpin RNA comprising the formula:

$$5'\text{-}(N_1\text{-}N_2\text{-}X_1)\text{-}L\text{-}(X_2\text{-}N_3\text{-}N_4)\text{-}3', \text{ wherein}$$

(i) $(N_1\text{-}N_2\text{-}X_1)$ comprises a first polynucleotide comprising linked nucleotides $N_1$, $N_2$ and $X_1$;
(ii) $(X_2\text{-}N_3\text{-}N_4)$ comprises a second polynucleotide comprising linked nucleotides $X_2$, $N_3$ and $N_4$;
(iii) $N_1$, $N_2$, $N_3$ and $N_4$ each comprise a single nucleotide comprising a nucleoside selected from the group consisting of: adenosine, guanosine, cytidine, 5-methyluridine, uridine and inosine;
(iv) $N_1$ base pairs with $N_4$;
(v) $N_2$ base pairs with $N_3$;
(vi) $N_1$ comprises a 5' diphosphate or triphosphate moiety, or derivative or analog thereof;
(vii) $X_1$ and $X_2$ are each oligonucleotides comprising nucleosides selected from the group consisting of: adenosine, guanosine, cytidine, 5-methyluridine, uridine and inosine;
(viii) $X_1$ is complementary to $X_2$;
(ix) $X_1$ and $X_2$ are each 12 nucleotides to 16 nucleotides in length and are the same length, and;
(x) L is a linker that operably links the first polynucleotide and the second polynucleotide,
wherein at least one of N1, N2, N3, and N4 is inosine and/or at least one of X1 and/or X2 comprises at least one inosine nucleoside, and wherein the inosine nucleoside base pairs with cytidine in the hairpin RNA.

In some embodiments, N1 comprises inosine and N4 comprises cytidine. In some embodiments, N1 comprises cytidine and N4 comprises inosine. In some embodiments, N2 comprise inosine and N3 comprises cytidine. In some embodiments, N2 comprises cytidine and N3 comprises inosine. In some embodiments, N1 comprises guanosine. In some embodiments, N2 comprises guanosine. In some embodiments, N1 comprises cytidine. In some embodiments, N2 comprises cytidine. In some embodiments, N1 and N2 comprise guanosine and $N_3$ and $N_4$ comprise cytidine. In some embodiments, N1 and N2 comprise cytidine and $N_3$ and $N_4$ comprise guanosine. In some embodiments, N1 and N2 comprise inosine and $N_3$ and $N_4$ comprise cytidine. In some embodiments, N1 and N2 comprise cytidine and $N_3$ and $N_4$ comprise inosine. In some embodiments, N1 comprises inosine and N4 comprises cytidine, and X1 and/or X2 each comprise at least one inosine. In some embodiments, N2 comprises inosine and N3 comprises cytidine, and X1 and/or X2 each comprise at least one inosine. In some embodiments, N1 and N2 comprise guanosine $N_3$ and $N_4$ comprise cytidine, and X1 and/or X2 each comprise at least one inosine. In some embodiments, N1 and N2 comprise guanosine and N3 and N4 comprise cytidine, and X1 and X2 each comprise at least one inosine. In some embodiments, N1 and N2 comprise cytidine and N3 and N4 comprise guanosine, and X1 and X2 each comprise at least one inosine. In some embodiments, N1 and N2 comprise guanosine and N3 and N4 comprise cytidine, and X1 and X2 each comprise inosine and no guanosine nucleosides. In some embodiments, N1 and N2 comprise cytidine and $N_3$ and $N_4$ comprise guanosine, and X1 and X2 each comprise inosine and no guanosine nucleosides. In some embodiments, N1 and N2 comprise inosine and N3 and N4 comprise cytidine, and X1 and/or X2 each comprise at least one inosine. In some embodiments, N1 and N2 comprise inosine and N3 and N4 comprise cytidine, and X1 and X2 each comprise at least one inosine. In some embodiments, N1 and N2 comprise cytidine and N3 and N4 comprise inosine, and X1 and/or X2 each comprise at least one inosine. In some embodiments, N1 and N2 comprise inosine and N3 and N4 comprise cytidine, and X1 and X2 comprise inosine and no guanosine nucleosides. In some embodiments, N1 and N2 comprise cytidine and $N_3$ and $N_4$ comprise inosine, and X1 and X2 comprise inosine and no guanosine nucleosides. In some embodiments, X1 and X2 are each 12 nucleotides and comprise 1, 2, 3 or 4 inosine nucleosides. In some embodiments, X1 and X2 are each 13 nucleotides and comprise 1, 2, 3, 4 or 5 inosine nucleosides. In some embodiments, X1 and X2 are each 14 nucleotides and comprise 1, 2, 3, 4, 5 or 6 inosine nucleosides. In some embodiments, X1 and X2 are each 15 nucleotides and comprise 1, 2, 3, 4, 5, 6, or 7 inosine nucleosides. In some embodiments, X1 and X2 are each 16 nucleotides and each comprise 1, 2, 3, 4, 5, 6, 7, or 8 inosine nucleosides. In some embodiments, X1 and X2 are each 12 nucleotides and comprise at least 10%, 20%, 30% or 40% inosine nucleosides.

In some aspects, the disclosure provides a synthetic RIG-I-like receptor (RLR) agonist that specifically binds to a RIG-I-like receptor (RLR), wherein the agonist comprises a blunt-ended, hairpin RNA comprising the formula:

5'-(N$_1$-N$_2$-X$_1$)-L-(X$_2$-N$_3$-N$_4$)-3', wherein (i) (N$_1$-N$_2$-X$_1$) comprises a first polynucleotide comprising linked nucleotides N$_1$, N$_2$ and X$_1$;

(ii) (X$_2$-N$_3$-N$_4$) comprises a second polynucleotide comprising linked nucleotides X$_2$, N$_3$ and N$_4$;

(iii) N$_1$, N$_2$, N$_3$ and N$_4$ each comprise a single nucleotide comprising a nucleoside selected from the group consisting of: adenosine, guanosine, cytidine, 5-methyluridine, uridine and inosine;

(iv) N$_1$ base pairs with N$_4$;

(v) N$_2$ base pairs with N$_3$;

(vi) N$_1$ comprises a 5' diphosphate or triphosphate moiety, or derivative or analog thereof;

(vii) X$_1$ comprises a sequence motif [AUCN5]$_x$, wherein N$_5$ is comprises guanosine or inosine, wherein x is an integer whose value indicates the number of sequence motifs, and wherein x=3 or 4;

(viii) X$_2$ comprises a sequence motif [CN$_6$AU]$_y$, wherein N6 comprises guanosine or inosine, wherein y is an integer whose value indicates the number of sequence motifs, and wherein y=3 or 4;

(ix) L is a linker that operably links the first polynucleotide and the second polynucleotide, optionally, wherein at least one of N1, N2, N3, and N4 is inosine, and wherein the inosine nucleoside base pairs with cytidine in the hairpin RNA. In some embodiments, N5 comprises inosine and N6 comprises inosine. In some embodiments, N5 comprises guanosine and N6 comprises inosine. In some embodiments, N5 comprises inosine and N6 comprises guanosine. In some embodiments, N5 comprises guanosine (G) and N6 comprises guanosine (G). In some embodiments, x=3 and y=3. In some embodiments, x=4 and y=4. In some embodiments, N1 comprises inosine (I) and N4 comprises cytidine (C). In some embodiments, N2 comprises inosine (I) and N3 comprises cytidine (C). In some embodiments, N3 comprises inosine (I) and N2 comprises cytidine (C). In some embodiments, N4 comprises inosine (I) and N1 comprises cytidine (C). In some embodiments, N1 comprises guanosine (G). In some embodiments, N2 comprises guanosine (G). In some embodiments, N1 comprises cytidine (C). In some embodiments, N2 comprises cytidine (C). In some embodiments, N1 and N2 comprise guanosine (G) and $N_3$ and $N_4$ comprise cytidine (C). In some embodiments, N1 and N2 comprise cytidine (C) and $N_3$ and $N_4$ comprise guanosine (G). In some embodiments, N1 and N2 comprise inosine (I) and $N_3$ and $N_4$ comprise cytidine (C). In some embodiments, N1 and N2 comprise cytidine (C) and $N_3$ and $N_4$ comprise inosine (I).

In some embodiments, the linker (L) is a nucleotide linker or a non-nucleotide linker. In some embodiments, the linker (L) is a nucleotide linker comprising a tetraloop, wherein the nucleotide sequence of the tetraloop is selected from the group consisting of:

(a) UNCG, wherein N=A, C, G, or U;
(b) GNRA, wherein N=A, C, G, or U, and wherein R=A or G;
(c) ANYA, wherein N=A, C, G, or U, and wherein Y=C or T;
(d) CUYG, wherein Y=C or T;
(e) UMAC, wherein M=A or C; and
(f) CUUG.

In some embodiments, the linker (L) is a nucleotide linker comprising the nucleotide sequence UUUGAU or UGUUU. In some embodiments, the nucleotide linker comprises the nucleotide sequence UUUGAU. In some embodiments, the nucleotide linker comprises the nucleotide sequence UGUUU.

In some embodiments, the linker (L) is a nucleotide linker comprising a tetraloop, wherein the sequence of the tetraloop is UUCG. In some embodiments, the sequence of the tetraloop is GAUC.

In some embodiments, the linker (L) is a non-nucleotide linker selected from the group consisting of:

(a) an ethylene glycol linker; and
(b) an alkyl linker.

In some embodiments, the non-nucleotide linker is a hexaethylene glycol linker. In some embodiments, the the non-nucleotide linker is a C9 alkyl linker.

In some embodiments, the RLR agonist comprises a 5' diphosphate moiety, or a derivative or analog thereof. In some embodiments, the agonist comprises a 5' triphosphate moiety, or a derivative or analog thereof. In some embodiments, the derivative or analog thereof comprises a phosphate bioisostere is selected from: a phosphonate, a thiophosphonate, a phosphorothioate, a sulfate, a sulfonate, a sulfamate, a thiazolidinone, a carboxylate, a malonate, a boronic acid, a benzoxaborole, a boranophosphate, a squaramide.

In some embodiments, the RLR agonist comprises a modified nucleotide, a modified nucleoside, or a modified nucleobase, or a combination thereof. In some embodiments, the agonist comprises a modification to the internucleotide linkages or to the polynucleotide backbone.

In some embodiments, the RLR agonist exhibits at least one or more of the following properties:
  (a) specifically binds to one or more RLRs (e.g. RIG-1, MDA5 and/or LGP2);
  (b) increases RLR-mediated cytokine production;
  (c) increases RLR-mediated expression of interferon-stimulated genes (ISGs);
  (d) increases RLR-dependent intracellular signaling;
  (e) increases stability of the duplex;
  (f) increases binding affinity to RLRs;
  (g) decreases off-target binding;
  (h) increases biological half-life;
  (i) increases biodistribution and bioavailability;
  (j) increases and/or enhances uptake into cells and/or tissues;
  (k) decreases immunogenicity; and
  (l) a combination of any of (a)-(k).

In some aspects, the disclosure provides a synthetic RIG-I-like receptor (RLR) agonist that specifically binds to a RIG-I-like receptor (RLR), wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof, wherein the agonist comprises a sequence motif that provides at least one improved biological activity mediated by the RLR relative to an agonist that does not comprise the sequence motif, and wherein the agonist comprises the nucleotide sequence selected from the group consisting of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and 36.

In some aspects, the disclosure provides a synthetic RIG-I-like receptor (RLR) agonist that specifically binds to a RIG-I-like receptor (RLR), wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof, wherein the agonist comprises a sequence motif that provides at least one improved biological activity mediated by the RLR relative to an agonist that does not comprise the sequence motif, and wherein the first polynucleotide and the second polynucleotide comprise the nucleotide sequences selected from the group consisting of:
  (i) SEQ ID NO: 37 and 68, respectively;
  (ii) SEQ ID NO: 38 and 69, respectively;
  (iii) SEQ ID NO: 39 and 70, respectively;
  (iv) SEQ ID NO: 40 and 71, respectively;
  (v) SEQ ID NO: 41 and 72, respectively;
  (vi) SEQ ID NO: 42 and 73, respectively;
  (vii) SEQ ID NO: 43 and 74, respectively;
  (viii) SEQ ID NO: 44 and 75, respectively;
  (ix) SEQ ID NO: 45 and 76, respectively;
  (x) SEQ ID NO: 46 and 77, respectively;
  (xi) SEQ ID NO: 47 and 78, respectively;
  (xii) SEQ ID NO: 48 and 79, respectively;
  (xiii) SEQ ID NO: 49 and 80, respectively;
  (xiv) SEQ ID NO: 50 and 81, respectively;
  (xv) SEQ ID NO: 51 and 82, respectively;
  (xvi) SEQ ID NO: 52 and 83, respectively;
  (xvii) SEQ ID NO: 53 and 84, respectively;
  (xviii) SEQ ID NO: 54 and 85, respectively;
  (xix) SEQ ID NO: 55 and 86, respectively;
  (xx) SEQ ID NO: 56 and 87, respectively;
  (xxi) SEQ ID NO: 57 and 88, respectively;
  (xxii) SEQ ID NO: 58 and 89, respectively;
  (xxiii) SEQ ID NO: 59 and 89, respectively;
  (xxiv) SEQ ID NO: 60 and 90, respectively;
  (xxv) SEQ ID NO: 61 and 91, respectively;
  (xxvi) SEQ ID NO: 62 and 92, respectively;
  (xxvii) SEQ ID NO: 63 and 91, respectively;
  (xxviii) SEQ ID NO: 64 and 93, respectively;
  (xxix) SEQ ID NO: 65 and 94, respectively;
  (xxx) SEQ ID NO: 66 and 95, respectively;
  (xxxi) SEQ ID NO: 67 and 96, respectively; and
  (xxxii) SEQ ID NO: 63 and 97, respectively.

In some aspects, the disclosure provides a synthetic RIG-I-like receptor (RLR) agonist that specifically binds to a RIG-I-like receptor (RLR), wherein the agonist comprises a blunt-ended, hairpin RNA comprising at least one or more nucleotides comprising inosine which base pairs with cytidine, and wherein the agonist comprises the nucleotide sequence selected from the group consisting of SEQ ID NOs: 22, 23 and 25.

In some aspects, the disclosure provides a synthetic RIG-I-like receptor (RLR) agonist that specifically binds to a RIG-I-like receptor (RLR), wherein the agonist comprises a blunt-ended, hairpin RNA comprising at least one or more nucleotides comprising inosine which base pairs with cytidine, wherein the agonist comprises the formula 5'-($N_1$-$N_2$-$X_1$)-L-($X_2$-$N_3$-$N_4$)-3', wherein ($N_1$-$N_2$-$X_1$) comprises a first polynucleotide and ($X2$-$N_3$-$N_4$) comprises a second polynucleotide, and wherein the first polynucleotide and the second polynucleotide comprise the nucleotide sequences selected from the group consisting of:
  (i) SEQ ID NO: 58 and 89, respectively;
  (ii) SEQ ID NO: 59 and 89, respectively; and
  (iii) SEQ ID NO: 61 and 91, respectively.

In some aspects, the disclosure provides a synthetic RIG-I-like receptor (RLR) agonist that specifically binds to RIG-I-like receptors (RLRs), wherein the agonist comprises a blunt-ended, hairpin RNA comprising a non-nucleotide linker, wherein the agonist comprises the formula 5'-($N_1$-$N_2$-$X_1$)-L-($X_2$-$N_3$-$N_4$)-3', wherein ($N_1$-$N_2$-$X_1$) comprises a first polynucleotide and ($X_2$-$N_3$-$N_4$) comprises a second polynucleotide, and wherein the first polynucleotide and the second polynucleotide comprise the nucleotide sequences selected from the group consisting of:
  (i) SEQ ID NO: 37 and 68, respectively;
  (ii) SEQ ID NO: 38 and 69, respectively;
  (iii) SEQ ID NO: 39 and 70, respectively;
  (iv) SEQ ID NO: 40 and 71, respectively;
  (v) SEQ ID NO: 41 and 72, respectively;
  (vi) SEQ ID NO: 42 and 73, respectively;
  (vii) SEQ ID NO: 43 and 74, respectively;
  (viii) SEQ ID NO: 44 and 75, respectively;
  (ix) SEQ ID NO: 45 and 76, respectively;
  (x) SEQ ID NO: 46 and 77, respectively;
  (xi) SEQ ID NO: 47 and 78, respectively;
  (xii) SEQ ID NO: 48 and 79, respectively;
  (xiii) SEQ ID NO: 49 and 80, respectively;
  (xiv) SEQ ID NO: 50 and 81, respectively;
  (xv) SEQ ID NO: 51 and 82, respectively;
  (xvi) SEQ ID NO: 52 and 83, respectively;

(xvii) SEQ ID NO: 53 and 84, respectively;
(xviii) SEQ ID NO: 54 and 85, respectively;
(xix) SEQ ID NO: 55 and 86, respectively;
(xx) SEQ ID NO: 56 and 87, respectively;
(xxi) SEQ ID NO: 57 and 88, respectively;
(xxii) SEQ ID NO: 58 and 89, respectively;
(xxiii) SEQ ID NO: 59 and 89, respectively;
(xxiv) SEQ ID NO: 60 and 90, respectively;
(xxv) SEQ ID NO: 61 and 91, respectively;
(xxvi) SEQ ID NO: 62 and 92, respectively;
(xxvii) SEQ ID NO: 63 and 91, respectively;
(xxviii) SEQ ID NO: 64 and 93, respectively;
(xxix) SEQ ID NO: 65 and 94, respectively;
(xxx) SEQ ID NO: 66 and 95, respectively;
(xxxi) SEQ ID NO: 67 and 96, respectively; and
(xxxii) SEQ ID NO: 63 and 97, respectively.

In some aspects, the disclosure provides RLR agonists wherein the nucleotide sequence comprising the agonist is not complementary to a genomic DNA sequence or mRNA sequence, wherein the RLR agonist does not participate in RNA interference, and wherein the RLR agonist does not silence gene expression.

RLR Agonists Comprising Modified Nucleobases, Nucleosides, or Nucleotides

In some embodiments, an RLR agonist of the disclosure comprises one or more modified nucleobases, nucleosides, or nucleotides. In some embodiments, modified RLR agonists may have useful properties, including enhanced stability, intracellular retention, enhanced target binding, and/or an increase in induction of the innate immune response of a cell into which the RLR agonist is introduced, as compared to a reference unmodified RLR agonist. Therefore, use of modified RLR agonists may enhance the efficiency of target binding, intracellular retention of nucleic acids, as well as possess reduced immunogenicity. In one embodiment, the agonist provided by the disclosure is comprised of one or more oligonucleotides that comprise at least one region modified to increase target binding affinity. Affinity of an oligonucleotide for its target polypeptide (e.g. an RLR receptor) can be determined by, for example, measuring the degree of fluorescence polarization (FP) upon binding of a fluorescently-labeled oligonucleotide to its target (Moerke (2009) Curr Protoc Chem Biol 1(1):1-15).

In another embodiment, the RLR agonist provided by the disclosure is comprised of at least one oligonucleotide comprising at least one region comprising at least one modified nucleobase, nucleoside, or nucleotide that increases the stability of the duplex. The stability of the duplex can be routinely determined by measuring the Tm of the duplex, which is the temperature at which the two oligonucleotide strands comprising the duplex dissociate; dissociation is detected spectrophotometrically. The higher the Tm, the greater the stability of the duplex.

In one embodiment, the region of the oligonucleotide which is modified to increase duplex stability comprises at least one nucleotide modified at the 2' position of the sugar, most preferably a 2'-O-alkyl, 2-O-alkyl-O-alkyl or 2'-fluoro-modified nucleotide. In another embodiment, an oligonucleotide comprising an RLR agonist is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than an unmodified oligonucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance (De Mesmaeker et al., 1995, Acc. Chem. Res. 28:366-374).

Specific examples of some preferred oligonucleotides envisioned for this invention include those containing modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones (including those synthesized in a stereo-specific manner) and those with heteroatom backbones, particularly CH2-NH—O—CH2, CH2-N(CH3)-O—CH2 [known as a methylene(methylimino) or MMI backbone], CH2-O—N(CH3)-CH2, CH2-N(CH3)-N(CH3)-CH2 and O—N(CH3)-CH2-CH2 backbones, wherein the native phosphodiester backbone is represented as O—P—O—CH2). The amide backbones disclosed by De Mesmaeker et al. (1995, Acc. Chem. Res. 28:366-374) are also preferred. Oligonucleotides may also contain one or more substituted sugar moieties. Preferred oligonucleotides comprise one of the following at the 2' position: OH, SH, SCH3, F, OCN, OCH3OCH3, OCH3O(CH2)nCH3, O(CH2)nNH2 or O(CH2)nCH3 where n is from 1 to about 10; C1 to C10 lower alkyl, alkoxyalkoxy (also known in the art as O-alkyl-O-alkyl), substituted lower alkyl, alkaryl or aralkyl; Cl; Br; CN; CF3; OCF3; O, S—, or N-alkyl; O—O, S—, or N-alkenyl; SOCH3; SO2CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH2CH2OCH3, also known as 2'-O-(2-methoxyethyl) or 2'-MOE] (Martin et al., Helv. Chim. Acta, 1995, 78, 486). Other preferred modifications include 2'-methoxy (2'-O—CH3), 2'-propoxy (2'-OCH2CH2CH3) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-me pyrimidines, particularly 5-methylcytosine (also referred to as 5-methyl-2'deoxycytosine and often referred to in the art as 5-me-C), 5-hydroxymethylcytosine (HMC), glycosyl HMC and gentobiosyl HMC, as well as synthetic nucleobases, e.g., 2-aminoadenine, 2-thiouracil, 2-thiothymine, 5-bromouracil, 5-hydroxymethyluracil, 8-azaguanine, 7-deazaguanine, N6(6-aminohexyl)adenine and 2,6-diaminopurine. Kornberg, A., DNA Replication, W. H. Freeman & Co., San Francisco, 1980, pp75-77; Gebeyehu, G., et al., 1987, Nucl. Acids Res. 15:4513). A "universal" base known in the art, e.g., inosine, may be included. 5-me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., Proc. Natl. Acad. Sci. USA, 1989, 86, 6553), cholic acid (Manoharan et al., Bioorg. Med. Chem. Let., 1994, 4, 1053), a thioether, e.g., hexyl-S-tritylthiol (Manoharan et al., Ann. N.Y. Acad. Sci., 1992, 660, 306; Manoharan et al., Bioorg. Med. Chem. Let., 1993, 3, 2765), a thiocholesterol (Oberhauser et al., Nucl. Acids Res., 1992, 20, 533), an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49), a phospholipid, a polyamine or a polyethylene glycol chain (Manoharan et al., Nucleosides & Nucleotides, 1995, 14, 969), or adamantane acetic acid (Manoharan et al., Tetrahedron Lett., 1995, 36, 3651). Oligonucleotides comprising lipophilic moieties, and methods for preparing such oligonucleotides are known in the art, for example, U.S. Pat. Nos. 5,138,045, 5,218,105 and 5,459,255.

The oligonucleotides of the invention may be provided as prodrugs, which comprise one or more moieties which are cleaved off, generally in the body, to yield an active oligonucleotide. One example of a prodrug approach is described by Imbach et al. in WO Publication 94/26764.

It is not necessary for all positions in a given oligonucleotide to be uniformly modified, and in fact more than one of the aforementioned modifications may be incorporated in a single oligonucleotide or even at within a single nucleoside within an oligonucleotide.

The oligonucleotides in accordance with this invention preferably are from about 8 to about 50 nucleotides in length. In the context of this invention it is understood that this encompasses non-naturally occurring oligomers as hereinbefore described, having 8 to 50 monomers.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the knowledge and ability of one of ordinary skill in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

In some embodiments, an RLR agonist includes one or more (e.g., 1, 2, 3 or 4) different modified nucleobases, nucleosides, or nucleotides. In some embodiments, an RLR agonist includes one or more (e.g., 1, 2, 3, 4, 5, 6, 7, 8, 9, 10, 20, 30, 40, 50, 60, 70, 80, 90, 100, or more) different modified nucleobases, nucleosides, or nucleotides. In some embodiments, the modified RLR agonist may have reduced degradation in a cell into which the RLR agonist is introduced, relative to a corresponding unmodified RLR agonist.

In some embodiments, the modified nucleobase is a modified uracil. Exemplary nucleobases and nucleosides having a modified uracil include pseudouridine (ψ), pyridin-4-one ribonucleoside, 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine ($ho^5U$), 5-aminoallyl-uridine, 5-halo-uridine (e.g., 5-iodo-uridine or 5-bromo-uridine), 3-methyl-uridine ($m^3U$), 5-methoxy-uridine ($mo^5U$), uridine 5-oxyacetic acid ($cmo^5U$), uridine 5-oxyacetic acid methyl ester ($mcmo^5U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine ($mcm^5U$), 5-methoxycarbonylmethyl-2-thio-uridine ($mcm^5 s^2U$), 5-aminomethyl-2-thio-uridine ($nm^5 s^2U$), 5-methyl aminomethyl-uridine ($mnm^5U$), 5-methyl aminomethyl-2-thio-uridine ($mnm^5 s^2U$), 5-methyl aminomethyl-2-seleno-uridine ($mnm^5 se^2U$), 5-carbamoylmethyl-uridine ($ncm^5U$), 5-carboxymethylaminomethyl-uridine ($cmnm^5U$), 5-carboxymethyl aminoethyl-2-thio-uridine ($cmnm^5 s^2U$), 5-propynyl-uridine, 1-propynyl-pseudouridine, 5-taurinomethyl-uridine (τ$m^5U$), 1-taurinomethyl-pseudouridine, 5-taurinomethyl-2-thio-uridine(τ$m^5 s^2U$), 1-taurinomethyl-4-thio-pseudouridine, 5-methyl-uridine ($m^5U$, i.e., having the nucleobase deoxythymine), 1-methyl-pseudouridine ($m^1ψ$), 5-methyl-2-thio-uridine ($m^5 s^2U$), 1-methyl-4-thio-pseudouridine ($m^1s^4ψ$), 4-thio-1-methyl-pseudouridine, 3-methyl-pseudouridine ($m^3ψ$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine ($acp^3U$), 1-methyl-3-(3-amino-3-carboxypropyl)pseudouridine ($acp^3 ψ$), 5-(isopentenylaminomethyl)uridine ($inm^5U$), 5-(isopentenylaminomethyl)-2-thio-uridine ($inm^5 s^2U$), α-thio-uridine, 2'-O-methyl-uridine (Um), 5,2'-O-dimethyl-uridine ($m^5Um$), 2'-O-methyl-pseudouridine (ψm), 2-thio-2'-O-methyl-uridine ($s^2Um$), 5-methoxycarbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), and 5-(isopentenylaminomethyl)-2'-O-methyl-uridine ($inm^5Um$), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)] uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine ($m^3C$), N4-acetyl-cytidine ($ac^4C$), 5-formyl-cytidine ($f^5C$), N4-methyl-cytidine ($m^4C$), 5-methyl-cytidine ($m^5C$), 5-halo-cytidine (e.g., 5-iodo-cytidine), 5-hydroxymethyl-cytidine ($hm^5C$), 1-methyl-pseudoisocytidine, pyrrolo-cytidine, pyrrolo-pseudoisocytidine, 2-thio-cytidine ($s^2C$), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine (k$_2$C), α-thio-cytidine, 2'-O-methyl-cytidine (Cm), 5,2'-O-dimethyl-cytidine (m$^5$Cm), N4-acetyl-2'-O-methyl-cytidine (ac$^4$Cm), N4,2-O-dimethyl-cytidine (m$^4$Cm), 5-formyl-2'-O-methyl-cytidine (f$^5$Cm), N4,N4,2'-O-trimethyl-cytidine (m$^4_2$Cm), 1-thio-cytidine, 2'-F-ara-cytidine, 2'-F-cytidine, and 2'-OH-ara-cytidine.

In some embodiments, the modified nucleobase is a modified adenine. Exemplary nucleobases and nucleosides having a modified adenine include α-thio-adenosine, 2-amino-purine, 2, 6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenosine (m$^1$A), 2-methyl-adenine (m$^2$A), N6-methyl-adenosine (m$^6$A), 2-methylthio-N6-methyl-adenosine (ms$^2$m$^6$A), N6-isopentenyl-adenosine (i$^6$A), 2-methylthio-N6-isopentenyl-adenosine (ms$^2$i$^6$A), N6-(cis-hydroxyisopentenyl)adenosine (io$^6$A), 2-methylthio-N6-(cis-hydroxyisopentenyl)adenosine (ms$^2$io$^6$A), N6-glycinyl-carbamoyl-adenosine (g$^6$A), N6-threonylcarbamoyl-adenosine (t$^6$A), N6-methyl-N6-threonylcarbamoyl-adenosine (m$^6$t$^6$A), 2-methylthio-N6-threonylcarbamoyl-adenosine (ms$^2$g$^6$A), N6,N6-dimethyl-adenosine (m$^6_2$A), N6-hydroxynorvalylcarbamoyl-adenosine (hn$^6$A), 2-methylthio-N6-hydroxynorvalylcarbamoyl-adenosine (ms$^2$hn$^6$A), N6-acetyl-adenosine (ac$^6$A), 7-methyl-adenine, 2-methylthio-adenine, 2-methoxy-adenine, α-thio-adenosine, 2'-O-methyl-adenosine (Am), N6,2'-O-dimethyl-adenosine (m$^6$Am), N6,N6,2'-O-trimethyl-adenosine (m$^6_2$Am), 1,2'-O-dimethyl-adenosine (m$^1$Am), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

In some embodiments, the modified nucleobase is a modified guanine. Exemplary nucleobases and nucleosides having a modified guanine include α-thio-guanosine, inosine (I), 1-methyl-inosine (m$^1$I), wyosine (imG), methyl-wyosine (mimG), 4-demethyl-wyosine (imG-14), isowyosine (imG2), wybutosine (yW), peroxywybutosine (o$_2$yW), hydroxywybutosine (OhyW), undermodified hydroxywybutosine (OhyW*), 7-deaza-guanosine, queuosine (Q), epoxyqueuosine (oQ), galactosyl-queuosine (galQ), mannosyl-queuosine (manQ), 7-cyano-7-deaza-guanosine (preQ$_0$), 7-aminomethyl-7-deaza-guanosine (preQ$_1$), archaeosine (G$^+$), 7-deaza-8-aza-guanosine, 6-thio-guanosine, 6-thio-7-deaza-guanosine, 6-thio-7-deaza-8-aza-guanosine, 7-methyl-guanosine (m$^7$G), 6-thio-7-methyl-guanosine, 7-methyl-inosine, 6-methoxy-guanosine, 1-methyl-guanosine (m$^1$G), N2-methyl-guanosine (m$^2$G), N2,N2-dimethyl-guanosine (m$^2_2$G), N2,7-dimethyl-guanosine (m$^{2,7}$G), N2, N2,7-dimethyl-guanosine (m$^{2,2,7}$G), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine (m$^2$Gm), N2,N2-dimethyl-2'-O-methyl-guanosine (m$^2_2$Gm), 1-methyl-2'-O-methyl-guanosine (m$^1$Gm), N2,7-dimethyl-2'-O-methyl-guanosine (m$^{2,7}$Gm), 2'-O-methyl-inosine (Im), 1,2'-O-dimethyl-inosine (m$^1$Im), 2'-O-ribosylguanosine (phosphate) (Gr(p)), 1-thio-guanosine, O6-methyl-guanosine, 2'-F-ara-guanosine, and 2'-F-guanosine.

In some embodiments, an RLR agonist of the disclosure includes a combination of one or more of the aforementioned modified nucleobases (e.g., a combination of 2, 3 or 4 of the aforementioned modified nucleobases.)

In certain embodiments, an RLR agonist of the disclosure is uniformly modified (i.e., fully modified, modified through-out the entire sequence) for a particular modification. For example, an RLR agonist can be uniformly modified with 5-methyl-cytidine (m$^5$C), meaning that all cytosine residues in the mRNA sequence are replaced with 5-methyl-cytidine (m$^5$C). Similarly, an RLR agonist of the disclosure can be uniformly modified for any type of nucleoside residue present in the sequence by replacement with a modified residue such as those set forth above.

Examples of nucleoside modifications and combinations thereof that may be present in an RLR agonist of the present disclosure include, but are not limited to, those described in PCT Patent Application Publications: WO2012045075, WO2014081507, WO2014093924, WO2014164253, and WO2014159813.

The RLR agonists of the disclosure can include a combination of modifications to the sugar, the nucleobase, and/or the internucleoside linkage. These combinations can include any one or more modifications described herein.

Examples of modified nucleosides and modified nucleoside combinations are provided below in Table 1 and Table 2. These combinations of modified nucleotides can be used to form the RLR agonists of the disclosure. In certain embodiments, the modified nucleosides may be partially or completely substituted for the natural nucleotides of the RLR agonists of the disclosure. As a non-limiting example, the natural nucleotide uridine may be substituted with a modified nucleoside described herein. In another non-limiting example, the natural nucleoside uridine may be partially substituted (e.g., about 0.1%, 1%, 5%, 10%, 15%, 20%, 25%, 30%, 35%, 40%, 45%, 50%, 55%, 60%, 65%, 70%, 75%, 80%, 85%, 90%, 95% or 99.9% of the natural uridines) with at least one of the modified nucleoside disclosed herein.

TABLE 1

Combinations of Nucleoside Modifications

| Modified Nucleotide | Modified Nucleotide Combination |
|---|---|
| α-thio-cytidine | α-thio-cytidine/5-iodo-uridine |
| | α-thio-cytidine/N1-methyl-pseudouridine |
| | α-thio-cytidine/α-thio-uridine |
| | α-thio-cytidine/5-methyl-uridine |
| | α-thio-cytidine/pseudo-uridine |
| | about 50% of the cytosines are α-thio-cytidine |
| pseudoisocytidine | pseudoisocytidine/5-iodo-uridine |
| | pseudoisocytidine/N1-methyl-pseudouridine |
| | pseudoisocytidine/α-thio-uridine |
| | pseudoisocytidine/5-methyl-uridine |
| | pseudoisocytidine/pseudouridine |
| | about 25% of cytosines are pseudoisocytidine |
| | pseudoisocytidine/about 50% of uridines are N1-methyl-pseudouridine and about 50% of uridines are pseudouridine |
| | pseudoisocytidine/about 25% of uridines are N1-methyl-pseudouridine and about 25% of uridines are pseudouridine |
| pyrrolo-cytidine | pyrrolo-cytidine/5-iodo-uridine |
| | pyrrolo-cytidine/N1-methyl-pseudouridine |
| | pyrrolo-cytidine/α-thio-uridine |
| | pyrrolo-cytidine/5-methyl-uridine |
| | pyrrolo-cytidine/pseudouridine |
| | about 50% of the cytosines are pyrrolo-cytidine |

TABLE 1-continued

Combinations of Nucleoside Modifications

| Modified Nucleotide | Modified Nucleotide Combination |
|---|---|
| 5-methyl-cytidine | 5-methyl-cytidine/5-iodo-uridine |
| | 5-methyl-cytidine/N1-methyl-pseudouridine |
| | 5-methyl-cytidine/α-thio-uridine |
| | 5-methyl-cytidine/5-methyl-uridine |
| | 5-methyl-cytidine/pseudouridine |
| | about 25% of cytosines are 5-methyl-cytidine |
| | about 50% of cytosines are 5-methyl-cytidine |
| | 5-methyl-cytidine/5-methoxy-uridine |
| | 5-methyl-cytidine/5-bromo-uridine |
| | 5-methyl-cytidine/2-thio-uridine |
| | 5-methyl-cytidine/about 50% of uridines are 2-thio-uridine |
| | about 50% of uridines are 5-methyl-cytidine/about 50% of uridines are 2-thio-uridine |
| N4-acetyl-cytidine | N4-acetyl-cytidine/5-iodo-uridine |
| | N4-acetyl-cytidine/N1-methyl-pseudouridine |
| | N4-acetyl-cytidine/α-thio-uridine |
| | N4-acetyl-cytidine/5-methyl-uridine |
| | N4-acetyl-cytidine/pseudouridine |
| | about 50% of cytosines are N4-acetyl-cytidine |
| | about 25% of cytosines are N4-acetyl-cytidine |
| | N4-acetyl-cytidine/5-methoxy-uridine |
| | N4-acetyl-cytidine/5-bromo-uridine |
| | N4-acetyl-cytidine/2-thio-uridine |
| | about 50% of cytosines are N4-acetyl-cytidine/about 50% of uridines are 2-thio-uridine |

TABLE 2

Modified Nucleosides and Combinations Thereof 1-(2,2,2-Trifluoroethyl)pseudo-UTP
1-Ethyl-pseudo-UTP
1-Methyl-pseudo-U-alpha-thio-TP
1-methyl-pseudouridine TP, ATP, GTP, CTP
1-methyl-pseudo-UTP/5-methyl-CTP/ATP/GTP
1-methyl-pseudo-UTP/CTP/ATP/GTP
1-Propyl-pseudo-UTP
25% 5-Aminoallyl-CTP + 75% CTP/25% 5-Methoxy-UTP + 75% UTP
25% 5-Aminoallyl-CTP + 75% CTP/75% 5-Methoxy-UTP + 25% UTP
25% 5-Bromo-CTP + 75% CTP/25% 5-Methoxy-UTP + 75% UTP
25% 5-Bromo-CTP + 75% CTP/75% 5-Methoxy-UTP + 25% UTP
25% 5-Bromo-CTP + 75% CTP/1-Methyl-pseudo-UTP
25% 5-Carboxy-CTP + 75% CTP/25% 5-Methoxy-UTP + 75% UTP
25% 5-Carboxy-CTP + 75% CTP/75% 5-Methoxy-UTP + 25% UTP
25% 5-Ethyl-CTP + 75% CTP/25% 5-Methoxy-UTP + 75% UTP
25% 5-Ethyl-CTP + 75% CTP/75% 5-Methoxy-UTP + 25% UTP
25% 5-Ethynyl-CTP + 75% CTP/25% 5-Methoxy-UTP + 75% UTP
25% 5-Ethynyl-CTP + 75% CTP/75% 5-Methoxy-UTP + 25% UTP
25% 5-Fluoro-CTP + 75% CTP/25% 5-Methoxy-UTP + 75% UTP
25% 5-Fluoro-CTP + 75% CTP/75% 5-Methoxy-UTP + 25% UTP
25% 5-Formyl-CTP + 75% CTP/25% 5-Methoxy-UTP + 75% UTP
25% 5-Formyl-CTP + 75% CTP/75% 5-Methoxy-UTP + 25% UTP
25% 5-Hydroxymethyl-CTP + 75% CTP/25% 5-Methoxy-UTP + 75% UTP
25% 5-Hydroxymethyl-CTP + 75% CTP/75% 5-Methoxy-UTP + 25% UTP
25% 5-Iodo-CTP + 75% CTP/25% 5-Methoxy-UTP + 75% UTP
25% 5-Iodo-CTP + 75% CTP/75% 5-Methoxy-UTP + 25% UTP
25% 5-Methoxy-CTP + 75% CTP/25% 5-Methoxy-UTP + 75% UTP
25% 5-Methoxy-CTP + 75% CTP/75% 5-Methoxy-UTP + 25% UTP
25% 5-Methyl-CTP + 75% CTP/25% 5-Methoxy-UTP + 75% 1-Methyl-pseudo-UTP
25% 5-Methyl-CTP + 75% CTP/25% 5-Methoxy-UTP + 75% UTP
25% 5-Methyl-CTP + 75% CTP/50% 5-Methoxy-UTP + 50% 1-Methyl-pseudo-UTP
25% 5-Methyl-CTP + 75% CTP/50% 5-Methoxy-UTP + 50% UTP
25% 5-Methyl-CTP + 75% CTP/5-Methoxy-UTP
25% 5-Methyl-CTP + 75% CTP/75% 5-Methoxy-UTP + 25% 1-Methyl-pseudo-UTP
25% 5-Methyl-CTP + 75% CTP/75% 5-Methoxy-UTP + 25% UTP
25% 5-Phenyl-CTP + 75% CTP/25% 5-Methoxy-UTP + 75% UTP
25% 5-Phenyl-CTP + 75% CTP/75% 5-Methoxy-UTP + 25% UTP

TABLE 2-continued

Modified Nucleosides and Combinations Thereof

25% 5-Trifluoromethyl-CTP + 75% CTP/25% 5-Methoxy-UTP + 75% UTP
25% 5-Trifluoromethyl-CTP + 75% CTP/75% 5-Methoxy-UTP + 25% UTP
25% 5-Trifluoromethyl-CTP + 75% CTP/1-Methyl-pseudo-UTP
25% N4-Ac-CTP + 75% CTP/25% 5-Methoxy-UTP + 75% UTP
25% N4-Ac-CTP + 75% CTP/75% 5-Methoxy-UTP + 25% UTP
25% N4-Bz-CTP + 75% CTP/25% 5-Methoxy-UTP + 75% UTP
25% N4-Bz-CTP + 75% CTP/75% 5-Methoxy-UTP + 25% UTP
25% N4-Methyl-CTP + 75% CTP/25% 5-Methoxy-UTP + 75% UTP
25% N4-Methyl-CTP + 75% CTP/75% 5-Methoxy-UTP + 25% UTP
25% Pseudo-iso-CTP + 75% CTP/25% 5-Methoxy-UTP + 75% UTP
25% Pseudo-iso-CTP + 75% CTP/75% 5-Methoxy-UTP + 25% UTP
25% 5-Bromo-CTP/75% CTP/Pseudo-UTP
25% 5-methoxy-UTP/25% 5-methyl-CTP/ATP/GTP
25% 5-methoxy-UTP/5-methyl-CTP/ATP/GTP
25% 5-methoxy-UTP/75% 5-methyl-CTP/ATP/GTP
25% 5-methoxy-UTP/CTP/ATP/GTP
25% 5-metoxy-UTP/50% 5-methyl-CTP/ATP/GTP
2-Amino-ATP
2-Thio-CTP
2-thio-pseudouridine TP, ATP, GTP, CTP
2-Thio-pseudo-UTP
2-Thio-UTP
3-Methyl-CTP
3-Methyl-pseudo-UTP
4-Thio-UTP
50% 5-Bromo-CTP + 50% CTP/1-Methyl-pseudo-UTP
50% 5-Hydroxymethyl-CTP + 50% CTP/1-Methyl-pseudo-UTP
50% 5-methoxy-UTP/5-methyl-CTP/ATP/GTP
50% 5-Methyl-CTP + 50% CTP/25% 5-Methoxy-UTP + 75% 1-Methyl-pseudo-UTP
50% 5-Methyl-CTP + 50% CTP/25% 5-Methoxy-UTP + 75% UTP
50% 5-Methyl-CTP + 50% CTP/50% 5-Methoxy-UTP + 50% 1-Methyl-pseudo-UTP
50% 5-Methyl-CTP + 50% CTP/50% 5-Methoxy-UTP + 50% UTP
50% 5-Methyl-CTP + 50% CTP/5-Methoxy-UTP
50% 5-Methyl-CTP + 50% CTP/75% 5-Methoxy-UTP + 25% 1-Methyl-pseudo-UTP
50% 5-Methyl-CTP + 50% CTP/75% 5-Methoxy-UTP + 25% UTP
50% 5-Trifluoromethyl-CTP + 50% CTP/1-Methyl-pseudo-UTP
50% 5-Bromo-CTP/50% CTP/Pseudo-UTP
50% 5-methoxy-UTP/25% 5-methyl-CTP/ATP/GTP
50% 5-methoxy-UTP/50% 5-methyl-CTP/ATP/GTP
50% 5-methoxy-UTP/75% 5-methyl-CTP/ATP/GTP
50% 5-methoxy-UTP/CTP/ATP/GTP
5-Aminoallyl-CTP
5-Aminoallyl-CTP/5-Methoxy-UTP
5-Aminoallyl-UTP
5-Bromo-CTP
5-Bromo-CTP/5-Methoxy-UTP
5-Bromo-CTP/1-Methyl-pseudo-UTP
5-Bromo-CTP/Pseudo-UTP
5-bromocytidine TP, ATP, GTP, UTP
5-Bromo-UTP
5-Carboxy-CTP/5-Methoxy-UTP
5-Ethyl-CTP/5-Methoxy-UTP
5-Ethynyl-CTP/5-Methoxy-UTP
5-Fluoro-CTP/5-Methoxy-UTP
5-Formyl-CTP/5-Methoxy-UTP
5-Hydroxy-methyl-CTP/5-Methoxy-UTP
5-Hydroxymethyl-CTP
5-Hydroxymethyl-CTP/1-Methyl-pseudo-UTP
5-Hydroxymethyl-CTP/5-Methoxy-UTP
5-hydroxymethyl-cytidine TP, ATP, GTP, UTP
5-Iodo-CTP/5-Methoxy-UTP
5-Me-CTP/5-Methoxy-UTP
5-Methoxy carbonyl methyl-UTP
5-Methoxy-CTP/5-Methoxy-UTP
5-methoxy-uridine TP, ATP, GTP, UTP
5-methoxy-UTP
5-Methoxy-UTP
5-Methoxy-UTP/N6-Isopentenyl-ATP
5-methoxy-UTP/25% 5-methyl-CTP/ATP/GTP
5-methoxy-UTP/5-methyl-CTP/ATP/GTP
5-methoxy-UTP/75% 5-methyl-CTP/ATP/GTP
5-methoxy-UTP/CTP/ATP/GTP
5-Methyl-2-thio-UTP

TABLE 2-continued

Modified Nucleosides and Combinations Thereof

5-Methylaminomethyl-UTP
5-Methyl-CTP/5-Methoxy-UTP
5-Methyl-CTP/5-Methoxy-UTP(cap 0)
5-Methyl-CTP/5-Methoxy-UTP(No cap)
5-Methyl-CTP/25% 5-Methoxy-UTP + 75% 1-Methyl-pseudo-UTP
5-Methyl-CTP/25% 5-Methoxy-UTP + 75% UTP
5-Methyl-CTP/50% 5-Methoxy-UTP + 50% 1-Methyl-pseudo-UTP
5-Methyl-CTP/50% 5-Methoxy-UTP + 50% UTP
5-Methyl-CTP/5-Methoxy-UTP/N6-Me-ATP
5-Methyl-CTP/75% 5-Methoxy-UTP + 25% 1-Methyl-pseudo-UTP
5-Methyl-CTP/75% 5-Methoxy-UTP + 25% UTP
5-Phenyl-CTP/5-Methoxy-UTP
5-Trifluoro-methyl-CTP/5-Methoxy-UTP
5-Trifluoromethyl-CTP
5-Trifluoromethyl-CTP/5-Methoxy-UTP
5-Trifluoromethyl-CTP/1-Methyl-pseudo-UTP
5-Trifluoromethyl-CTP/Pseudo-UTP
5-Trifluoromethyl-UTP
5-trifluromethylcytidine TP, ATP, GTP, UTP
75% 5-Aminoallyl-CTP + 25% CTP/25% 5-Methoxy-UTP + 75% UTP
75% 5-Aminoallyl-CTP + 25% CTP/75% 5-Methoxy-UTP + 25% UTP
75% 5-Bromo-CTP + 25% CTP/25% 5-Methoxy-UTP + 75% UTP
75% 5-Bromo-CTP + 25% CTP/75% 5-Methoxy-UTP + 25% UTP
75% 5-Carboxy-CTP + 25% CTP/25% 5-Methoxy-UTP + 75% UTP
75% 5-Carboxy-CTP + 25% CTP/75% 5-Methoxy-UTP + 25% UTP
75% 5-Ethyl-CTP + 25% CTP/25% 5-Methoxy-UTP + 75% UTP
75% 5-Ethyl-CTP + 25% CTP/75% 5-Methoxy-UTP + 25% UTP
75% 5-Ethynyl-CTP + 25% CTP/25% 5-Methoxy-UTP + 75% UTP
75% 5-Ethynyl-CTP + 25% CTP/75% 5-Methoxy-UTP + 25% UTP
75% 5-Fluoro-CTP + 25% CTP/25% 5-Methoxy-UTP + 75% UTP
75% 5-Fluoro-CTP + 25% CTP/75% 5-Methoxy-UTP + 25% UTP
75% 5-Formyl-CTP + 25% CTP/25% 5-Methoxy-UTP + 75% UTP
75% 5-Formyl-CTP + 25% CTP/75% 5-Methoxy-UTP + 25% UTP
75% 5-Hydroxymethyl-CTP + 25% CTP/25% 5-Methoxy-UTP + 75% UTP
75% 5-Hydroxymethyl-CTP + 25% CTP/75% 5-Methoxy-UTP + 25% UTP
75% 5-Iodo-CTP + 25% CTP/25% 5-Methoxy-UTP + 75% UTP
75% 5-Iodo-CTP + 25% CTP/75% 5-Methoxy-UTP + 25% UTP
75% 5-Methoxy-CTP + 25% CTP/25% 5-Methoxy-UTP + 75% UTP
75% 5-Methoxy-CTP + 25% CTP/75% 5-Methoxy-UTP + 25% UTP
75% 5-methoxy-UTP/5-methyl-CTP/ATP/GTP
75% 5-Methyl-CTP + 25% CTP/25% 5-Methoxy-UTP + 75% 1-Methyl-pseudo-UTP
75% 5-Methyl-CTP + 25% CTP/25% 5-Methoxy-UTP + 75% UTP
75% 5-Methyl-CTP + 25% CTP/50% 5-Methoxy-UTP + 50% 1-Methyl-pseudo-UTP
75% 5-Methyl-CTP + 25% CTP/50% 5-Methoxy-UTP + 50% UTP
75% 5-Methyl-CTP + 25% CTP/5-Methoxy-UTP
75% 5-Methyl-CTP + 25% CTP/75% 5-Methoxy-UTP + 25% 1-Methyl-pseudo-UTP
75% 5-Methyl-CTP + 25% CTP/75% 5-Methoxy-UTP + 25% UTP
75% 5-Phenyl-CTP + 25% CTP/25% 5-Methoxy-UTP + 75% UTP
75% 5-Phenyl-CTP + 25% CTP/75% 5-Methoxy-UTP + 25% UTP
75% 5-Trifluoromethyl-CTP + 25% CTP/25% 5-Methoxy-UTP + 75% UTP
75% 5-Trifluoromethyl-CTP + 25% CTP/75% 5-Methoxy-UTP + 25% UTP
75% 5-Trifluoromethyl-CTP + 25% CTP/1-Methyl-pseudo-UTP
75% N4-Ac-CTP + 25% CTP/25% 5-Methoxy-UTP + 75% UTP
75% N4-Ac-CTP + 25% CTP/75% 5-Methoxy-UTP + 25% UTP
75% N4-Bz-CTP + 25% CTP/25% 5-Methoxy-UTP + 75% UTP
75% N4-Bz-CTP + 25% CTP/75% 5-Methoxy-UTP + 25% UTP
75% N4-Methyl-CTP + 25% CTP/25% 5-Methoxy-UTP + 75% UTP
75% N4-Methyl-CTP + 25% CTP/75% 5-Methoxy-UTP + 25% UTP
75% Pseudo-iso-CTP + 25% CTP/25% 5-Methoxy-UTP + 75% UTP
75% Pseudo-iso-CTP + 25% CTP/75% 5-Methoxy-UTP + 25% UTP
75% 5-Bromo-CTP/25% CTP/1-Methyl-pseudo-UTP
75% 5-Bromo-CTP/25% CTP/Pseudo-UTP
75% 5-methoxy-UTP/25% 5-methyl-CTP/ATP/GTP
75% 5-methoxy-UTP/50% 5-methyl-CTP/ATP/GTP
75% 5-methoxy-UTP/75% 5-methyl-CTP/ATP/GTP
75% 5-methoxy-UTP/CTP/ATP/GTP
8-Aza-ATP
Alpha-thio-CTP
CTP/25% 5-Methoxy-UTP + 75% 1-Methyl-pseudo-UTP
CTP/25% 5-Methoxy-UTP + 75% UTP
CTP/50% 5-Methoxy-UTP + 50% 1-Methyl-pseudo-UTP

TABLE 2-continued

Modified Nucleosides and Combinations Thereof

CTP/50% 5-Methoxy-UTP + 50% UTP
CTP/5-Methoxy-UTP
CTP/5-Methoxy-UTP (cap 0)
CTP/5-Methoxy-UTP(No cap)
CTP/75% 5-Methoxy-UTP + 25% 1-Methyl-pseudo-UTP
CTP/75% 5-Methoxy-UTP + 25% UTP
CTP/UTP(No cap)
N1-Me-GTP
N4-Ac-CTP
N4Ac-CTP/1-Methyl-pseudo-UTP
N4Ac-CTP/5-Methoxy-UTP
N4-acetyl-cytidine TP, ATP, GTP, UTP
N4-Bz-CTP/5-Methoxy-UTP
N4-methyl CTP
N4-Methyl-CTP/5-Methoxy-UTP
Pseudo-iso-CTP/5-Methoxy-UTP
PseudoU-alpha-thio-TP
pseudouridine TP, ATP, GTP, CTP
pseudo-UTP/5-methyl-CTP/ATP/GTP
UTP-5-oxyacetic acid Me ester
Xanthosine According to the disclosure, polynucleotides of the disclosure may be synthesized to comprise the combinations or single modifications of Table 1 or Table 2.

Where a single modification is listed, the listed nucleoside or nucleotide represents 100 percent of that A, U, G or C nucleotide or nucleoside having been modified. Where percentages are listed, these represent the percentage of that particular A, U, G or C nucleobase triphosphate of the total amount of A, U, G, or C triphosphate present. For example, the combination: 25% 5-Aminoallyl-CTP+75% CTP/25% 5-Methoxy-UTP+75% UTP refers to a polynucleotide where 25% of the cytosine triphosphates are 5-Aminoallyl-CTP while 75% of the cytosines are CTP; whereas 25% of the uracils are 5-methoxy UTP while 75% of the uracils are UTP. Where no modified UTP is listed then the naturally occurring ATP, UTP, GTP and/or CTP is used at 100% of the sites of those nucleotides found in the polynucleotide. In this example all of the GTP and ATP nucleotides are left unmodified.

Methods of Making RLR Agonists

RLR agonists of the present disclosure may be produced by means available in the art, including but not limited to in vitro transcription (IVT) and synthetic methods. Enzymatic (IVT), solid-phase, liquid-phase, combined synthetic methods, small region synthesis, and ligation methods may be utilized. In one embodiment, RLR agonists are made using IVT enzymatic synthesis methods. Methods of making polynucleotides by IVT are known in the art and are described in International Application PCT/US2013/30062, the contents of which are incorporated herein by reference in their entirety. Accordingly, the present disclosure also includes polynucleotides, e.g., DNA, constructs and vectors that may be used to in vitro transcribe an RLR agonist described herein.

Non-natural modified nucleobases may be introduced into polynucleotides, e.g., RNA, during synthesis or post-synthesis. In certain embodiments, modifications may be on internucleoside linkages, purine or pyrimidine bases, or sugar. In particular embodiments, the modification may be introduced at the terminal of a polynucleotide chain or anywhere else in the polynucleotide chain; with chemical synthesis or with a polymerase enzyme. Examples of modified nucleic acids and their synthesis are disclosed in PCT application No. PCT/US2012/058519. Synthesis of modified polynucleotides is also described in Verma and Eckstein, Annual Review of Biochemistry, vol. 76, 99-134 (1998).

Either enzymatic or chemical ligation methods may be used to conjugate polynucleotides or their regions with different functional moieties, such as targeting or delivery agents, fluorescent labels, liquids, nanoparticles, etc. Conjugates of polynucleotides and modified polynucleotides are reviewed in Goodchild, Bioconjugate Chemistry, vol. 1(3), 165-187 (1990). The synthesis of oligonucleotides, polynucleotides, and conjugations and ligations thereof, is further described in Taskova et al., (2017) Chembiochem 18(17):1671-1682; Gooding et al., (2016) Eur J Pharm Biopharm 107:321-40; Menzi et al., (2015) Future Med Chem 7(13):1733-49; Winkler J., (2013) Ther Deliv. (7): 791-809; Singh et al., (2010) Chem Soc Rev 39(6):2054-70; and Lu et al., (2010) Bioconjug Chem 21(2):187-202.

Pharmaceutical Compositions and Formulations

In certain embodiments, the invention provides for a pharmaceutical composition comprising an RLR agonist with a pharmaceutically acceptable diluent, carrier, solubilizer, emulsifier, preservative and/or adjuvant.

In certain embodiments, acceptable formulation materials preferably are nontoxic to recipients at the dosages and concentrations employed. In certain embodiments, the formulation material(s) are for s.c. and/or I.V. administration. In certain embodiments, the pharmaceutical composition can contain formulation materials for modifying, maintaining or preserving, for example, the pH, osmolality, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In certain embodiments, the formulation comprises PBS; 20 mM NaOAC, pH 5.2, 50 mM NaCl; and/or 10 mM NAOAC, pH 5.2, 9% Sucrose. In certain embodiments, the optimal pharmaceutical composition will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and/or rate of in vivo clearance of the RLR agonist.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In certain embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising an RLR agonist can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising an RLR agonist can be formulated as a lyophilizate using appropriate excipients such as sucrose.

In certain embodiments, the pharmaceutical composition can be selected for parenteral delivery. In certain embodiments, the compositions can be selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising an RLR agonist, in a pharmaceutically acceptable vehicle. In certain embodiments, a vehicle for parenteral injection is sterile distilled water in which an RLR agonist is formulated as a sterile, isotonic solution, and properly preserved. In certain embodiments, the preparation can involve the formulation of the desired molecule with a delivery vehicle or agent, such as injectable microspheres, bio-erodible particles, polymeric compounds (such as polylactic acid, polyglycolic acid or polyethylenimine (e.g. JetPEI®)), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition can be formulated for inhalation. In certain embodiments, an RLR agonist can be formulated as a dry powder for inhalation. In certain embodiments, an inhalation solution comprising an RLR agonist can be formulated with a propellant for aerosol delivery. In certain embodiments, solutions can be nebulized. Pulmonary administration is further described in PCT application No. PCT/US94/001875, which describes pulmonary delivery of chemically modified proteins.

In certain embodiments, it is contemplated that formulations can be administered orally. In certain embodiments, an RLR agonist that is administered in this fashion can be formulated with or without those carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized. In certain embodiments, at least one additional agent can be included to facilitate absorption of an RLR agonist. In certain embodiments, diluents, flavorings, low melting point waxes, vegetable oils, lubricants, suspending agents, tablet disintegrating agents, and binders can also be employed.

In certain embodiments, a pharmaceutical composition can involve an effective quantity of an RLR agonist in a mixture with non-toxic excipients which are suitable for the manufacture of tablets. In certain embodiments, by dissolving the tablets in sterile water, or another appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving an RLR agonist in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15: 167-277 (1981) and Langer, Chem. Tech., 12:98-105 (1982)), ethylene vinyl acetate (Langer et al., supra) or poly-D(−)-3-hydroxybutyric acid (EP 133,988). In certain embodiments, sustained release compositions can also include liposomes, which can be prepared by any of several methods known in the art. See, e.g., Eppstein et al, Proc. Natl. Acad. Sci. USA, 82:3688-3692 (1985); EP 036,676; EP 088,046 and EP 143,949.

The pharmaceutical composition to be used for in vivo administration typically is sterile. In certain embodiments, this can be accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising an RLR agonist to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which an RLR agonist is being used, the route of administration, and the size (body weight, body surface or organ size) and/or condition (the age and general health) of the patient. In certain embodiments, the clinician can titer the dosage and modify the route of administration to obtain the optimal therapeutic effect.

In certain embodiments, the frequency of dosing will take into account the pharmacokinetic parameters of an RLR agonist in the formulation used. In certain embodiments, a clinician will administer the composition until a dosage is reached that achieves the desired effect. In certain embodiments, the composition can therefore be administered as a single dose or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intraocular, intraarterial, intraportal, or intralesional routes; by sustained release systems or by implantation devices. In certain embodiments, the compositions can be administered by bolus injection or continuously by infusion, or by implantation device. In certain embodiments, individual elements of the combination therapy may be administered by different routes.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration. In certain embodiments, it can be desirable to use a pharmaceutical composition comprising an RLR agonist in an ex vivo manner. In such instances, cells, tissues and/or organs that have been removed from the patient are exposed to a pharmaceutical composition comprising an RLR agonist after which the cells, tissues and/or organs are subsequently implanted back into the patient.

In certain embodiments, an RLR agonist can be delivered by implanting certain cells that have been genetically engineered, using methods such as those described herein, to express and secrete the agonist. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

In some aspects, the disclosure provides a pharmaceutical composition comprising an RLR agonist according to the disclosure for stimulating an immune response, treating or delaying progression of a cancer, or reducing or inhibiting tumor growth in a subject in need thereof, and a pharmaceutically acceptable carrier. In some embodiments, the RLR agonist is formulated in a polyethylenimine (PEI) carrier. In some embodiments, the PEI carrier is JetPEI®.

Applications

The compositions described herein can be used in diagnostic and therapeutic applications. For example, detectably-labeled RLR agonists can be used in assays to detect the presence or amount of the target protein in a sample (e.g., a biological sample). The compositions can be used in in vitro assays for studying inhibition of target function (e.g. RLR-mediated cellular signaling or response). In some embodiments, e.g., in which the compositions bind to and activate a target (e.g. a protein or polypeptide), the compositions can be used as positive controls in assays designed to identify additional novel compounds that also induce activity of the target protein or polypeptide and/or are otherwise are useful for treating a disorder associated with the target protein or polypeptide. For example, a RLR-activating composition can be used as a positive control in an assay to identify additional compounds (e.g., small molecules, aptamers, or antibodies) that induce, increase, or stimulate RLR function. The compositions can also be used in therapeutic methods as elaborated on below.

Kits

A kit can include an RLR agonist as disclosed herein, and instructions for use. The kits may comprise, in a suitable container, an RLR agonist, one or more controls, and various buffers, reagents, enzymes and other standard ingredients well known in the art.

The container can include at least one vial, well, test tube, flask, bottle, syringe, or other container means, into which an RLR agonist may be placed, and in some instances, suitably aliquoted. Where an additional component is provided, the kit can contain additional containers into which this component may be placed. The kits can also include a means for containing an RLR agonist and any other reagent containers in close confinement for commercial sale. Such containers may include injection or blow-molded plastic containers into which the desired vials are retained. Containers and/or kits can include labeling with instructions for use and/or warnings.

In some aspects, the disclosure provides a kit comprising an RLR agonist provided by the disclosure, or comprising a pharmaceutical composition provided by the disclosure and instructions for use in stimulating an immune response in a subject, or treating or delaying progression of a cancer, or inhibiting tumor growth in a subject, optionally with instructions for use in combination with one or more additional therapeutic agents.

In some embodiments, the agonist or pharmaceutical composition is administered in combination with one or more additional therapeutic agents, wherein the one or more additional therapeutic agents is selected from the group consisting of: a chemotherapy, a targeted anti-cancer therapy, an oncolytic drug, a cell death-inducing agent, an opsonizing agent (e.g., an opsonizing antibody) a cytotoxic agent, an immune-based therapy, a cytokine, an activator of a costimulatory molecule, an inhibitor of an inhibitory molecule, a vaccine, a cellular immunotherapy, or a combination thereof.

In some embodiments, the RLR agonist or pharmaceutical composition is administered preceding or subsequent to administration of the one or more additional therapeutic agents or wherein the one or more additional therapeutic agents is administered concurrently with, preceding or subsequent to the administration of the RLR agonist or pharmaceutical composition.

In some embodiments, the one or more additional therapeutic agents is a PD-1/PD-L1 antagonist, a TIM-3 antagonist, a VISTA antagonist, an adenosine A2AR antagonist, a B7-H3 antagonist, a B7-H4 antagonist, a BTLA antagonist, a CTLA-4 antagonist, an IDO antagonist, a KIR antagonist, a LAG-3 antagonist, a toll-like receptor 3 (TLR3) agonist, a toll-like receptor 7 (TLR7) agonist, a toll-like receptor 9 (TLR9) agonist.

In some embodiments, the one or more additional therapeutic agents is an agonist comprising an polypeptide (e.g, antibody, or antigen binding portion thereof) that specifically binds to CD137 (4-1BB).

In some embodiments, the one or more additional therapeutic agents is an agonist comprising an polypeptide (e.g., antibody, or antigen binding portion thereof) that specifically binds to CD134 (OX40).

Methods of Use

The compositions of the present invention have numerous in vitro and in vivo utilities involving the detection and/or quantification of RLRs and/or the agonism of RLR function.

The above-described compositions are useful in, inter alia, methods for treating or preventing a variety of cancers or infectious diseases in a subject. The compositions can be administered to a subject, e.g., a human subject, using a variety of methods that depend, in part, on the route of administration. The route can be, e.g., intravenous injection or infusion (IV), subcutaneous injection (SC), intradermal injection (ID), intraperitoneal (IP) injection, intramuscular injection (IM), intratumoral injection (IT) or intrathecal injection. The injection can be in a bolus or a continuous infusion.

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223; U.S. Pat. Nos. 5,501,856; 4,863,457; and 3,710,795; EP488401; and EP 430539, the disclosures of each of which are incorporated herein by reference in their entirety. The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

In some embodiments, an RLR agonist is therapeutically delivered to a subject by way of local administration.

A suitable dose of an RLR agonist described herein, which dose is capable of treating or preventing cancer in a subject, can depend on a variety of factors including, e.g., the age, sex, and weight of a subject to be treated and the particular inhibitor compound used. Other factors affecting the dose administered to the subject include, e.g., the type or severity of the cancer or infectious disease. For example, a subject having metastatic melanoma may require administration of a different dosage of an RLR agonist than a subject with glioblastoma. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject will also depend upon the judgment of the treating medical practitioner (e.g., doctor or nurse). Suitable dosages are described herein.

A pharmaceutical composition can include a therapeutically effective amount of an RLR agonist thereof described herein. Such effective amounts can be readily determined by one of ordinary skill in the art based, in part, on the effect of the administered RLR agonist, or the combinatorial effect of the RLR agonist and one or more additional active agents, if more than one agent is used. A therapeutically effective amount of an RLR agonist described herein can also vary according to factors such as the disease state, age, sex, and weight of the individual, and the ability of the agonist (and one or more additional active agents) to elicit a desired response in the individual, e.g., reduction in tumor growth. For example, a therapeutically effective amount of an RLR agonist can inhibit (lessen the severity of or eliminate the occurrence of) and/or prevent a particular disorder, and/or any one of the symptoms of the particular disorder known in the art or described herein. A therapeutically effective amount is also one in which any toxic or detrimental effects of the composition are outweighed by the therapeutically beneficial effects.

Suitable human doses of any of the RLR agonists described herein can further be evaluated in, e.g., Phase I dose escalation studies. See, e.g., van Gurp et al. (2008) *Am J Transplantation* 8 (8): 1711-1718; Hanouska et al. (2007) *Clin Cancer Res* 13(2, part 1):523-531; and Hetherington et al. (2006) *Antimicrobial Agents and Chemotherapy* 50(10): 3499-3500.

In some embodiments, the composition contains any of the RLR agonists described herein and one or more (e.g., two, three, four, five, six, seven, eight, nine, 10, or 11 or more) additional therapeutic agents such that the composition as a whole is therapeutically effective. For example, a composition can contain an RLR agonist described herein and an alkylating agent, wherein the agonist and agent are each at a concentration that when combined are therapeutically effective for treating or preventing a cancer (e.g., melanoma) in a subject.

Toxicity and therapeutic efficacy of such compositions can be determined by known pharmaceutical procedures in cell cultures or experimental animals (e.g., animal models of any of the cancers described herein). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. An RLR agonist that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. For an RLR agonist described herein, the therapeutically effective dose can be estimated initially from cell culture assays. A dose can be formulated in animal models to achieve a circulating plasma concentration range that includes the $EC_{50}$ (i.e., the concentration of the agonist which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration (e.g., to the eye or a joint) is desired, cell culture or animal modeling can be used to determine a dose required to achieve a therapeutically effective concentration within the local site.

In some embodiments, the methods can be performed in conjunction with other therapies for cancer or infectious disease. For example, the composition can be administered to a subject at the same time, prior to, or after, radiation, surgery, targeted or cytotoxic chemotherapy, chemoradiotherapy, hormone therapy, immunotherapy, gene therapy, cell transplant therapy, precision medicine, genome editing therapy, or other pharmacotherapy.

As described above, the compositions described herein (e.g., RLR agonist compositions) can be used to treat a variety of cancers such as but not limited to: Kaposi's sarcoma, leukemia, acute lymphocytic leukemia, acute myelocytic leukemia, myeloblasts promyelocyte myelomonocytic monocytic erythroleukemia, chronic leukemia, chronic myelocytic (granulocytic) leukemia, chronic lymphocytic leukemia, mantle cell lymphoma, primary central nervous system lymphoma, Burkitt's lymphoma, marginal zone B cell lymphoma, polycythemia vera, Hodgkin's disease, non-Hodgkin's disease, multiple myeloma, Waldenstrom's macroglobulinemia, heavy chain disease, solid tumors, sarcomas, and carcinomas, fibrosarcoma, myxosarcoma, liposarcoma, chrondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon sarcoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, esophageal carcinoma, basal cell carcinoma, biliary tract cancer, bladder cancer, bone cancer, brain and central nervous system (CNS) cancer, cervical cancer, choriocarcinoma, colorectal cancers, connective tissue cancer, cancer of the digestive system, endometrial cancer, esophageal cancer, eye cancer, head and neck cancer, gastric cancer, intraepithelial neoplasm, kidney cancer, larynx cancer, liver cancer, lung cancer (small cell, large cell), melanoma, neuroblastoma; oral cavity cancer (for example lip, tongue, mouth and pharynx), ovarian cancer, pancreatic cancer, rectal cancer; cancer of the respiratory system, sarcoma, skin cancer, stomach cancer, testicular cancer, thyroid cancer, uterine cancer, and cancer of the urinary system.

In some aspects, the disclosure provides a method to increase RLR-mediated production of one or more cytokines in a cell, the method comprising contacting the cell with an RLR agonist provided by the disclosure, wherein the agonist increases RLR-mediated cytokine production in a cell.

In some aspects, the disclosure provides a method to increase RLR-mediated expression of one or more interferon-stimulated genes in a cell, the method comprising contacting the cell with an RLR agonist provided by the disclosure, wherein the agonist increases RLR-mediated expression of one or more interferon-stimulated genes in a cell.

In some aspects, the disclosure provides a method to increase RLR-dependent intracellular signaling in a cell, the method comprising contacting the cell with an RLR agonist provided by the disclosure, wherein the agonist increases RLR-dependent intracellular signaling.

In some aspects, the disclosure provides a method of stimulating an immune response in a subject, the method comprising administering to the subject an effective amount of an RLR agonist provided by the disclosure, or a pharmaceutical composition provided by the disclosure.

In some aspects, the disclosure provides a method of treating or delaying progression of a cancer in a subject, the method comprising administering to the subject an effective amount of an RLR agonist provided by the disclosure, or a pharmaceutical composition provided by the disclosure.

In some aspects, the disclosure provides a method of reducing or inhibiting tumor growth in a subject in need thereof, the method comprising administering to the subject an effective amount of an RLR agonist provided by the disclosure, or a pharmaceutical composition provided by the disclosure.

In some aspects, the disclosure provides a method for stimulating an immune response, treating or delaying progression of a cancer, or inhibiting tumor growth in a subject in need thereof, the method comprising administering to the subject an effective amount of an RLR agonist provided by the disclosure, or a pharmaceutical composition provided by the disclosure, wherein the agonist, or the pharmaceutical composition increases RLR-mediated production of one or more cytokines in a cell, increases RLR-mediated expression of one or more interferon-stimulated genes in a cell, and or increases RLR-dependent intracellular signaling in a cell, thereby stimulating the immune response, treating or delaying progression of the cancer, or inhibiting growth of the tumor.

Combinations of RLR Agonists with Additional Therapeutic Agents

In some embodiments, an RLR agonist described herein can be administered to a subject as a monotherapy. Alternatively, the RLR agonist can be administered to a subject as a combination therapy with another treatment, e.g., another treatment for a cancer. For example, the combination therapy can include administering to the subject (e.g., a human patient) one or more additional agents that provide a therapeutic benefit to a subject who has, or is at risk of developing, cancer.

In some embodiments of the methods provided by the disclosure, the RLR agonist or pharmaceutical composition is administered in combination with one or more additional therapeutic agents, wherein the one or more additional therapeutic agents is selected from the group consisting of: a chemotherapy, a targeted anti-cancer therapy, an oncolytic drug, a cell death-inducing agent, an opsonizing agent (e.g., an opsonizing antibody) a cytotoxic agent, an immune-based therapy, a cytokine, an activator or agonist of a costimulatory molecule, an inhibitor of an inhibitory molecule, a vaccine, a cellular immunotherapy, or a combination thereof.

In some embodiments, the RLR agonist or pharmaceutical composition is administered preceding or subsequent to administration of the one or more additional therapeutic agents or wherein the one or more additional therapeutic agents is administered concurrently with, preceding or subsequent to the administration of the agonist or pharmaceutical composition.

In some embodiments, the one or more additional therapeutic agents is a PD-1/PD-L1 antagonist, a TIM-3 antagonist, a VISTA antagonist, an adenosine A2AR antagonist, a B7-H3 antagonist, a B7-H4 antagonist, a BTLA antagonist, a CTLA-4 antagonist, an IDO antagonist, a KIR antagonist, a LAG-3 antagonist, a toll-like receptor 3 (TLR3) agonist, a toll-like receptor 7 (TLR7) agonist, a toll-like receptor 9 (TLR9) agonist.

Combination with Chemotherapeutic Agents

Chemotherapeutic agents suitable for combination and/or co-administration with compositions of the present invention include, for example: taxol, cytochalasin B, gramicidin D, ethidium bromide, emetine, mitomycin, etoposide, tenoposide, vincristine, vinblastine, colchicin, doxorubicin, daunorubicin, dihydroxyanthrancindione, mitoxantrone, mithramycin, actinomycin D, 1-dehydrotestosterone, glucocorticoids, procaine, tetracaine, lidocaine, propranolol, and puromycin and analogs or homologs thereof. Further agents include, for example, antimetabolites (e.g., methotrexate, 6-mercaptopurine, 6-thioguanine, cytarabine, 5-fluorouracil decarbazine), alkylating agents (e.g. mechlorethamine, thio-TEPA, chlorambucil, melphalan, carmustine (BSNU), lomustine (CCNU), cyclophosphamide, busulfan, dibromomannitol, streptozotocin, mitomycin C, cis-dichlordiamine platinum (II) (DDP), procarbazine, altretamine, cisplatin, carboplatin, oxaliplatin, nedaplatin, satraplatin, or triplatin tetranitrate), anthracycline (e.g. daunorubicin (formerly daunomycin) and doxorubicin), antibiotics (e.g. dactinomcin (formerly actinomycin), bleomycin, mithramycin, and anthramycin (AMC)), and anti-mitotic agents (e.g. vincristine and vinblastine) and temozolomide.

Combination with PD-1/PD-L1 Antagonists

In some embodiments, a RLR agonist, or pharmaceutical compositions thereof, provided by the disclosure is combined (e.g., administered in combination) with one or more PD-1/PD-L1 antagonist that specifically binds to human PD-1 or PD-L1 and inhibits PD-1/PD-L1 biological activity and/or downstream pathway(s) and/or cellular processed mediated by human PD-1/PD-L1 signaling or other human PD-1/PD-L1-mediated functions.

Accordingly, provided herein are PD-1/PD-L1 antagonists that directly or allosterically block, antagonize, suppress, inhibit or reduce PD-1/PD-L1 biological activity, including downstream pathways and/or cellular processes mediated by PD-1/PD-L1 signaling, such as receptor binding and/or elicitation of a cellular response to PD-1/PD-L1. Also provided herein are PD-1/PD-L1 antagonists that reduce the quantity or amount of human PD-1 or PD-L1 produced by a cell or subject.

In some embodiments, the disclosure provides a PD-1/PD-L1 antagonist that binds human PD-1 and prevents, inhibits or reduces PD-L1 binding to PD-1. In some aspects, the PD-1/PD-L1 antagonist binds to the mRNA encoding PD-1 or PD-L1 and prevents translation. In some embodiments, the PD-1/PD-L1 antagonist binds to the mRNA encoding PD-1 or PD-L1 and causes degradation and/or turnover.

In some embodiments, the PD-1/PD-L1 antagonist inhibits PD-1 signaling or function. In some embodiments, the PD-1/PD-L1 antagonist blocks binding of PD-1 to PD-L1, PD-L2, or to both PD-L1 and PD-L2. In some embodiments, the PD-1/PD-L1 antagonist blocks binding of PD-1 to PD-L1. In some embodiments, the PD-1/PD-L1 antagonist blocks binding of PD-1 to PD-L2. In some embodiments, the PD-1/PD-L1 antagonist blocks the binding of PD-1 to PD-L1 and PD-L2. In some embodiments, the PD-1/PD-L1 antagonist specifically binds PD-1. In some embodiments, the PD-1/PD-L1 antagonist specifically binds PD-L1. In some embodiments, the PD-1/PD-L1 antagonist specifically binds PD-L2.

In some embodiments, the PD-1/PD-L1 antagonist inhibits the binding of PD-1 to its cognate ligand. In some embodiments, the PD-1/PD-L1 antagonist inhibits the binding of PD-1 to PD-L1, PD-1 to PD-L2, or PD-1 to both PD-L1 and PD-L2. In some embodiments, the PD-1/PD-L1 antagonist does not inhibit the binding of PD-1 to its cognate ligand.

In some embodiments, the PD-1/PD-L1 antagonist is an isolated monoclonal antibody (mAb), or antigen binding fragment thereof, which specifically binds to PD-1 or PD-L1. In some embodiments, the PD-1/PD-L1 antagonist is an antibody or antigen binding fragment thereof that specifically binds to human PD-1. In some embodiments, the PD-1/PD-L1 antagonist is an antibody or antigen binding fragment thereof that specifically binds to human PD-L1. In some embodiments, the PD-1/PD-L1 antagonist is an antibody or antigen binding fragment that binds to human PD-L1 and inhibits the binding of PD-L1 to PD-1. In some embodiments, the PD-1/PD-L1 antagonist is an antibody or antigen binding fragment that binds to human PD-1 and inhibits the binding of PD-L1 to PD-1.

Several immune checkpoint antagonists that inhibit or disrupt the interaction between PD-1 and either one or both of its ligands PD-L1 and PD-L2 are in clinical development or are currently available to clinicians for treating cancer.

Examples of anti-human PD-1 monoclonal antibodies, or antigen binding fragments thereof, that may comprise the PD-1/PD-L1 antagonist in any of the compositions, methods, and uses provided by the disclosure include, but are not limited to: KEYTRUDA® (pembrolizumab, MK-3475, h409A11; see U.S. Pat. Nos. 8,952,136, 8,354,509, 8,900,587, and EP2170959, all of which are included herein by reference in their entirety; Merck), OPDIVO® (nivolumab, BMS-936558, MDX-1106, ONO-4538; see U.S. Pat. Nos. 7,595,048, 8,728,474, 9,073,994, 9,067,999, EP1537878, U.S. Pat. Nos. 8,008,449, 8,779,105, and EP2161336, all of which are included herein by reference in their entirety; Bristol Myers Squibb), MEDI0680 (AMP-514), BGB-A317 and BGB-108 (BeiGene), 244C8 and 388D4 (see WO2016106159, which is incorporated herein by reference in its entirety; Enumeral Biomedical), PDR001 (Novartis), and REGN2810 (Regeneron). Accordingly, in some embodiments the PD-1/PD-L1 antagonist is pembrolizumab. In some embodiments, the PD-1/PD-L1 antagonist is nivolumab.

Examples of anti-human PD-L1 monoclonal antibodies, or antigen binding fragments thereof, that may comprise the PD-1/PD-L1 antagonist in any of the compositions, methods, and uses provided by the disclosure include, but are not limited to: BAVENCIO® (avelumab, MSB0010718C, see WO2013/79174, which is incorporated herein by reference in its entirety; Merck/Pfizer), IMFINZI® (durvalumab, MEDI4736), TECENTRIQ® (atezolizumab, MPDL3280A, RG7446; see WO2010/077634, which is incorporated herein by reference in its entirety; Roche), MDX-1105 (BMS-936559, 12A4; see U.S. Pat. No. 7,943,743 and WO2013/173223, both of which are incorporated herein by reference in their entirety; Medarex/BMS), and FAZ053 (Novartis). Accordingly, in some embodiments the PD-1/PD-L1 antagonist is avelumab. In some embodiments, the PD-1/PD-L1 antagonist is durvalumab. In some embodiments, the PD-1/PD-L1 antagonist is atezolizumab.

In some embodiments, the PD-1/PD-L1 antagonist is an immunoadhesin that specifically bind to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342, both of which are incorporated herein by reference in their entirety. In some embodiments, the PD-1/PD-L1 antagonist is AMP-224 (also known as B7-DCIg), which is a PD-L2-FC fusion protein that specifically binds to human PD-1.

It will be understood by one of ordinary skill that any PD-1/PD-L1 antagonist which binds to PD-1 or PD-L1 and disrupts the PD-1/PD-L1 signaling pathway, is suitable for compositions, methods, and uses disclosed herein.

In some embodiments, the PD-1/PD-L1 antagonist is a small molecule, a nucleic acid, a peptide, a peptide mimetic, a protein, a carbohydrate, a carbohydrate derivative, or a glycopolymer. Exemplary small molecule PD-1 inhibitors are described in Zhan et al., (2016) Drug Discov Today 21(6):1027-1036.

In some embodiments of the methods provided by the disclosure, the RLR agonist is combined with a PD-1/PD-L1 antagonist, wherein the PD-1/PD-L1 antagonist is selected from the group consisting of: PDR001, KEYTRUDA® (pembrolizumab), OPDIVO® (nivolumab), pidilizumab, MEDI0680, REGN2810, TSR-042, PF-06801591, and AMP-224. In some embodiments, the PD-1/PD-L1 antagonist is selected from the group consisting of: FAZ053, TENCENTRIQ® (atezolizumab), BAVENCIO® (avelumab), IMFINZI® (durvalumab), and BMS-936559.

Combinations with TIM-3 Antagonist

In some embodiments, an RLR agonist, or pharmaceutical compositions thereof, provided by the disclosure is combined (e.g., administered in combination) with a TIM-3 antagonist. The TIM-3 antagonist may be an antibody, an antigen binding fragment thereof, an immunoadhesin, a fusion protein, or an oligopeptide. In some embodiments, the TIM-3 antagonist is chosen from MGB453 (Novartis), TSR-022 (Tesaro), or LY3321367 (Eli Lilly).

Combinations with LAG-3 Antagonist

In some embodiments, an RLR agonist, or pharmaceutical compositions thereof, provided by the disclosure is combined (e.g., administered in combination) with a LAG-3 antagonist. The LAG-3 antagonist may be an antibody, an antigen binding fragment thereof, an immunoadhesin, a fusion protein, or oligopeptide. In some embodiments, the LAG-3 inhibitor is chosen from LAG525 (Novartis), BMS-986016 (Bristol-Myers Squibb), TSR-033 (Tesaro), MK-4280 (Merck & Co), or REGN3767 (Regeneron).

Combinations with Toll-Like Receptor (TLR) Agonists

In some embodiments, an RLR agonist, or pharmaceutical composition thereof, provided by the disclosure is combined (e.g. administered in combination) with a TLR agonist.

Toll-like receptors (TLRs) are a family of germline-encoded transmembrane proteins that facilitate pathogen recognition and activation of the innate immune system. (Hoffmann et al., (1999) Science 284:1313-1318; Rock et al., (1998) Proc Natl Acad Sci USA 95:588-593). TLRs are pattern recognition receptors (PRRs), and are expressed by cells of the innate immune system. Examples of known ligands for TLRs include gram positive bacteria (TLR-2), bacterial endotoxin (TLR-4), flagellin protein (TLR-5), bacterial DNA (TLR-9), double-stranded RNA and poly I:C (TLR-3), and yeast (TLR-2). In vivo activation of TLRs initiates an innate immune response involving specific cytokines, chemokines and growth factors. While all TLRs can activate certain intracellular signaling molecules such as nuclear factor kappa beta (NF-κB) and mitogen activated protein kinases (MAP kinases), the specific set of cytokines and chemokines released appears to be unique for each TLR. TLR7, 8, and 9 comprise a subfamily of TLRs which are located in endosomal or lysosomal compartments of immune cells such as dendritic cells and monocytes. In contrast to TLR7 and 9 which are highly expressed on plasmacytoid dendritic cells (pDC), TLR8 is mainly expressed on myeloid DC (mDC) and monocytes. This subfamily mediates recognition of microbial nucleic acids, such as single stranded RNA.

Small, low-molecular weight (less than 400 Daltons) synthetic imidazoquinoline compounds which resemble the purine nucleotides adenosine and guanosine were the first TLR7 and TLR8 agonists to be identified. A number of these compounds have demonstrated anti-viral and anti-cancer properties. For example, the TLR7 agonist imiquimod (ALDARA™) was approved by the U.S. Food and Drug Administration as a topical agent for the treatment of skin lesions caused by certain strains of the human papillomavirus. Imiquimod may also be useful for the treatment of primary skin cancers and cutaneous tumors such as basal cell carcinomas, keratoacanthomas, actinic keratoses, and Bowen's disease. The TLR7/8 agonist resiquimod (R-848) is being evaluated as a topical agent for the treatment of human genital herpes.

TLR agonists according to the disclosure can be any TLR agonist. For example, a TLR agonist can encompass a natural or synthetic TLR ligand, a mutein or derivative of a TLR ligand, a peptide mimetic of a TLR ligand, a small molecule that mimics the biological function of a TLR ligand, or an antibody that stimulates a TLR receptor. A TLR ligand is any molecule that binds to a TLR.

In some embodiments, an RLR agonist, or pharmaceutical composition thereof, provided by the disclosure, is combined with a TLR agonist, wherein the TLR agonist is selected from the group consisting of: a TLR1 agonist, a TLR2 agonist, a TLR3 agonist, a TLR4 agonist, a TLR5 agonist, a TLR6 agonist, a TLR7 agonist, a TLR8 agonist, a TLR9 agonist, a TLR10 agonist, and a TLR11 agonist.

In some embodiments, an RLR agonist provided by the disclosure is combined with a TLR3 agonist. A TLR3 agonist is an agonist that causes a signaling response through TLR3. Exemplary TLR3 agonists include, but are not limited to, polyinosinic:polycytidylic acid (poly I:C), HILTONOL® (poly ICLC), polyadenylic-polyuridylic acid (poly A:U), RIBOXXIM® (RGIC®100), RIBOXXON® (RGIC®50 bioconjugate), and RIBOXXOL® (RGIC®50).

In some embodiments, an RLR agonist provided by the disclosure is combined with polyinosinic:polycytidylic acid (poly I:C). In some embodiments, the RLR agonist is combined with HILTONOL® (poly ICLC). In some embodiments, the RLR agonist is combined with polyadenylic-polyuridylic acid (poly A:U). In some embodiments, the RLR agonist is combined with RIBOXXIM® (RGIC®100). In some embodiments, the RLR agonist is combined with RIBOXXON® (RGIC®50 bioconjugate). In some embodiments, the RLR agonist is combined with RIBOXXOL® (RGIC®50).

In some embodiments, an RLR agonist provided by the disclosure is combined with a TLR7 agonist. A TLR7 agonist is an agonist that causes a signaling response through TLR7. Non-limiting examples of TLR7 agonists include single stranded RNA (ssRNA), loxoribine (a guanosine analogue derivatized at positions N7 and C8), imidazoquinoline compounds (e.g., imiquimod and resiquimod), or derivatives thereof. Further exemplary TLR7 agonists include, but are not limited to, GS-9620 (Vesatolimod), imiquimod (ALDARA™), and resiquimod (R-848).

In some embodiments, an RLR agonist provided by the disclosure is combined with GS-9620 (Vesatolimod). In some embodiments, the RLR agonist is combined with imiquimod (ALDARA™). In some embodiments, the RLR agonist is combined with resiquimod (R-848).

In some embodiments, an RLR agonists provided by the disclosure is combined with a TLR9 agonist. A TLR9 agonist is an agonist that causes a signaling response through TLR9. Exemplary TLR9 agonists include, but are not limited to, CpG oligodeoxynucleotides (GpG ODNs). In some embodiments, the CpG ODN is a Class A CpG ODN (CpG-A ODN), a Class B CpG ODN (CpG-B ODN), or a Class C CpG ODN (CpG-B ODN).

In some embodiments, an RLR agonist provided by the disclosure is combined with a CpG oligodeoxynucleotide (CpG ODN). In some embodiments, the CpG ODN is a Class A CpG ODN (CpG-A ODN). In some embodiments, the CpG ODN is a Class B CpG ODN (CpG-B ODN). In some embodiments, the CpG ODN is a Class C CpG ODN (CpG-C ODN).

Other Combinations

In some embodiments, an RLR agonist, or pharmaceutical compositions thereof, provided by the disclosure is combined (e.g., administered in combination) with a VISTA antagonist, an adenosine A2AR antagonist, a B7-H3 antagonist, a B7-H4 antagonist, a BTLA antagonist, a CTLA-4 antagonist, an IDO antagonist, or a KIR antagonist In some embodiments, an RLR agonist, or pharmaceutical compositions thereof, provided by the disclosure is combined (e.g., administered in combination) with an agonist comprising an polypeptide (e.g, antibody, or antigen binding portion thereof) that specifically binds to CD137 (4-1BB).

In some embodiments, an RLR agonist, or pharmaceutical compositions thereof, provided by the disclosure is combined (e.g., administered in combination) with an agonist comprising an polypeptide (e.g., antibody, or antigen binding portion thereof) that specifically binds to CD134 (OX40).

An RLR agonist described herein can replace or augment a previously or currently administered therapy. For example, upon treating with an RLR agonist, administration of the one or more additional active agents can cease or diminish, e.g., be administered at lower levels or dosages. In some embodiments, administration of the previous therapy can be maintained. In some embodiments, a previous therapy will be maintained until the level of the RLR agonist reaches a level sufficient to provide a therapeutic effect. The two therapies can be administered in combination.

Monitoring a subject (e.g., a human patient) for an improvement in a cancer, as defined herein, means evaluating the subject for a change in a disease parameter, e.g., a reduction in tumor growth. In some embodiments, the evaluation is performed at least one (1) hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration. The subject can be evaluated in one or more of the following periods: prior to beginning of treatment; during the treatment; or after one or more elements of the treatment have been administered. Evaluation can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for a cancer described herein.

In some embodiments, an RLR agonist described herein is administered to modulate a T-cell response in a patient, for example, by increasing T-cell activation and/or proliferation. Enhancement of T cell proliferation, IFN production and secretion, and/or the cytolytic activity of T cells may be beneficial to patients in need thereof to treat a disease or condition. Accordingly, in some embodiments, an RLR agonist of the present disclosure is administered to a patent in need thereof to induce or increase T-cell activation, enhance T cell proliferation, induce the production and/or secretion of IFN, and/or induce a cytolytic T cell response.

In some embodiments, an RLR agonist described herein, can be employed in methods of detection and/or quantification of human RLRs in a biological sample. Accordingly, an RLR agonist, as described herein, is used to diagnose, prognose, and/or determine progression of disease (e.g., cancer) in a patient.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

EXAMPLES

The disclosure will be more fully understood by reference to the following examples. They should not, however, be construed as limiting the scope of the disclosure. It is understood that the examples and embodiments described herein are for illustrative purposes only and that various modifications or changes in light thereof will be suggested to persons skilled in the art and are to be included within the spirit and purview of this application and scope of the appended claims.

Example 1

Transfection of HuPBMCs with RLR Agonists Induces Cytokine Production In Vitro

To determine the effect of RLR agonists comprising various modification on cytokine induction, the ability of RLR agonists to induce cytokine production was assessed in vitro. Human peripheral blood mononuclear cells (huPBMCs) were prepared from two healthy donors and seeded at a density of $2 \times 10^5$ cells/well in a standard 96-well tissue culture plate in 100 µL of RPMI 1640 cell culture medium supplemented with fetal calf serum (FCS), L-glutamine, and Pen/Strep. Independent transfections of huPBMCs with RLR agonists, as indicated in FIG. 1, was carried out using Lipofectamine2000 as the transfection reagent (except for G10 and ODN2216, where direct incubation was applied, data not shown). Cells were incubated for 24 h at 37C in a humidified incubator followed by harvesting of cell culture supernatant. Supernatants were immediately frozen and stored at −20C. Samples were thawed once for analysis of cytokines IFN-α2a (FIG. 1), as well as IL-1β, IP-10, IL-6, IL-12p70, MCP-1 and MIP-1β (data not shown) using a U-Plex MSD platform according to the manufacturer's instructions. FIG. 1 shows the dose-dependent induction of IFN-α secretion from human PBMC treated with novel candidate RLR agonists comprising various modifications and/or sequence motifs. RLR agonists we added at either 10 nM, 2 nM, or 0.4 nM. The amount of IFN-α2a released by the cells in response to RLR agonist transfection is given in pg/mL.

Tables 3 and 4 show the sequences of each RLR agonist. Table 3 also shows the sequence and number corresponding to each compound tested in FIG. 1. For examples, compound X25224 in FIG. 1 corresponds to "RIG7" which comprises a first oligonucleotide comprising SEQ ID NO: 42 linked via a linker "UUCG" to a second oligonucleotide comprising SEQ ID NO: 73 and has a 5' diphosphate moiety. The sequence of RIG7 is also set forth as SEQ ID NO: 6 in Table 4.

TABLE 3

OLIGONUCLEOTIDE COMBINATION TABLE

| RNA | First Oligonucleotide (FO) | Second Oligonucleotide (SO) | Linker | 5' Phosphate Moiety |
|---|---|---|---|---|
| RIG 2a (X32671) | 37 | 68 | UUCG | — |
| RIG 2b (X25217) | 37 | 68 | UUCG | pp |
| RIG 3a (X32666) | 38 | 69 | UUCG | — |
| RIG 3b (X25218) | 38 | 69 | UUCG | pp |
| RIG 4 (X25219) | 39 | 70 | UUCG | pp |
| RIG 5 (X25221) | 40 | 71 | UUCG | pp |
| RIG 6 (X25222) | 41 | 72 | UUCG | pp |
| RIG 7 (X25224) | 42 | 73 | UUCG | pp |
| RIG 8 (X25225) | 43 | 74 | UUCG | pp |
| RIG 9 (X25226) | 44 | 75 | UUCG | pp |
| RIG 10 (X25227) | 45 | 76 | UUCG | pp |
| RIG 11 (X25228) | 46 | 77 | UUCG | pp |
| RIG 12 (X25229) | 47 | 78 | UUCG | pp |
| RIG 13a (X32667) | 48 | 79 | UUCG | — |
| RIG 13b (X25230) | 48 | 79 | UUCG | pp |
| RIG 13c (X24921) | 48 | 79 | UUCG | ppp |
| RIG 14 (X25231) | 49 | 80 | UUCG | pp |
| RIG 15a (X32665) | 50 | 81 | UUCG | — |
| RIG 15b (X25232) | 50 | 81 | UUCG | pp |
| RIG 15c (X24923) | 50 | 81 | UUCG | ppp |
| RIG 16 (X25233) | 51 | 82 | UUCG | pp |
| RIG 18 (X25234) | 52 | 83 | UUCG | pp |
| RIG 20a (X32750) | 53 | 84 | UUCG | — |
| RIG 20b (X25235) | 53 | 84 | UUCG | pp |
| RIG 21 (X25237) | 54 | 85 | UUCG | pp |
| RIG 22a (X32672) | 55 | 86 | UUCG | — |
| RIG 22b (X25239) | 55 | 86 | UUCG | pp |
| RIG 24a (X25241) | 56 | 87 | UUCG | pp |
| RIG 24b (X25240) | 56 | 87 | UUCG | ppp |
| RIG 25 (X25242) | 57 | 88 | UUCG | pp |

TABLE 3-continued

OLIGONUCLEOTIDE COMBINATION TABLE

| RNA | First Oligonucleotide (FO) | Second Oligonucleotide (SO) | Linker | 5' Phosphate Moiety |
|---|---|---|---|---|
| RIG 26 (X25243) | 58 | 89 | UUCG | pp |
| RIG 27a (X32669) | 59 | 89 | UUCG | — |
| RIG 27b (X25244) | 59 | 89 | UUCG | pp |
| RIG 27c (X24935) | 59 | 89 | UUCG | ppp |
| RIG 28a (X25245) | 60 | 90 | UUCG | pp |
| RIG 28b (X24936) | 60 | 90 | UUCG | ppp |
| RIG 35a (X32670) | 61 | 91 | UUCG | — |
| RIG 35b (X25247) | 61 | 91 | UUCG | pp |
| RIG 36 (X24945) | 62 | 92 | UUCG | pp |
| RIG 37a (X25249) | 63 | 91 | UUUGAU | pp |
| RIG 37b (X25248) | 63 | 91 | UUUGAU | ppp |
| RIG 38a (X32668) | 63 | 91 | UGUUU | — |
| RIG 38b (X25251) | 63 | 91 | UGUUU | pp |
| RIG 39 (X25253) | 63 | 91 | GAUC | pp |
| RIG 40 (X25255) | 64 | 93 | GAUC | pp |
| RIG 41 (X25257) | 65 | 94 | GAUC | pp |
| RIG 42 (X25259) | 64 | 93 | UUCG | pp |
| RIG 43a (X32673) | 63 | 91 | (C9) | — |
| RIG 43b (X25261) | 63 | 91 | (C9) | pp |
| RIG 44 (X25263) | 63 | 91 | (HEG) | pp |
| RIG 47 (X25265) | 66 | 95 | UUCG | pp |
| RIG 48 (X25267) | 67 | 96 | UUCG | pp |
| RIG 49a (X25269) | 63 | 97 | UUCG | pp |
| RIG 49b (X25268) | 63 | 97 | UUCG | ppp |
| RIG 50a (14L) (X32664) | 63 | 91 | UUCG | — |
| RIG 50b (14L) (X24943) | 63 | 91 | UUCG | pp |
| RIG 50c (14L) (X24907) | 63 | 91 | UUCG | ppp |

(—) indicates no 5' phosphate;
(pp) indicates 5' diphosphate;
(ppp) indicates 5' triphosphate

TABLE 4

SEQUENCE LISTING

| SEQ ID NO | Description | Sequence |
|---|---|---|
| 1 | RIG 2 Nucleic acid sequence | GGATCGATCGATCGUUCGCGATCGATCGATCC |
| 2 | RIG 3 Nucleic acid sequence | GGAUCGAUCGAUAUUUCGAUAUCGAUCGAUCC |
| 3 | RIG 4 Nucleic acid sequence | GCGCGCGCGCGCGCUUCGGCGCGCGCGCGCGC |
| 4 | RIG 5 Nucleic acid sequence | GGCGGCGCGCCGCCUUCGGGCGGCGCGCCGCC |
| 5 | RIG 6 Nucleic acid sequence | GGCGGCGGCGGCGGUUCGCCGCCGCCGCCGCC |
| 6 | RIG 7 Nucleic acid sequence | GGCGGCCGCCCGCGUUCGCGCGGGCGGCCGCC |
| 7 | RIG 8 Nucleic acid sequence | CGACGUCGACGUCGUUCGCGACGUCGACGUCG |
| 8 | RIG 9 Nucleic acid sequence | GCACGUCGACGUGCUUCGGCACGUCGACGUGC |
| 9 | RIG 10 Nucleic acid sequence | GGACGUCGACGUCCUUCGGGACGUCGACGUCC |
| 10 | RIG 11 Nucleic acid sequence | GGUCGCGACCAUAUUUCGAUAUGGUCGCGACC |
| 11 | RIG 12 Nucleic acid sequence | GGAUACGUCGACGUUUCGACGUCGACGUAUCC |
| 12 | RIG 13 Nucleic acid sequence | GAGAGAGAGAGAGAUUCGUCUCUCUCUCUCUC |
| 13 | RIG 14 Nucleic acid sequence | GAGUCUAGACUCCGUUCGCGGAGUCUAGACUC |
| 14 | RIG 15 Nucleic acid sequence (RIG 45) | CGAUCGAUCGAUCGUUCGCGAUCGAUCGAUCG |
| 15 | RIG 16 Nucleic acid sequence | CCAUCGAUCGAUCGUUCGCGAUCGAUCGAUGG |
| 16 | RIG 18 Nucleic acid sequence | GAAUCGAUCGAUCGUUCGCGAUCGAUCGAUUC |
| 17 | RIG 20 Nucleic acid sequence | GGGAUCGAUCGUUCGCGAUCGAUCCC |
| 18 | RIG 21 Nucleic acid sequence | CCCCCGAUCGAUCGUUCGCGAUCGAUCGGGGG |
| 19 | RIG 22 Nucleic acid sequence | GTGTGTGTGTGTGTUUCGACACACACACACAC |

TABLE 4-continued

SEQUENCE LISTING

| SEQ ID NO | Description | Sequence |
|---|---|---|
| 20 | RIG 24 Nucleic acid sequence | GTGTGTGGAUCGAUUUCGAUCGAUCCACACAC |
| 21 | RIG 25 Nucleic acid sequence | GGAICGAICGAICGUUCGCGAICGAICGAICC |
| 22 | RIG 26 Nucleic acid sequence | IIAUCIAUCIAUCIUUCGCIAUCIAUCIAUCC |
| 23 | RIG 27 Nucleic acid sequence | GGAUCIAUCIAUCIUUCGCIAUCIAUCIAUCC |
| 24 | RIG 28 Nucleic acid sequence | GGIUCGIUCGIUCGUUCGCGIUCGIUCGIUCC |
| 25 | RIG 35 Nucleic acid sequence | IGAUCGAUCGAUCGUUCGCGAUCGAUCGAUCC |
| 26 | RIG 36 Nucleic acid sequence | AUCGAUCGAUCGUUCGCGAUCGAUCGAU |
| 27 | RIG 37 Nucleic acid sequence | GGAUCGAUCGAUCGUUUGAUCGAUCGAUCGAUCC |
| 28 | RIG 38 Nucleic acid sequence | GGAUCGAUCGAUCGUGUUUCGAUCGAUCGAUCC |
| 29 | RIG 39 Nucleic acid sequence | GGAUCGAUCGAUCGGAUCCGAUCGAUCGAUCC |
| 30 | RIG 40 Nucleic acid sequence | GGCAUGCGACCUCUGUUUGAUCAAACAGAGGUCGCAUGCC |
| 31 | RIG 41 Nucleic acid sequence | GGCAUGCGACCUCUGAUCAGAGGUCGCAUGCC |
| 32 | RIG 42 Nucleic acid sequence | GGCAUGCGACCUCUGUUUUUCGAAACAGAGGUCGCAUGCC |
| 33 | RIG 47 Nucleic acid sequence | TGCUCGAUCGAUCGUUCGCGAUCGAUCGAGCA |
| 34 | RIG 48 Nucleic acid sequence | TCGUCGAUCGAUCGUUCGCGAUCGAUCGACGA |
| 35 | RIG 49 Nucleic acid sequence | GGAUCGAUCGAUCGUUCGTGAUCGAUCGAUGG |
| 36 | RIG 50 Nucleic acid sequence (14L) | GGAUCGAUCGAUCGUUCGCGAUCGAUCGAUCC |
| 37 | FO1 Nucleic acid sequence | GGATCGATCGATCG |
| 38 | FO2 Nucleic acid sequence | GGAUCGAUCGAUAU |
| 39 | FO3 Nucleic acid sequence | GCGCGCGCGCGCGC |
| 40 | FO4 Nucleic acid sequence | GGCGGCGCGCCGCC |
| 41 | FO5 Nucleic acid sequence | GGCGGCGGCGGCGG |
| 42 | FO6 Nucleic acid sequence | GGCGGCCGCCCGCG |
| 43 | FO7 Nucleic acid sequence | CGACGUCGACGUCG |
| 44 | FO8 Nucleic acid sequence | GCACGUCGACGUGC |
| 45 | FO9 Nucleic acid sequence | GGACGUCGACGUCC |
| 46 | FO10 Nucleic acid sequence | GGUCGCGACCAUAU |
| 47 | FO11 Nucleic acid sequence | GGAUACGUCGACGU |
| 48 | FO12 Nucleic acid sequence | GAGAGAGAGAGAGA |

TABLE 4-continued

SEQUENCE LISTING

| SEQ ID NO | Description | Sequence |
|---|---|---|
| 49 | F013 Nucleic acid sequence | GAGUCUAGACUCCG |
| 50 | F014 Nucleic acid sequence | CGAUCGAUCGAUCG |
| 51 | F015 Nucleic acid sequence | CCAUCGAUCGAUCG |
| 52 | F016 Nucleic acid sequence | GAAUCGAUCGAUCG |
| 53 | F017 Nucleic acid sequence | GGGAUCGAUCG |
| 54 | F018 Nucleic acid sequence | CCCCCGAUCGAUCG |
| 55 | F019 Nucleic acid sequence | GTGTGTGTGTGTGT |
| 56 | F020 Nucleic acid sequence | GTGTGTGGAUCGAU |
| 57 | F021 Nucleic acid sequence | GGAICGAICGAICG |
| 58 | F022 Nucleic acid sequence | IIAUCIAUCIAUCI |
| 59 | F023 Nucleic acid sequence | GGAUCIAUCIAUCI |
| 60 | F024 Nucleic acid sequence | GGIUCGIUCGIUCG |
| 61 | F025 Nucleic acid sequence | IGAUCGAUCGAUCG |
| 62 | F026 Nucleic acid sequence | AUCGAUCGAUCG |
| 63 | F027 Nucleic acid sequence | GGAUCGAUCGAUCG |
| 64 | F028 Nucleic acid sequence | GGCAUGCGACCUCUGUUU |
| 65 | F029 Nucleic acid sequence | GGCAUGCGACCUCU |
| 66 | F030 Nucleic acid sequence | TGCUCGAUCGAUCG |
| 67 | F031 Nucleic acid sequence | TCGUCGAUCGAUCG |
| 68 | S01 Nucleic acid sequence | CGATCGATCGATCC |
| 69 | S02 Nucleic acid sequence | AUAUCGAUCGAUCC |
| 70 | S03 Nucleic acid sequence | GCGCGCGCGCGCGC |
| 71 | S04 Nucleic acid sequence | GGCGGCGCGCCGCC |
| 72 | S05 Nucleic acid sequence | CCGCCGCCGCCGCC |
| 73 | S06 Nucleic acid sequence | CGCGGGCGGCCGCC |
| 74 | S07 Nucleic acid sequence | CGACGUCGACGUCG |
| 75 | S08 Nucleic acid sequence | GCACGUCGACGUGC |
| 76 | S09 Nucleic acid sequence | GGACGUCGACGUCC |
| 77 | S010 Nucleic acid sequence | AUAUGGUCGCGACC |

TABLE 4-continued

SEQUENCE LISTING

| SEQ ID NO | Description | Sequence |
|---|---|---|
| 78 | SO11 Nucleic acid sequence | ACGUCGACGUAUCC |
| 79 | SO12 Nucleic acid sequence | UCUCUCUCUCUCUC |
| 80 | SO13 Nucleic acid sequence | CGGAGUCUAGACUC |
| 81 | SO14 Nucleic acid sequence | CGAUCGAUCGAUCG |
| 82 | SO15 Nucleic acid sequence | CGAUCGAUCGAUGG |
| 83 | SO16 Nucleic acid sequence | CGAUCGAUCGAUUC |
| 84 | SO17 Nucleic acid sequence | CGAUCGAUCCC |
| 85 | SO18 Nucleic acid sequence | CGAUCGAUCGGGGG |
| 86 | SO19 Nucleic acid sequence | ACACACACACACAC |
| 87 | SO20 Nucleic acid sequence | AUCGAUCCACACAC |
| 88 | SO21 Nucleic acid sequence | CGAICGAICGAICC |
| 89 | SO22 Nucleic acid sequence | CIAUCIAUCIAUCC |
| 90 | SO23 Nucleic acid sequence | CGIUCGIUCGIUCC |
| 91 | SO24 Nucleic acid sequence | CGAUCGAUCGAUCC |
| 92 | SO25 Nucleic acid sequence | CGAUCGAUCGAU |
| 93 | SO26 Nucleic acid sequence | AAACAGAGGUCGCAUGCC |
| 94 | SO27 Nucleic acid sequence | AGAGGUCGCAUGCC |
| 95 | SO28 Nucleic acid sequence | CGAUCGAUCGAGCA |
| 96 | SO29 Nucleic acid sequence | CGAUCGAUCGACGA |
| 97 | SO30 Nucleic acid sequence | TGAUCGAUCGAUGG |
| 98 | Human RIG-I Amino acid sequence | MTTEQRRSLQAFQDYIRKTLDPTYILSYMAPW FREEEVQYIQAEKNNKGPMEAATLFLKFLLEL QEEGWFRGFLDALDHAGYSGLYEAIESWDFKK IEKLEEYRLLLKRLQPEFKTRIIPTDIISDLS ECLINQECEEILQICSTKGMMAGAEKLVECLL RSDKENWPKTLKLALEKERNKFSELWIVEKGI KDVETEDLEDKMETSDIQIFYQEDPECQNLSE NSCPPSEVSDTNLYSPFKPRNYQLELALPAMK GKNTIICAPTGCGKTFVSLLICEHHLKKFPQG QKGKVVFFANQIPVYEQQKSVFSKYFERHGYR VTGISGATAENVPVEQIVENNDIIILTPQILV NNLKKGTIPSLSIFTLMIFDECHNTSKQHPYN MIMFNYLDQKLGGSSGPLPQVIGLTASVGVGD AKNTDEALDYICKLCASLDASVIATVKHNLEE LEQVVYKPQKFFRKVESRISDKFKYIIAQLMR DTESLAKRICKDLENLSQIQNREFGTQKYEQW IVTVQKACMVFQMPDKDEESRICKALFLYTSH LRKYNDALIISEHARMKDALDYLKDFFSNVRA AGFDEIEQDLTQRFEEKLQELESVSRDPSNEN PKLEDLCFILQEEYHLNPETITILFVKTRALV DALKNWIEGNPKLSFLKPGILTGRGKTNQNTG MTLPAQKCILDAFKASGDHNILIATSVADEGI DIAQCNLVILYEYVGNVIKMIQTRGRGRARGS KCFLLTSNAGVIEKEQINMYKEKKMNDSILRL QTWDEAVFREKILHIQTHEKFIRDSQEKPKPV PDKENKKLLCRKCKALACYTADVRVIEECHYT VLGDAFKECFVSRPHPKPKQFSSFEKRAKIFC ARQNCSHDWGIHVKYKTFEIPVIKIESFVVED IATGVQTLYSKWKDFHFEKIPFDPAEMSK |
| 99 | Human MDA5 Amino acid sequence | MSNGYSTDENFRYLISCFRARVKMYIQVEPVL DYLTFLPAEVKEQIQRTVATSGNMQAVELLLS TLEKGVWHLGWTREFVEALRRTGSPLAARYMN PELTDLPSPSFENAHDEYLQLLNLLQPTLVDK LLVRDVLDKCMEEELLTIEDRNRIAAAENNGN ESGVRELLKRIVQKENWFSAFLNVLRQTGNNE LVQELTGSDCSESNAEIENLSQVDGPQVEEQL LSTTVQPNLEKEVWGMENNSSESSFADSSVVS ESDTSLAEGSVSCLDESLGHNSNMGSDSGTMG SDSDEENVAARASPEPELQLRPYQMEVAQPAL EGKNIICLPTGSGKTRVAVYIAKDHLDKKKK ASEPGKVIVLVNKVLLVEQLFRKEFQPFLKKW YRVIGLSGDTQLKISFPEVVKSCDIIISTAQI LENSLLNLENGEDAGVQLSDFSLIIIDECHHT |

TABLE 4-continued

SEQUENCE LISTING

| SEQ ID NO | Description | Sequence |
|---|---|---|
| | | NKEAVYNNIMRHYLMQKLKNNRLKKENKPVIP LPQILGLTASPGVGGATKQAKAEEHILKLCAN LDAFTIKTVKENLDQLKNQIQEPCKKFAIADA TREDPFKEKLLEIMTRIQTYCQMSPMSDFGTQ PYEQWAIQMEKKAAKEGNRKERVCAEHLRKYN EALQINDTIRMIDAYTHLETFYNEEKDKKFAV IEDDSDEGGDDEYCDGDEDEDDLKKPLKLDET DRFLMTLFFENNKMLKRLAENPEYENEKLTKL RNTIMEQYTRTEESARGIIFTKTRQSAYALSQ WITENEKFAEVGVKAHHLIGAGHSSEFKPMTQ NEQKEVISKFRTGKINLLIATTVAEEGLDIKE CNIVIRYGLVTNEIAMVQARGRARADESTYVL VAHSGSGVIEHETVNDFREKMMYKAIHCVQNM KPEEYAHKILELQMQSIMEKKMKTKRNIAKHY KNNPSLITFLCKNCSVLACSGEDIHVIEKMHH VNMTPEFKELYIVRENKALQKKCADYQINGEI ICKCGQAWGTMMVHKGLDLPCLKIRNFVVVFK NNSTKKQYKKWVELPITFPNLDYSECCLFSDE D |
| 100 | Human LGP2 Amino acid sequence | MELRSYQWEVIMPALEGKNIIIWLPTGAGKTR AAAYVAKRHLETVDGAKVVVLVNRVHLVTQHG EEFRRMLDGRWTVTTLSGDMGPRAGFGHLARC HDLLICTAELLQMALTSPEEEEHVELTVFSLI VVDECHHTHKDTVYNVIMSQYLELKLQRAQPL PQVLGLTASPGTGGASKLDGAINHVLQLCANL DTWCIMSPQNCCPQLQEHSQQPCKQYNLCHRR SQDPFGDLLKKLMDQIHDHLEMPELSRKFGTQ MYEQQVVKLSEAAALAGLQEQRVYALHLRRYN DALLIHDTVRAVDALAALQDFYHREHVTKTQI LCAERRLLALFDDRKNELAHLATHGPENPKLE MLEKILQRQFSSSNSPRGIIFTRTRQSAHSLL LWLQQQQGLQTVDIRAQLLIGAGNSSQSTHMT QRDQQEVIQKFQDGTLNLLVATSVAEEGLDIP HCNVVVRYGLLTNEISMVQARGRARADQSVYA FVATEGSRELKRELINEALETLMEQAVAAVQK MDQAEYQAKIRDLQQAALTKRAAQAAQRENQR QQFPVEHVQLLCINCMVAVGHGSDLRKVEGTH HVNVNPNFSNYYNVSRDPVVINKVFKDWKPGG VISCRNCGEVWGLQMIYKSVKLPVLKVRSMLL ETPQGRIQAKKWSRVPFSVPDFDFLQHCAENL SDLSLD |

The invention claimed is:

1. A synthetic RIG-I-like receptor (RLR) agonist that specifically binds to a RIG-I-like receptor (RLR), wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof; wherein the agonist comprises a [AUCG]n repeat motif, wherein n=3, and wherein the 5' most AUCG repeat motif is preceded by CG.

2. The agonist of claim 1, wherein the linker is a nucleotide linker or non-nucleotide linker.

3. The agonist of claim 2, wherein the nucleotide linker comprises a tetraloop comprising the sequence UUCG.

4. The agonist of claim 2, wherein the non-nucleotide linker is selected from a hexaethylene glycol linker or a C9 alkyl linker.

5. The agonist of claim 1, wherein the first polynucleotide comprises SEQ ID NO: 50 and the second polynucleotide comprises SEQ ID NO: 81.

6. The agonist of claim 5, wherein the linker is a nucleotide linker or a non-nucleotide linker.

7. The agonist of claim 6, wherein the nucleotide linker comprises a tetraloop comprising the sequence UUCG.

8. The agonist of claim 6, wherein the non-nucleotide linker is selected from a hexaethylene glycol linker or a C9 alkyl linker.

9. A pharmaceutical composition comprising the agonist of claim 1, and a pharmaceutically acceptable carrier.

10. A pharmaceutical composition comprising the agonist of claim 5, and a pharmaceutically acceptable carrier.

11. A pharmaceutical composition comprising the agonist of claim 7, and a pharmaceutically acceptable carrier.

12. A synthetic RIG-I-like receptor (RLR) agonist that specifically binds to a RIG-I-like receptor (RLR), wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof; wherein the agonist comprises a [AUCG]n repeat motif, wherein n=3, and wherein the 5' most AUCG repeat motif is preceded by IG.

13. The agonist of claim 12, wherein the linker is a nucleotide linker or a non-nucleotide linker.

14. The agonist of claim 13, wherein the nucleotide linker comprises a tetraloop comprising the sequence UUCG.

15. The agonist of claim 13, wherein the non-nucleotide linker is selected from a hexaethylene glycol linker or a C9 alkyl linker.

16. The agonist of claim 12, wherein the first polynucleotide comprises SEQ ID NO: 61 and the second polynucleotide comprises SEQ ID NO: 91.

17. The agonist of claim 16, wherein the linker is a nucleotide linker or a non-nucleotide linker.

18. The agonist of claim 17, wherein the nucleotide linker comprises a tetraloop comprising the sequence UUCG.

19. The agonist of claim 17, wherein the non-nucleotide linker is selected from a hexaethylene glycol linker or a C9 alkyl linker.

20. A pharmaceutical composition comprising the agonist of claim 12, and a pharmaceutically acceptable carrier.

21. A pharmaceutical composition comprising the agonist of claim 16, and a pharmaceutically acceptable carrier.

22. A pharmaceutical composition comprising the agonist of claim 18, and a pharmaceutically acceptable carrier.

23. A synthetic RIG-I-like receptor (RLR) agonist that specifically binds to a RIG-I-like receptor (RLR), wherein the agonist comprises a blunt-ended, hairpin RNA comprising a first polynucleotide connected to a second polynucleotide by a linker, wherein the first polynucleotide is sufficiently complementary to the second polynucleotide to form a duplex, wherein the duplex comprises less than 19 base pairs, wherein the 5' most nucleotide of the first oligonucleotide comprises a 5' diphosphate or triphosphate moiety, or derivative or analog thereof; wherein the agonist comprises a [AUCG]n repeat motif, wherein n=3, wherein the 5' most AUCG repeat is preceded by GG, and wherein each G in the AUCG motif is substituted by inosine.

24. The agonist of claim 23, wherein the linker is a nucleotide linker or a non-nucleotide linker.

25. The agonist of claim 24, wherein the nucleotide linker comprises a tetraloop comprising the sequence UUCG.

26. The agonist of claim 24, wherein the non-nucleotide linker is selected from a hexaethylene glycol linker or a C9 alkyl linker.

27. The agonist of claim 23, wherein the first polynucleotide comprises SEQ ID NO: 59 and the second polynucleotide comprises SEQ ID NO: 89.

28. The agonist of claim 27, wherein the linker is a nucleotide linker or a non-nucleotide linker.

29. The agonist of claim 28, wherein the nucleotide linker comprises a tetraloop comprising the sequence UUCG.

30. The agonist of claim 28, wherein the non-nucleotide linker is selected from a hexaethylene glycol linker or a C9 alkyl linker.

31. A pharmaceutical composition comprising the agonist of claim 23, and a pharmaceutically acceptable carrier.

32. A pharmaceutical composition comprising the agonist of claim 27, and a pharmaceutically acceptable carrier.

33. A pharmaceutical composition comprising the agonist of claim 29, and a pharmaceutically acceptable carrier.

* * * * *

SEQUENCE LISTING

<160> NUMBER OF SEQ ID NOS: 100

<210> SEQ ID NO 1
<211> LENGTH: 32
<212> TYPE: DNA
<213> ORGANISM: Artificial Sequence
<220> FEATURE:
<223> OTHER INFORMATION: Synthetic: RIG 2 Nucleic acid sequence

<400> SEQUENCE: 1
ggatcgatcg atcguucgcg atcgatcgat cc                                32

<210> SEQ ID NO 2
<211> LENGTH: 32
<212> TYPE: RNA
<213> ORGANISM: Artificial Sequence
<220> FEATURE:
<223> OTHER INFORMATION: Synthetic: RIG 3 Nucleic acid sequence

<400> SEQUENCE: 2
ggaucgaucg auauuucgau aucgaucgau cc                                32

<210> SEQ ID NO 3
<211> LENGTH: 32
<212> TYPE: RNA
<213> ORGANISM: Artificial Sequence
<220> FEATURE:
<223> OTHER INFORMATION: Synthetic: RIG 4 Nucleic acid sequence

<400> SEQUENCE: 3
gcgcgcgcgc gcgcuucggc gcgcgcgcgc gc                                32

<210> SEQ ID NO 4
<211> LENGTH: 32
<212> TYPE: RNA
<213> ORGANISM: Artificial Sequence
<220> FEATURE:
<223> OTHER INFORMATION: Synthetic: RIG 5 Nucleic acid sequence

<400> SEQUENCE: 4
ggcggcgcgc cgccuucggg cggcgcgccg cc                                    32

<210> SEQ ID NO 5
<211> LENGTH: 32
<212> TYPE: RNA
<213> ORGANISM: Artificial Sequence
<220> FEATURE:
<223> OTHER INFORMATION: Synthetic: RIG 6 Nucleic acid sequence

<400> SEQUENCE: 5
ggcggcggcg gcgguucgcc gccgccgccg cc                                    32

<210> SEQ ID NO 6
<211> LENGTH: 32
<212> TYPE: RNA
<213> ORGANISM: Artificial Sequence
<220> FEATURE:
<223> OTHER INFORMATION: Synthetic: RIG 7 Nucleic acid sequence

<400> SEQUENCE: 6
ggcggccgcc cgcguucgcg cgggcggccg cc                                    32

<210> SEQ ID NO 7
<211> LENGTH: 32
<212> TYPE: RNA
<213> ORGANISM: Artificial Sequence
<220> FEATURE:
<223> OTHER INFORMATION: Synthetic: RIG 8 Nucleic acid sequence

<400> SEQUENCE: 7
cgacgucgac gucguucgcg acgucgacgu cg                                    32

<210> SEQ ID NO 8
<211> LENGTH: 32
<212> TYPE: RNA
<213> ORGANISM: Artificial Sequence
<220> FEATURE:
<223> OTHER INFORMATION: Synthetic: RIG 9 Nucleic acid sequence

<400> SEQUENCE: 8
gcacgucgac gugcuucggc acgucgacgu gc                                    32

<210> SEQ ID NO 9
<211> LENGTH: 32
<212> TYPE: RNA
<213> ORGANISM: Artificial Sequence
<220> FEATURE:
<223> OTHER INFORMATION: Synthetic: RIG 10 Nucleic acid sequence

<400> SEQUENCE: 9
ggacgucgac guccuucggg acgucgacgu cc                                    32

<210> SEQ ID NO 10
<211> LENGTH: 32
<212> TYPE: RNA
<213> ORGANISM: Artificial Sequence
<220> FEATURE:
<223> OTHER INFORMATION: Synthetic: RIG 11 Nucleic acid sequence

<400> SEQUENCE: 10
ggucgcgacc auauuucgau auggucgcga cc                                    32

<210> SEQ ID NO 11

```
<211> LENGTH: 32
<212> TYPE: RNA
<213> ORGANISM: Artificial Sequence
<220> FEATURE:
<223> OTHER INFORMATION: Synthetic: RIG 12 Nucleic acid sequence

<400> SEQUENCE: 11
ggauacgucg acguuucgac gucgacguau cc                                      32

<210> SEQ ID NO 12
<211> LENGTH: 32
<212> TYPE: RNA
<213> ORGANISM: Artificial Sequence
<220> FEATURE:
<223> OTHER INFORMATION: Synthetic: RIG 13 Nucleic acid sequence

<400> SEQUENCE: 12
gagagagaga gagauucguc ucucucucuc uc                                      32

<210> SEQ ID NO 13
<211> LENGTH: 32
<212> TYPE: RNA
<213> ORGANISM: Artificial Sequence
<220> FEATURE:
<223> OTHER INFORMATION: Synthetic: RIG 14 Nucleic acid sequence

<400> SEQUENCE: 13
gagucuagac uccguucgcg gagucuagac uc                                      32

<210> SEQ ID NO 14
<211> LENGTH: 32
<212> TYPE: RNA
<213> ORGANISM: Artificial Sequence
<220> FEATURE:
<223> OTHER INFORMATION: Synthetic: RIG 15 Nucleic acid sequence
      (RIG 45)

<400> SEQUENCE: 14
cgaucgaucg aucguucgcg aucgaucgau cg                                      32

<210> SEQ ID NO 15
<211> LENGTH: 32
<212> TYPE: RNA
<213> ORGANISM: Artificial Sequence
<220> FEATURE:
<223> OTHER INFORMATION: Synthetic: RIG 16 Nucleic acid sequence

<400> SEQUENCE: 15
ccaucgaucg aucguucgcg aucgaucgau gg                                      32

<210> SEQ ID NO 16
<211> LENGTH: 32
<212> TYPE: RNA
<213> ORGANISM: Artificial Sequence
<220> FEATURE:
<223> OTHER INFORMATION: Synthetic: RIG 18 Nucleic acid sequence

<400> SEQUENCE: 16
gaaucgaucg aucguucgcg aucgaucgau uc                                      32

<210> SEQ ID NO 17
<211> LENGTH: 26
<212> TYPE: RNA
<213> ORGANISM: Artificial Sequence
<220> FEATURE:
<223> OTHER INFORMATION: Synthetic: RIG 20 Nucleic acid sequence
```

```
<400> SEQUENCE: 17
gggaucgauc guucgcgauc gauccc                                        26

<210> SEQ ID NO 18
<211> LENGTH: 32
<212> TYPE: RNA
<213> ORGANISM: Artificial Sequence
<220> FEATURE:
<223> OTHER INFORMATION: Synthetic: RIG 21 Nucleic acid sequence

<400> SEQUENCE: 18
cccccgaucg aucguucgcg aucgaucggg gg                                 32

<210> SEQ ID NO 19
<211> LENGTH: 32
<212> TYPE: DNA
<213> ORGANISM: Artificial Sequence
<220> FEATURE:
<223> OTHER INFORMATION: Synthetic: RIG 22 Nucleic acid sequence

<400> SEQUENCE: 19
gtgtgtgtgt gtgtuucgac acacacacac ac                                 32

<210> SEQ ID NO 20
<211> LENGTH: 32
<212> TYPE: DNA
<213> ORGANISM: Artificial Sequence
<220> FEATURE:
<223> OTHER INFORMATION: Synthetic: RIG 24 Nucleic acid sequence

<400> SEQUENCE: 20
gtgtgtggau cgauuucgau cgauccacac ac                                 32

<210> SEQ ID NO 21
<211> LENGTH: 32
<212> TYPE: RNA
<213> ORGANISM: Artificial Sequence
<220> FEATURE:
<223> OTHER INFORMATION: Synthetic: RIG 25 Nucleic acid sequence
<220> FEATURE:
<221> NAME/KEY: misc_feature
<222> LOCATION: (4)..(4)
<223> OTHER INFORMATION: n is inosine
<220> FEATURE:
<221> NAME/KEY: misc_feature
<222> LOCATION: (8)..(8)
<223> OTHER INFORMATION: n is inosine
<220> FEATURE:
<221> NAME/KEY: misc_feature
<222> LOCATION: (12)..(12)
<223> OTHER INFORMATION: n is inosine
<220> FEATURE:
<221> NAME/KEY: misc_feature
<222> LOCATION: (22)..(22)
<223> OTHER INFORMATION: n is inosine
<220> FEATURE:
<221> NAME/KEY: misc_feature
<222> LOCATION: (26)..(26)
<223> OTHER INFORMATION: n is inosine
<220> FEATURE:
<221> NAME/KEY: misc_feature
<222> LOCATION: (30)..(30)
<223> OTHER INFORMATION: n is inosine

<400> SEQUENCE: 21
ggancgancg ancguucgcg ancgancgan cc                                 32

<210> SEQ ID NO 22
<211> LENGTH: 32
```

```
<212> TYPE: RNA
<213> ORGANISM: Artificial Sequence
<220> FEATURE:
<223> OTHER INFORMATION: Synthetic: RIG 26 Nucleic acid sequence
<220> FEATURE:
<221> NAME/KEY: misc_feature
<222> LOCATION: (1)..(2)
<223> OTHER INFORMATION: n is inosine
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (10)..(10)
<223> OTHER INFORMATION: n is inosine
<220> FEATURE:
<221> NAME/KEY: misc_feature
<222> LOCATION: (14)..(14)
<223> OTHER INFORMATION: n is inosine
<220> FEATURE:
<221> NAME/KEY: misc_feature
<222> LOCATION: (20)..(20)
<223> OTHER INFORMATION: n is inosine
<220> FEATURE:
<221> NAME/KEY: misc_feature
<222> LOCATION: (24)..(24)
<223> OTHER INFORMATION: n is inosine
<220> FEATURE:
<221> NAME/KEY: misc_feature
<222> LOCATION: (28)..(28)
<223> OTHER INFORMATION: n is inosine

<400> SEQUENCE: 22
nnaucnaucn aucnuucgcn aucnaucnau cc                                32

<210> SEQ ID NO 23
<211> LENGTH: 32
<212> TYPE: RNA
<213> ORGANISM: Artificial Sequence
<220> FEATURE:
<223> OTHER INFORMATION: Synthetic: RIG 27 Nucleic acid sequence
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (10)..(10)
<223> OTHER INFORMATION: n is inosine
<220> FEATURE:
<221> NAME/KEY: misc_feature
<222> LOCATION: (14)..(14)
<223> OTHER INFORMATION: n is inosine
<220> FEATURE:
<221> NAME/KEY: misc_feature
<222> LOCATION: (20)..(20)
<223> OTHER INFORMATION: n is inosine
<220> FEATURE:
<221> NAME/KEY: misc_feature
<222> LOCATION: (24)..(24)
<223> OTHER INFORMATION: n is inosine
<220> FEATURE:
<221> NAME/KEY: misc_feature
<222> LOCATION: (28)..(28)
<223> OTHER INFORMATION: n is inosine

<400> SEQUENCE: 23
ggaucnaucn aucnuucgcn aucnaucnau cc                                32

<210> SEQ ID NO 24
<211> LENGTH: 32
<212> TYPE: RNA
<213> ORGANISM: Artificial Sequence
<220> FEATURE:
```

```
<223> OTHER INFORMATION: Synthetic: RIG 28 Nucleic acid sequence
<220> FEATURE:
<221> NAME/KEY: misc_feature
<222> LOCATION: (3)..(3)
<223> OTHER INFORMATION: n is inosine
<220> FEATURE:
<221> NAME/KEY: misc_feature
<222> LOCATION: (7)..(7)
<223> OTHER INFORMATION: n is inosine
<220> FEATURE:
<221> NAME/KEY: misc_feature
<222> LOCATION: (11)..(11)
<223> OTHER INFORMATION: n is inosine
<220> FEATURE:
<221> NAME/KEY: misc_feature
<222> LOCATION: (21)..(21)
<223> OTHER INFORMATION: n is inosine
<220> FEATURE:
<221> NAME/KEY: misc_feature
<222> LOCATION: (25)..(25)
<223> OTHER INFORMATION: n is inosine
<220> FEATURE:
<221> NAME/KEY: misc_feature
<222> LOCATION: (29)..(29)
<223> OTHER INFORMATION: n is inosine

<400> SEQUENCE: 24
ggnucgnucg nucguucgcg nucgnucgnu cc                                32

<210> SEQ ID NO 25
<211> LENGTH: 32
<212> TYPE: RNA
<213> ORGANISM: Artificial Sequence
<220> FEATURE:
<223> OTHER INFORMATION: Synthetic: RIG 35 Nucleic acid sequence
<220> FEATURE:
<221> NAME/KEY: misc_feature
<222> LOCATION: (1)..(1)
<223> OTHER INFORMATION: n is inosine

<400> SEQUENCE: 25
ngaucgaucg aucguucgcg aucgaucgau cc                                32

<210> SEQ ID NO 26
<211> LENGTH: 28
<212> TYPE: RNA
<213> ORGANISM: Artificial Sequence
<220> FEATURE:
<223> OTHER INFORMATION: Synthetic: RIG 36 Nucleic acid sequence

<400> SEQUENCE: 26
aucgaucgau cguucgcgau cgaucgau                                     28

<210> SEQ ID NO 27
<211> LENGTH: 34
<212> TYPE: RNA
<213> ORGANISM: Artificial Sequence
<220> FEATURE:
<223> OTHER INFORMATION: Synthetic: RIG 37 Nucleic acid sequence

<400> SEQUENCE: 27
ggaucgaucg aucguuugau cgaucgaucg aucc                              34

<210> SEQ ID NO 28
<211> LENGTH: 33
<212> TYPE: RNA
<213> ORGANISM: Artificial Sequence
<220> FEATURE:
<223> OTHER INFORMATION: Synthetic: RIG 38 Nucleic acid sequence

<400> SEQUENCE: 28
```

```
ggaucgaucg aucguguuuc gaucgaucga ucc                              33
```

<210> SEQ ID NO 29
<211> LENGTH: 32
<212> TYPE: RNA
<213> ORGANISM: Artificial Sequence
<220> FEATURE:
<223> OTHER INFORMATION: Synthetic: RIG 39 Nucleic acid sequence

<400> SEQUENCE: 29

```
ggaucgaucg aucggauccg aucgaucgau cc                              32
```

<210> SEQ ID NO 30
<211> LENGTH: 40
<212> TYPE: RNA
<213> ORGANISM: Artificial Sequence
<220> FEATURE:
<223> OTHER INFORMATION: Synthetic: RIG 40 Nucleic acid sequence

<400> SEQUENCE: 30

```
ggcaugcgac cucuguuuga ucaaacagag gucgcaugcc                      40
```

<210> SEQ ID NO 31
<211> LENGTH: 32
<212> TYPE: RNA
<213> ORGANISM: Artificial Sequence
<220> FEATURE:
<223> OTHER INFORMATION: Synthetic: RIG 41 Nucleic acid sequence

<400> SEQUENCE: 31

```
ggcaugcgac cucugaucag aggucgcaug cc                              32
```

<210> SEQ ID NO 32
<211> LENGTH: 40
<212> TYPE: RNA
<213> ORGANISM: Artificial Sequence
<220> FEATURE:
<223> OTHER INFORMATION: Synthetic: RIG 42 Nucleic acid sequence

<400> SEQUENCE: 32

```
ggcaugcgac cucuguuuuu cgaaacagag gucgcaugcc                      40
```

<210> SEQ ID NO 33
<211> LENGTH: 32
<212> TYPE: DNA
<213> ORGANISM: Artificial Sequence
<220> FEATURE:
<223> OTHER INFORMATION: Synthetic: RIG 47 Nucleic acid sequence

<400> SEQUENCE: 33

```
tgcucgaucg aucguucgcg aucgaucgag ca                              32
```

<210> SEQ ID NO 34
<211> LENGTH: 32
<212> TYPE: DNA
<213> ORGANISM: Artificial Sequence
<220> FEATURE:
<223> OTHER INFORMATION: Synthetic: RIG 48 Nucleic acid sequence

<400> SEQUENCE: 34

```
tcgucgaucg aucguucgcg aucgaucgac ga                              32
```

<210> SEQ ID NO 35
<211> LENGTH: 32
<212> TYPE: DNA

```
<213> ORGANISM: Artificial Sequence
<220> FEATURE:
<223> OTHER INFORMATION: Synthetic: RIG 49 Nucleic acid sequence

<400> SEQUENCE: 35
ggaucgaucg aucguucgtg aucgaucgau gg                                    32

<210> SEQ ID NO 36
<211> LENGTH: 32
<212> TYPE: RNA
<213> ORGANISM: Artificial Sequence
<220> FEATURE:
<223> OTHER INFORMATION: Synthetic: RIG 50 Nucleic acid sequence (14L)

<400> SEQUENCE: 36
ggaucgaucg aucguucgcg aucgaucgau cc                                    32

<210> SEQ ID NO 37
<211> LENGTH: 14
<212> TYPE: DNA
<213> ORGANISM: Artificial Sequence
<220> FEATURE:
<223> OTHER INFORMATION: Synthetic: FO1 Nucleic acid sequence

<400> SEQUENCE: 37
ggatcgatcg atcg                                                        14

<210> SEQ ID NO 38
<211> LENGTH: 14
<212> TYPE: RNA
<213> ORGANISM: Artificial Sequence
<220> FEATURE:
<223> OTHER INFORMATION: Synthetic: FO2 Nucleic acid sequence

<400> SEQUENCE: 38
ggaucgaucg auau                                                        14

<210> SEQ ID NO 39
<211> LENGTH: 14
<212> TYPE: RNA
<213> ORGANISM: Artificial Sequence
<220> FEATURE:
<223> OTHER INFORMATION: Synthetic: FO3 Nucleic acid sequence

<400> SEQUENCE: 39
gcgcgcgcgc gcgc                                                        14

<210> SEQ ID NO 40
<211> LENGTH: 14
<212> TYPE: RNA
<213> ORGANISM: Artificial Sequence
<220> FEATURE:
<223> OTHER INFORMATION: Synthetic: FO4 Nucleic acid sequence

<400> SEQUENCE: 40
ggcggcgcgc cgcc                                                        14

<210> SEQ ID NO 41
<211> LENGTH: 14
<212> TYPE: RNA
<213> ORGANISM: Artificial Sequence
<220> FEATURE:
<223> OTHER INFORMATION: Synthetic: FO5 Nucleic acid sequence

<400> SEQUENCE: 41
ggcggcggcg gcgg                                                        14
```

<210> SEQ ID NO 42
<211> LENGTH: 14
<212> TYPE: RNA
<213> ORGANISM: Artificial Sequence
<220> FEATURE:
<223> OTHER INFORMATION: Synthetic: F06 Nucleic acid sequence

<400> SEQUENCE: 42
ggcggccgcc cgcg                                                         14

<210> SEQ ID NO 43
<211> LENGTH: 14
<212> TYPE: RNA
<213> ORGANISM: Artificial Sequence
<220> FEATURE:
<223> OTHER INFORMATION: Synthetic: F07 Nucleic acid sequence

<400> SEQUENCE: 43
cgacgucgac gucg                                                         14

<210> SEQ ID NO 44
<211> LENGTH: 14
<212> TYPE: RNA
<213> ORGANISM: Artificial Sequence
<220> FEATURE:
<223> OTHER INFORMATION: Synthetic: F08 Nucleic acid sequence

<400> SEQUENCE: 44
gcacgucgac gugc                                                         14

<210> SEQ ID NO 45
<211> LENGTH: 14
<212> TYPE: RNA
<213> ORGANISM: Artificial Sequence
<220> FEATURE:
<223> OTHER INFORMATION: Synthetic: F09 Nucleic acid sequence

<400> SEQUENCE: 45
ggacgucgac gucc                                                         14

<210> SEQ ID NO 46
<211> LENGTH: 14
<212> TYPE: RNA
<213> ORGANISM: Artificial Sequence
<220> FEATURE:
<223> OTHER INFORMATION: Synthetic: F010 Nucleic acid sequence

<400> SEQUENCE: 46
ggucgcgacc auau                                                         14

<210> SEQ ID NO 47
<211> LENGTH: 14
<212> TYPE: RNA
<213> ORGANISM: Artificial Sequence
<220> FEATURE:
<223> OTHER INFORMATION: Synthetic: F011 Nucleic acid sequence

<400> SEQUENCE: 47
ggauacgucg acgu                                                         14

<210> SEQ ID NO 48
<211> LENGTH: 14
<212> TYPE: RNA
<213> ORGANISM: Artificial Sequence
<220> FEATURE:

```
<223> OTHER INFORMATION: Synthetic: FO12 Nucleic acid sequence

<400> SEQUENCE: 48
gagagagaga gaga                                                  14

<210> SEQ ID NO 49
<211> LENGTH: 14
<212> TYPE: RNA
<213> ORGANISM: Artificial Sequence
<220> FEATURE:
<223> OTHER INFORMATION: Synthetic: FO13 Nucleic acid sequence

<400> SEQUENCE: 49
gagucuagac uccg                                                  14

<210> SEQ ID NO 50
<211> LENGTH: 14
<212> TYPE: RNA
<213> ORGANISM: Artificial Sequence
<220> FEATURE:
<223> OTHER INFORMATION: Synthetic: FO14 Nucleic acid sequence

<400> SEQUENCE: 50
cgaucgaucg aucg                                                  14

<210> SEQ ID NO 51
<211> LENGTH: 14
<212> TYPE: RNA
<213> ORGANISM: Artificial Sequence
<220> FEATURE:
<223> OTHER INFORMATION: Synthetic: FO15 Nucleic acid sequence

<400> SEQUENCE: 51
ccaucgaucg aucg                                                  14

<210> SEQ ID NO 52
<211> LENGTH: 14
<212> TYPE: RNA
<213> ORGANISM: Artificial Sequence
<220> FEATURE:
<223> OTHER INFORMATION: Synthetic: FO16 Nucleic acid sequence

<400> SEQUENCE: 52
gaaucgaucg aucg                                                  14

<210> SEQ ID NO 53
<211> LENGTH: 11
<212> TYPE: RNA
<213> ORGANISM: Artificial Sequence
<220> FEATURE:
<223> OTHER INFORMATION: Synthetic: FO17 Nucleic acid sequence

<400> SEQUENCE: 53
gggaucgauc g                                                     11

<210> SEQ ID NO 54
<211> LENGTH: 14
<212> TYPE: RNA
<213> ORGANISM: Artificial Sequence
<220> FEATURE:
<223> OTHER INFORMATION: Synthetic: FO18 Nucleic acid sequence

<400> SEQUENCE: 54
cccccgaucg aucg                                                  14
```

```
<210> SEQ ID NO 55
<211> LENGTH: 14
<212> TYPE: DNA
<213> ORGANISM: Artificial Sequence
<220> FEATURE:
<223> OTHER INFORMATION: Synthetic: FO19 Nucleic acid sequence

<400> SEQUENCE: 55
gtgtgtgtgt gtgt                                                        14

<210> SEQ ID NO 56
<211> LENGTH: 14
<212> TYPE: DNA
<213> ORGANISM: Artificial Sequence
<220> FEATURE:
<223> OTHER INFORMATION: Synthetic: FO20 Nucleic acid sequence

<400> SEQUENCE: 56
gtgtgtggau cgau                                                        14

<210> SEQ ID NO 57
<211> LENGTH: 14
<212> TYPE: RNA
<213> ORGANISM: Artificial Sequence
<220> FEATURE:
<223> OTHER INFORMATION: Synthetic: FO21 Nucleic acid sequence
<220> FEATURE:
<221> NAME/KEY: misc_feature
<222> LOCATION: (4)..(4)
<223> OTHER INFORMATION: n is inosine
<220> FEATURE:
<221> NAME/KEY: misc_feature
<222> LOCATION: (8)..(8)
<223> OTHER INFORMATION: n is inosine
<220> FEATURE:
<221> NAME/KEY: misc_feature
<222> LOCATION: (12)..(12)
<223> OTHER INFORMATION: n is inosine

<400> SEQUENCE: 57
ggancgancg ancg                                                        14

<210> SEQ ID NO 58
<211> LENGTH: 14
<212> TYPE: RNA
<213> ORGANISM: Artificial Sequence
<220> FEATURE:
<223> OTHER INFORMATION: Synthetic: FO22 Nucleic acid sequence
<220> FEATURE:
<221> NAME/KEY: misc_feature
<222> LOCATION: (1)..(2)
<223> OTHER INFORMATION: n is inosine
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (10)..(10)
<223> OTHER INFORMATION: n is inosine
<220> FEATURE:
<221> NAME/KEY: misc_feature
<222> LOCATION: (14)..(14)
<223> OTHER INFORMATION: n is inosine

<400> SEQUENCE: 58
nnaucnaucn aucn                                                        14

<210> SEQ ID NO 59
<211> LENGTH: 14
<212> TYPE: RNA
```

```
<213> ORGANISM: Artificial Sequence
<220> FEATURE:
<223> OTHER INFORMATION: Synthetic: FO23 Nucleic acid sequence
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (10)..(10)
<223> OTHER INFORMATION: n is inosine
<220> FEATURE:
<221> NAME/KEY: misc_feature
<222> LOCATION: (14)..(14)
<223> OTHER INFORMATION: n is inosine

<400> SEQUENCE: 59
ggaucnaucn aucn                                                       14

<210> SEQ ID NO 60
<211> LENGTH: 14
<212> TYPE: RNA
<213> ORGANISM: Artificial Sequence
<220> FEATURE:
<223> OTHER INFORMATION: Synthetic: FO24 Nucleic acid sequence
<220> FEATURE:
<221> NAME/KEY: misc_feature
<222> LOCATION: (3)..(3)
<223> OTHER INFORMATION: n is inosine
<220> FEATURE:
<221> NAME/KEY: misc_feature
<222> LOCATION: (7)..(7)
<223> OTHER INFORMATION: n is inosine
<220> FEATURE:
<221> NAME/KEY: misc_feature
<222> LOCATION: (11)..(11)
<223> OTHER INFORMATION: n is inosine

<400> SEQUENCE: 60
ggnucgnucg nucg                                                       14

<210> SEQ ID NO 61
<211> LENGTH: 14
<212> TYPE: RNA
<213> ORGANISM: Artificial Sequence
<220> FEATURE:
<223> OTHER INFORMATION: Synthetic: FO25 Nucleic acid sequence
<220> FEATURE:
<221> NAME/KEY: misc_feature
<222> LOCATION: (1)..(1)
<223> OTHER INFORMATION: n is inosine

<400> SEQUENCE: 61
ngaucgaucg aucg                                                       14

<210> SEQ ID NO 62
<211> LENGTH: 12
<212> TYPE: RNA
<213> ORGANISM: Artificial Sequence
<220> FEATURE:
<223> OTHER INFORMATION: Synthetic: FO26 Nucleic acid sequence

<400> SEQUENCE: 62
aucgaucgau cg                                                         12

<210> SEQ ID NO 63
<211> LENGTH: 14
<212> TYPE: RNA
<213> ORGANISM: Artificial Sequence
<220> FEATURE:
<223> OTHER INFORMATION: Synthetic: FO27 Nucleic acid sequence
```

```
<400> SEQUENCE: 63
ggaucgaucg aucg                                                        14

<210> SEQ ID NO 64
<211> LENGTH: 18
<212> TYPE: RNA
<213> ORGANISM: Artificial Sequence
<220> FEATURE:
<223> OTHER INFORMATION: Synthetic: FO28 Nucleic acid sequence

<400> SEQUENCE: 64
ggcaugcgac cucuguuu                                                    18

<210> SEQ ID NO 65
<211> LENGTH: 14
<212> TYPE: RNA
<213> ORGANISM: Artificial Sequence
<220> FEATURE:
<223> OTHER INFORMATION: Synthetic: FO29 Nucleic acid sequence

<400> SEQUENCE: 65
ggcaugcgac cucu                                                        14

<210> SEQ ID NO 66
<211> LENGTH: 14
<212> TYPE: DNA
<213> ORGANISM: Artificial Sequence
<220> FEATURE:
<223> OTHER INFORMATION: Synthetic: FO30 Nucleic acid sequence

<400> SEQUENCE: 66
tgcucgaucg aucg                                                        14

<210> SEQ ID NO 67
<211> LENGTH: 14
<212> TYPE: DNA
<213> ORGANISM: Artificial Sequence
<220> FEATURE:
<223> OTHER INFORMATION: Synthetic: FO31 Nucleic acid sequence

<400> SEQUENCE: 67
tcgucgaucg aucg                                                        14

<210> SEQ ID NO 68
<211> LENGTH: 14
<212> TYPE: DNA
<213> ORGANISM: Artificial Sequence
<220> FEATURE:
<223> OTHER INFORMATION: Synthetic: SO1 Nucleic acid sequence

<400> SEQUENCE: 68
cgatcgatcg atcc                                                        14

<210> SEQ ID NO 69
<211> LENGTH: 14
<212> TYPE: RNA
<213> ORGANISM: Artificial Sequence
<220> FEATURE:
<223> OTHER INFORMATION: Synthetic: SO2 Nucleic acid sequence

<400> SEQUENCE: 69
auaucgaucg aucc                                                        14

<210> SEQ ID NO 70
```

```
<211> LENGTH: 14
<212> TYPE: RNA
<213> ORGANISM: Artificial Sequence
<220> FEATURE:
<223> OTHER INFORMATION: Synthetic: SO3 Nucleic acid sequence

<400> SEQUENCE: 70
gcgcgcgcgc gcgc                                              14

<210> SEQ ID NO 71
<211> LENGTH: 14
<212> TYPE: RNA
<213> ORGANISM: Artificial Sequence
<220> FEATURE:
<223> OTHER INFORMATION: Synthetic: SO4 Nucleic acid sequence

<400> SEQUENCE: 71
ggcggcgcgc cgcc                                              14

<210> SEQ ID NO 72
<211> LENGTH: 14
<212> TYPE: RNA
<213> ORGANISM: Artificial Sequence
<220> FEATURE:
<223> OTHER INFORMATION: Synthetic: SO5 Nucleic acid sequence

<400> SEQUENCE: 72
ccgccgccgc cgcc                                              14

<210> SEQ ID NO 73
<211> LENGTH: 14
<212> TYPE: RNA
<213> ORGANISM: Artificial Sequence
<220> FEATURE:
<223> OTHER INFORMATION: Synthetic: SO6 Nucleic acid sequence

<400> SEQUENCE: 73
cgcgggcggc cgcc                                              14

<210> SEQ ID NO 74
<211> LENGTH: 14
<212> TYPE: RNA
<213> ORGANISM: Artificial Sequence
<220> FEATURE:
<223> OTHER INFORMATION: Synthetic: SO7 Nucleic acid sequence

<400> SEQUENCE: 74
cgacgucgac gucg                                              14

<210> SEQ ID NO 75
<211> LENGTH: 14
<212> TYPE: RNA
<213> ORGANISM: Artificial Sequence
<220> FEATURE:
<223> OTHER INFORMATION: Synthetic: SO8 Nucleic acid sequence

<400> SEQUENCE: 75
gcacgucgac gugc                                              14

<210> SEQ ID NO 76
<211> LENGTH: 14
<212> TYPE: RNA
<213> ORGANISM: Artificial Sequence
<220> FEATURE:
<223> OTHER INFORMATION: Synthetic: SO9 Nucleic acid sequence

<400> SEQUENCE: 76
```
ggacgucgac gucc                                                    14

<210> SEQ ID NO 77
<211> LENGTH: 14
<212> TYPE: RNA
<213> ORGANISM: Artificial Sequence
<220> FEATURE:
<223> OTHER INFORMATION: Synthetic: SO10 Nucleic acid sequence

<400> SEQUENCE: 77
auauggucgc gacc                                                    14

<210> SEQ ID NO 78
<211> LENGTH: 14
<212> TYPE: RNA
<213> ORGANISM: Artificial Sequence
<220> FEATURE:
<223> OTHER INFORMATION: Synthetic: SO11 Nucleic acid sequence

<400> SEQUENCE: 78
acgucgacgu aucc                                                    14

<210> SEQ ID NO 79
<211> LENGTH: 14
<212> TYPE: RNA
<213> ORGANISM: Artificial Sequence
<220> FEATURE:
<223> OTHER INFORMATION: Synthetic: SO12 Nucleic acid sequence

<400> SEQUENCE: 79
ucucucucuc ucuc                                                    14

<210> SEQ ID NO 80
<211> LENGTH: 14
<212> TYPE: RNA
<213> ORGANISM: Artificial Sequence
<220> FEATURE:
<223> OTHER INFORMATION: Synthetic: SO13 Nucleic acid sequence

<400> SEQUENCE: 80
cggagucuag acuc                                                    14

<210> SEQ ID NO 81
<211> LENGTH: 14
<212> TYPE: RNA
<213> ORGANISM: Artificial Sequence
<220> FEATURE:
<223> OTHER INFORMATION: Synthetic: SO14 Nucleic acid sequence

<400> SEQUENCE: 81
cgaucgaucg aucg                                                    14

<210> SEQ ID NO 82
<211> LENGTH: 14
<212> TYPE: RNA
<213> ORGANISM: Artificial Sequence
<220> FEATURE:
<223> OTHER INFORMATION: Synthetic: SO15 Nucleic acid sequence

<400> SEQUENCE: 82
cgaucgaucg augg                                                    14

<210> SEQ ID NO 83
<211> LENGTH: 14
<212> TYPE: RNA

```
<213> ORGANISM: Artificial Sequence
<220> FEATURE:
<223> OTHER INFORMATION: Synthetic: SO16 Nucleic acid sequence

<400> SEQUENCE: 83
cgaucgaucg auuc                                                        14

<210> SEQ ID NO 84
<211> LENGTH: 11
<212> TYPE: RNA
<213> ORGANISM: Artificial Sequence
<220> FEATURE:
<223> OTHER INFORMATION: Synthetic: SO17 Nucleic acid sequence

<400> SEQUENCE: 84
cgaucgaucc c                                                           11

<210> SEQ ID NO 85
<211> LENGTH: 14
<212> TYPE: RNA
<213> ORGANISM: Artificial Sequence
<220> FEATURE:
<223> OTHER INFORMATION: Synthetic: SO18 Nucleic acid sequence

<400> SEQUENCE: 85
cgaucgaucg gggg                                                        14

<210> SEQ ID NO 86
<211> LENGTH: 14
<212> TYPE: RNA
<213> ORGANISM: Artificial Sequence
<220> FEATURE:
<223> OTHER INFORMATION: Synthetic: SO19 Nucleic acid sequence

<400> SEQUENCE: 86
acacacacac acac                                                        14

<210> SEQ ID NO 87
<211> LENGTH: 14
<212> TYPE: RNA
<213> ORGANISM: Artificial Sequence
<220> FEATURE:
<223> OTHER INFORMATION: Synthetic: SO20 Nucleic acid sequence

<400> SEQUENCE: 87
aucgauccac acac                                                        14

<210> SEQ ID NO 88
<211> LENGTH: 14
<212> TYPE: RNA
<213> ORGANISM: Artificial Sequence
<220> FEATURE:
<223> OTHER INFORMATION: Synthetic: SO21 Nucleic acid sequence
<220> FEATURE:
<221> NAME/KEY: misc_feature
<222> LOCATION: (4)..(4)
<223> OTHER INFORMATION: n is inosine
<220> FEATURE:
<221> NAME/KEY: misc_feature
<222> LOCATION: (8)..(8)
<223> OTHER INFORMATION: n is inosine
<220> FEATURE:
<221> NAME/KEY: misc_feature
<222> LOCATION: (12)..(12)
<223> OTHER INFORMATION: n is inosine

<400> SEQUENCE: 88
cgancgancg ancc                                                        14
```

```
<210> SEQ ID NO 89
<211> LENGTH: 14
<212> TYPE: RNA
<213> ORGANISM: Artificial Sequence
<220> FEATURE:
<223> OTHER INFORMATION: Synthetic: SO22 Nucleic acid sequence
<220> FEATURE:
<221> NAME/KEY: misc_feature
<222> LOCATION: (2)..(2)
<223> OTHER INFORMATION: n is inosine
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (10)..(10)
<223> OTHER INFORMATION: n is inosine

<400> SEQUENCE: 89
cnaucnaucn aucc                                                14

<210> SEQ ID NO 90
<211> LENGTH: 14
<212> TYPE: RNA
<213> ORGANISM: Artificial Sequence
<220> FEATURE:
<223> OTHER INFORMATION: Synthetic: SO23 Nucleic acid sequence
<220> FEATURE:
<221> NAME/KEY: misc_feature
<222> LOCATION: (3)..(3)
<223> OTHER INFORMATION: n is inosine
<220> FEATURE:
<221> NAME/KEY: misc_feature
<222> LOCATION: (7)..(7)
<223> OTHER INFORMATION: n is inosine
<220> FEATURE:
<221> NAME/KEY: misc_feature
<222> LOCATION: (11)..(11)
<223> OTHER INFORMATION: n is inosine

<400> SEQUENCE: 90
cgnucgnucg nucc                                                14

<210> SEQ ID NO 91
<211> LENGTH: 14
<212> TYPE: RNA
<213> ORGANISM: Artificial Sequence
<220> FEATURE:
<223> OTHER INFORMATION: Synthetic: SO24 Nucleic acid sequence

<400> SEQUENCE: 91
cgaucgaucg aucc                                                14

<210> SEQ ID NO 92
<211> LENGTH: 12
<212> TYPE: RNA
<213> ORGANISM: Artificial Sequence
<220> FEATURE:
<223> OTHER INFORMATION: Synthetic: SO25 Nucleic acid sequence

<400> SEQUENCE: 92
cgaucgaucg au                                                  12

<210> SEQ ID NO 93
<211> LENGTH: 18
<212> TYPE: RNA
<213> ORGANISM: Artificial Sequence
<220> FEATURE:
```

-continued

<223> OTHER INFORMATION: Synthetic: SO26 Nucleic acid sequence

<400> SEQUENCE: 93
aaacagaggu cgcaugcc                                                  18

<210> SEQ ID NO 94
<211> LENGTH: 14
<212> TYPE: RNA
<213> ORGANISM: Artificial Sequence
<220> FEATURE:
<223> OTHER INFORMATION: Synthetic: SO27 Nucleic acid sequence

<400> SEQUENCE: 94
agaggucgca ugcc                                                      14

<210> SEQ ID NO 95
<211> LENGTH: 14
<212> TYPE: RNA
<213> ORGANISM: Artificial Sequence
<220> FEATURE:
<223> OTHER INFORMATION: Synthetic: SO28 Nucleic acid sequence

<400> SEQUENCE: 95
cgaucgaucg agca                                                      14

<210> SEQ ID NO 96
<211> LENGTH: 14
<212> TYPE: RNA
<213> ORGANISM: Artificial Sequence
<220> FEATURE:
<223> OTHER INFORMATION: Synthetic: SO29 Nucleic acid sequence

<400> SEQUENCE: 96
cgaucgaucg acga                                                      14

<210> SEQ ID NO 97
<211> LENGTH: 14
<212> TYPE: DNA
<213> ORGANISM: Artificial Sequence
<220> FEATURE:
<223> OTHER INFORMATION: Synthetic: SO30 Nucleic acid sequence

<400> SEQUENCE: 97
tgaucgaucg augg                                                      14

<210> SEQ ID NO 98
<211> LENGTH: 925
<212> TYPE: PRT
<213> ORGANISM: Homo sapiens
<220> FEATURE:
<221> NAME/KEY: misc_feature
<223> OTHER INFORMATION: Human RIG-I Amino acid sequence

<400> SEQUENCE: 98

Met Thr Thr Glu Gln Arg Arg Ser Leu Gln Ala Phe Gln Asp Tyr Ile
1               5                   10                  15

Arg Lys Thr Leu Asp Pro Thr Tyr Ile Leu Ser Tyr Met Ala Pro Trp
            20                  25                  30

Phe Arg Glu Glu Glu Val Gln Tyr Ile Gln Ala Glu Lys Asn Asn Lys
        35                  40                  45

Gly Pro Met Glu Ala Ala Thr Leu Phe Leu Lys Phe Leu Leu Glu Leu
    50                  55                  60

Gln Glu Glu Gly Trp Phe Arg Gly Phe Leu Asp Ala Leu Asp His Ala
65                  70                  75                  80

```
Gly Tyr Ser Gly Leu Tyr Glu Ala Ile Glu Ser Trp Asp Phe Lys Lys
                85                  90                  95

Ile Glu Lys Leu Glu Glu Tyr Arg Leu Leu Lys Arg Leu Gln Pro
           100                 105                 110

Glu Phe Lys Thr Arg Ile Ile Pro Thr Asp Ile Ile Ser Asp Leu Ser
           115                 120                 125

Glu Cys Leu Ile Asn Gln Glu Cys Glu Glu Ile Leu Gln Ile Cys Ser
130                 135                 140

Thr Lys Gly Met Met Ala Gly Ala Glu Lys Leu Val Glu Cys Leu Leu
145                 150                 155                 160

Arg Ser Asp Lys Glu Asn Trp Pro Lys Thr Leu Lys Leu Ala Leu Glu
                165                 170                 175

Lys Glu Arg Asn Lys Phe Ser Glu Leu Trp Ile Val Glu Lys Gly Ile
           180                 185                 190

Lys Asp Val Glu Thr Glu Asp Leu Glu Asp Lys Met Glu Thr Ser Asp
           195                 200                 205

Ile Gln Ile Phe Tyr Gln Glu Asp Pro Glu Cys Gln Asn Leu Ser Glu
210                 215                 220

Asn Ser Cys Pro Pro Ser Glu Val Ser Asp Thr Asn Leu Tyr Ser Pro
225                 230                 235                 240

Phe Lys Pro Arg Asn Tyr Gln Leu Glu Leu Ala Leu Pro Ala Met Lys
                245                 250                 255

Gly Lys Asn Thr Ile Ile Cys Ala Pro Thr Gly Cys Gly Lys Thr Phe
           260                 265                 270

Val Ser Leu Leu Ile Cys Glu His His Leu Lys Lys Phe Pro Gln Gly
           275                 280                 285

Gln Lys Gly Lys Val Val Phe Phe Ala Asn Gln Ile Pro Val Tyr Glu
290                 295                 300

Gln Gln Lys Ser Val Phe Ser Lys Tyr Phe Glu Arg His Gly Tyr Arg
305                 310                 315                 320

Val Thr Gly Ile Ser Gly Ala Thr Ala Glu Asn Val Pro Val Glu Gln
                325                 330                 335

Ile Val Glu Asn Asn Asp Ile Ile Leu Thr Pro Gln Ile Leu Val
           340                 345                 350

Asn Asn Leu Lys Lys Gly Thr Ile Pro Ser Leu Ser Ile Phe Thr Leu
           355                 360                 365

Met Ile Phe Asp Glu Cys His Asn Thr Ser Lys Gln His Pro Tyr Asn
370                 375                 380

Met Ile Met Phe Asn Tyr Leu Asp Gln Lys Leu Gly Gly Ser Ser Gly
385                 390                 395                 400

Pro Leu Pro Gln Val Ile Gly Leu Thr Ala Ser Val Gly Val Gly Asp
                405                 410                 415

Ala Lys Asn Thr Asp Glu Ala Leu Asp Tyr Ile Cys Lys Leu Cys Ala
           420                 425                 430

Ser Leu Asp Ala Ser Val Ile Ala Thr Val Lys His Asn Leu Glu Glu
           435                 440                 445

Leu Glu Gln Val Val Tyr Lys Pro Gln Lys Phe Phe Arg Lys Val Glu
450                 455                 460

Ser Arg Ile Ser Asp Lys Phe Lys Tyr Ile Ile Ala Gln Leu Met Arg
465                 470                 475                 480

Asp Thr Glu Ser Leu Ala Lys Arg Ile Cys Lys Asp Leu Glu Asn Leu
                485                 490                 495
```

-continued

```
Ser Gln Ile Gln Asn Arg Glu Phe Gly Thr Gln Lys Tyr Glu Gln Trp
            500                 505                 510

Ile Val Thr Val Gln Lys Ala Cys Met Val Phe Gln Met Pro Asp Lys
            515                 520                 525

Asp Glu Glu Ser Arg Ile Cys Lys Ala Leu Phe Leu Tyr Thr Ser His
        530                 535                 540

Leu Arg Lys Tyr Asn Asp Ala Leu Ile Ile Ser Glu His Ala Arg Met
545                 550                 555                 560

Lys Asp Ala Leu Asp Tyr Leu Lys Asp Phe Ser Asn Val Arg Ala
                565                 570                 575

Ala Gly Phe Asp Glu Ile Glu Gln Asp Leu Thr Gln Arg Phe Glu Glu
            580                 585                 590

Lys Leu Gln Glu Leu Glu Ser Val Ser Arg Asp Pro Ser Asn Glu Asn
            595                 600                 605

Pro Lys Leu Glu Asp Leu Cys Phe Ile Leu Gln Glu Glu Tyr His Leu
        610                 615                 620

Asn Pro Glu Thr Ile Thr Ile Leu Phe Val Lys Thr Arg Ala Leu Val
625                 630                 635                 640

Asp Ala Leu Lys Asn Trp Ile Glu Gly Asn Pro Lys Leu Ser Phe Leu
                645                 650                 655

Lys Pro Gly Ile Leu Thr Gly Arg Gly Lys Thr Asn Gln Asn Thr Gly
            660                 665                 670

Met Thr Leu Pro Ala Gln Lys Cys Ile Leu Asp Ala Phe Lys Ala Ser
            675                 680                 685

Gly Asp His Asn Ile Leu Ile Ala Thr Ser Val Ala Asp Glu Gly Ile
690                 695                 700

Asp Ile Ala Gln Cys Asn Leu Val Ile Leu Tyr Glu Tyr Val Gly Asn
705                 710                 715                 720

Val Ile Lys Met Ile Gln Thr Arg Gly Arg Gly Arg Ala Arg Gly Ser
                725                 730                 735

Lys Cys Phe Leu Leu Thr Ser Asn Ala Gly Val Ile Glu Lys Glu Gln
            740                 745                 750

Ile Asn Met Tyr Lys Glu Lys Met Met Asn Asp Ser Ile Leu Arg Leu
            755                 760                 765

Gln Thr Trp Asp Glu Ala Val Phe Arg Glu Lys Ile Leu His Ile Gln
770                 775                 780

Thr His Glu Lys Phe Ile Arg Asp Ser Gln Glu Lys Pro Lys Pro Val
785                 790                 795                 800

Pro Asp Lys Glu Asn Lys Lys Leu Leu Cys Arg Lys Cys Lys Ala Leu
                805                 810                 815

Ala Cys Tyr Thr Ala Asp Val Arg Val Ile Glu Glu Cys His Tyr Thr
            820                 825                 830

Val Leu Gly Asp Ala Phe Lys Glu Cys Phe Val Ser Arg Pro His Pro
            835                 840                 845

Lys Pro Lys Gln Phe Ser Ser Phe Glu Lys Arg Ala Lys Ile Phe Cys
850                 855                 860

Ala Arg Gln Asn Cys Ser His Asp Trp Gly Ile His Val Lys Tyr Lys
865                 870                 875                 880

Thr Phe Glu Ile Pro Val Ile Lys Ile Glu Ser Phe Val Val Glu Asp
                885                 890                 895

Ile Ala Thr Gly Val Gln Thr Leu Tyr Ser Lys Trp Lys Asp Phe His
            900                 905                 910

Phe Glu Lys Ile Pro Phe Asp Pro Ala Glu Met Ser Lys
```

-continued

```
            915                 920                 925
```

<210> SEQ ID NO 99
<211> LENGTH: 1025
<212> TYPE: PRT
<213> ORGANISM: Homo sapiens
<220> FEATURE:
<221> NAME/KEY: misc_feature
<223> OTHER INFORMATION: Human MDA5 Amino acid sequence

<400> SEQUENCE: 99

```
Met Ser Asn Gly Tyr Ser Thr Asp Glu Asn Phe Arg Tyr Leu Ile Ser
1               5                   10                  15

Cys Phe Arg Ala Arg Val Lys Met Tyr Ile Gln Val Glu Pro Val Leu
            20                  25                  30

Asp Tyr Leu Thr Phe Leu Pro Ala Glu Val Lys Glu Gln Ile Gln Arg
        35                  40                  45

Thr Val Ala Thr Ser Gly Asn Met Gln Ala Val Glu Leu Leu Leu Ser
    50                  55                  60

Thr Leu Glu Lys Gly Val Trp His Leu Gly Trp Thr Arg Glu Phe Val
65                  70                  75                  80

Glu Ala Leu Arg Arg Thr Gly Ser Pro Leu Ala Ala Arg Tyr Met Asn
                85                  90                  95

Pro Glu Leu Thr Asp Leu Pro Ser Pro Ser Phe Glu Asn Ala His Asp
            100                 105                 110

Glu Tyr Leu Gln Leu Leu Asn Leu Leu Gln Pro Thr Leu Val Asp Lys
        115                 120                 125

Leu Leu Val Arg Asp Val Leu Asp Lys Cys Met Glu Glu Glu Leu Leu
    130                 135                 140

Thr Ile Glu Asp Arg Asn Arg Ile Ala Ala Glu Asn Asn Gly Asn
145                 150                 155                 160

Glu Ser Gly Val Arg Glu Leu Leu Lys Arg Ile Val Gln Lys Glu Asn
                165                 170                 175

Trp Phe Ser Ala Phe Leu Asn Val Leu Arg Gln Thr Gly Asn Asn Glu
            180                 185                 190

Leu Val Gln Glu Leu Thr Gly Ser Asp Cys Ser Glu Ser Asn Ala Glu
        195                 200                 205

Ile Glu Asn Leu Ser Gln Val Asp Gly Pro Gln Val Glu Glu Gln Leu
    210                 215                 220

Leu Ser Thr Thr Val Gln Pro Asn Leu Glu Lys Glu Val Trp Gly Met
225                 230                 235                 240

Glu Asn Asn Ser Ser Glu Ser Ser Phe Ala Asp Ser Ser Val Val Ser
                245                 250                 255

Glu Ser Asp Thr Ser Leu Ala Glu Gly Ser Val Ser Cys Leu Asp Glu
            260                 265                 270

Ser Leu Gly His Asn Ser Asn Met Gly Ser Asp Ser Gly Thr Met Gly
        275                 280                 285

Ser Asp Ser Asp Glu Glu Asn Val Ala Ala Arg Ala Ser Pro Glu Pro
    290                 295                 300

Glu Leu Gln Leu Arg Pro Tyr Gln Met Glu Val Ala Gln Pro Ala Leu
305                 310                 315                 320

Glu Gly Lys Asn Ile Ile Ile Cys Leu Pro Thr Gly Ser Gly Lys Thr
                325                 330                 335

Arg Val Ala Val Tyr Ile Ala Lys Asp His Leu Asp Lys Lys Lys
            340                 345                 350
```

```
Ala Ser Glu Pro Gly Lys Val Ile Val Leu Val Asn Lys Val Leu Leu
        355                 360                 365
Val Glu Gln Leu Phe Arg Lys Glu Phe Gln Pro Phe Leu Lys Lys Trp
370                 375                 380
Tyr Arg Val Ile Gly Leu Ser Gly Asp Thr Gln Leu Lys Ile Ser Phe
385                 390                 395                 400
Pro Glu Val Val Lys Ser Cys Asp Ile Ile Ser Thr Ala Gln Ile
                405                 410                 415
Leu Glu Asn Ser Leu Leu Asn Leu Glu Asn Gly Glu Asp Ala Gly Val
            420                 425                 430
Gln Leu Ser Asp Phe Ser Leu Ile Ile Ile Asp Glu Cys His His Thr
        435                 440                 445
Asn Lys Glu Ala Val Tyr Asn Asn Ile Met Arg His Tyr Leu Met Gln
    450                 455                 460
Lys Leu Lys Asn Asn Arg Leu Lys Lys Glu Asn Lys Pro Val Ile Pro
465                 470                 475                 480
Leu Pro Gln Ile Leu Gly Leu Thr Ala Ser Pro Gly Val Gly Gly Ala
                485                 490                 495
Thr Lys Gln Ala Lys Ala Glu His Ile Leu Lys Leu Cys Ala Asn
                500                 505                 510
Leu Asp Ala Phe Thr Ile Lys Thr Val Lys Glu Asn Leu Asp Gln Leu
        515                 520                 525
Lys Asn Gln Ile Gln Glu Pro Cys Lys Lys Phe Ala Ile Ala Asp Ala
    530                 535                 540
Thr Arg Glu Asp Pro Phe Lys Glu Lys Leu Leu Glu Ile Met Thr Arg
545                 550                 555                 560
Ile Gln Thr Tyr Cys Gln Met Ser Pro Met Ser Asp Phe Gly Thr Gln
                565                 570                 575
Pro Tyr Glu Gln Trp Ala Ile Gln Met Glu Lys Lys Ala Ala Lys Glu
                580                 585                 590
Gly Asn Arg Lys Glu Arg Val Cys Ala Glu His Leu Arg Lys Tyr Asn
            595                 600                 605
Glu Ala Leu Gln Ile Asn Asp Thr Ile Arg Met Ile Asp Ala Tyr Thr
        610                 615                 620
His Leu Glu Thr Phe Tyr Asn Glu Glu Lys Asp Lys Lys Phe Ala Val
625                 630                 635                 640
Ile Glu Asp Asp Ser Asp Glu Gly Gly Asp Asp Glu Tyr Cys Asp Gly
                645                 650                 655
Asp Glu Asp Glu Asp Asp Leu Lys Lys Pro Leu Lys Leu Asp Glu Thr
            660                 665                 670
Asp Arg Phe Leu Met Thr Leu Phe Phe Glu Asn Asn Lys Met Leu Lys
        675                 680                 685
Arg Leu Ala Glu Asn Pro Glu Tyr Glu Asn Glu Lys Leu Thr Lys Leu
    690                 695                 700
Arg Asn Thr Ile Met Glu Gln Tyr Thr Arg Thr Glu Glu Ser Ala Arg
705                 710                 715                 720
Gly Ile Ile Phe Thr Lys Thr Arg Gln Ser Ala Tyr Ala Leu Ser Gln
                725                 730                 735
Trp Ile Thr Glu Asn Glu Lys Phe Ala Glu Val Gly Val Lys Ala His
                740                 745                 750
His Leu Ile Gly Ala Gly His Ser Ser Glu Phe Lys Pro Met Thr Gln
            755                 760                 765
Asn Glu Gln Lys Glu Val Ile Ser Lys Phe Arg Thr Gly Lys Ile Asn
```

```
                     770             775             780
Leu Leu Ile Ala Thr Thr Val Ala Glu Glu Gly Leu Asp Ile Lys Glu
785                 790             795                 800

Cys Asn Ile Val Ile Arg Tyr Gly Leu Val Thr Asn Glu Ile Ala Met
                805             810                 815

Val Gln Ala Arg Gly Arg Ala Arg Ala Asp Glu Ser Thr Tyr Val Leu
                820             825                 830

Val Ala His Ser Gly Ser Gly Val Ile Glu His Glu Thr Val Asn Asp
            835             840                 845

Phe Arg Glu Lys Met Met Tyr Lys Ala Ile His Cys Val Gln Asn Met
850                 855             860

Lys Pro Glu Glu Tyr Ala His Lys Ile Leu Glu Leu Gln Met Gln Ser
865                 870             875                 880

Ile Met Glu Lys Lys Met Lys Thr Lys Arg Asn Ile Ala Lys His Tyr
                885             890                 895

Lys Asn Asn Pro Ser Leu Ile Thr Phe Leu Cys Lys Asn Cys Ser Val
                900             905                 910

Leu Ala Cys Ser Gly Glu Asp Ile His Val Ile Glu Lys Met His His
                915             920             925

Val Asn Met Thr Pro Glu Phe Lys Glu Leu Tyr Ile Val Arg Glu Asn
930                 935             940

Lys Ala Leu Gln Lys Lys Cys Ala Asp Tyr Gln Ile Asn Gly Glu Ile
945                 950             955                 960

Ile Cys Lys Cys Gly Gln Ala Trp Gly Thr Met Met Val His Lys Gly
                965             970                 975

Leu Asp Leu Pro Cys Leu Lys Ile Arg Asn Phe Val Val Val Phe Lys
                980             985                 990

Asn Asn Ser Thr Lys Lys Gln Tyr  Lys Lys Trp Val Glu  Leu Pro Ile
                995              1000              1005

Thr Phe  Pro Asn Leu Asp Tyr  Ser Glu Cys Cys Leu  Phe Ser Asp
     1010             1015              1020

Glu Asp
     1025

<210> SEQ ID NO 100
<211> LENGTH: 678
<212> TYPE: PRT
<213> ORGANISM: Homo sapiens
<220> FEATURE:
<221> NAME/KEY: misc_feature
<223> OTHER INFORMATION: Human LGP2 Amino acid sequence

<400> SEQUENCE: 100

Met Glu Leu Arg Ser Tyr Gln Trp Glu Val Ile Met Pro Ala Leu Glu
1               5                   10                  15

Gly Lys Asn Ile Ile Ile Trp Leu Pro Thr Gly Ala Gly Lys Thr Arg
                20                  25                  30

Ala Ala Ala Tyr Val Ala Lys Arg His Leu Glu Thr Val Asp Gly Ala
            35                  40                  45

Lys Val Val Val Leu Val Asn Arg Val His Leu Val Thr Gln His Gly
        50                  55                  60

Glu Glu Phe Arg Arg Met Leu Asp Gly Arg Trp Thr Val Thr Thr Leu
65                  70                  75                  80

Ser Gly Asp Met Gly Pro Arg Ala Gly Phe Gly His Leu Ala Arg Cys
                85                  90                  95
```

-continued

```
His Asp Leu Leu Ile Cys Thr Ala Glu Leu Leu Gln Met Ala Leu Thr
            100                 105                 110

Ser Pro Glu Glu Glu His Val Glu Leu Thr Val Phe Ser Leu Ile
        115                 120                 125

Val Val Asp Glu Cys His His Thr His Lys Asp Thr Val Tyr Asn Val
130                 135                 140

Ile Met Ser Gln Tyr Leu Glu Leu Lys Leu Gln Arg Ala Gln Pro Leu
145                 150                 155                 160

Pro Gln Val Leu Gly Leu Thr Ala Ser Pro Gly Thr Gly Gly Ala Ser
                165                 170                 175

Lys Leu Asp Gly Ala Ile Asn His Val Leu Gln Leu Cys Ala Asn Leu
            180                 185                 190

Asp Thr Trp Cys Ile Met Ser Pro Gln Asn Cys Cys Pro Gln Leu Gln
        195                 200                 205

Glu His Ser Gln Gln Pro Cys Lys Gln Tyr Asn Leu Cys His Arg Arg
210                 215                 220

Ser Gln Asp Pro Phe Gly Asp Leu Leu Lys Lys Leu Met Asp Gln Ile
225                 230                 235                 240

His Asp His Leu Glu Met Pro Glu Leu Ser Arg Lys Phe Gly Thr Gln
                245                 250                 255

Met Tyr Glu Gln Gln Val Val Lys Leu Ser Glu Ala Ala Leu Ala
            260                 265                 270

Gly Leu Gln Glu Gln Arg Val Tyr Ala Leu His Leu Arg Arg Tyr Asn
        275                 280                 285

Asp Ala Leu Leu Ile His Asp Thr Val Arg Ala Val Asp Ala Leu Ala
290                 295                 300

Ala Leu Gln Asp Phe Tyr His Arg Glu His Val Thr Lys Thr Gln Ile
305                 310                 315                 320

Leu Cys Ala Glu Arg Arg Leu Leu Ala Leu Phe Asp Asp Arg Lys Asn
                325                 330                 335

Glu Leu Ala His Leu Ala Thr His Gly Pro Glu Asn Pro Lys Leu Glu
            340                 345                 350

Met Leu Glu Lys Ile Leu Gln Arg Gln Phe Ser Ser Ser Asn Ser Pro
        355                 360                 365

Arg Gly Ile Ile Phe Thr Arg Thr Arg Gln Ser Ala His Ser Leu Leu
370                 375                 380

Leu Trp Leu Gln Gln Gln Gly Leu Gln Thr Val Asp Ile Arg Ala
385                 390                 395                 400

Gln Leu Leu Ile Gly Ala Gly Asn Ser Ser Gln Ser Thr His Met Thr
                405                 410                 415

Gln Arg Asp Gln Gln Glu Val Ile Gln Lys Phe Gln Asp Gly Thr Leu
            420                 425                 430

Asn Leu Leu Val Ala Thr Ser Val Ala Glu Glu Gly Leu Asp Ile Pro
        435                 440                 445

His Cys Asn Val Val Arg Tyr Gly Leu Leu Thr Asn Glu Ile Ser
450                 455                 460

Met Val Gln Ala Arg Gly Arg Ala Arg Ala Asp Gln Ser Val Tyr Ala
465                 470                 475                 480

Phe Val Ala Thr Glu Gly Ser Arg Glu Leu Lys Arg Glu Leu Ile Asn
                485                 490                 495

Glu Ala Leu Glu Thr Leu Met Glu Gln Ala Val Ala Ala Val Gln Lys
            500                 505                 510

Met Asp Gln Ala Glu Tyr Gln Ala Lys Ile Arg Asp Leu Gln Gln Ala
```

-continued

```
                515                 520                 525
Ala Leu Thr Lys Arg Ala Ala Gln Ala Ala Gln Arg Glu Asn Gln Arg
            530                 535                 540

Gln Gln Phe Pro Val Glu His Val Gln Leu Leu Cys Ile Asn Cys Met
545                 550                 555                 560

Val Ala Val Gly His Gly Ser Asp Leu Arg Lys Val Glu Gly Thr His
                565                 570                 575

His Val Asn Val Asn Pro Asn Phe Ser Asn Tyr Tyr Asn Val Ser Arg
            580                 585                 590

Asp Pro Val Val Ile Asn Lys Val Phe Lys Asp Trp Lys Pro Gly Gly
            595                 600                 605

Val Ile Ser Cys Arg Asn Cys Gly Glu Val Trp Gly Leu Gln Met Ile
            610                 615                 620

Tyr Lys Ser Val Lys Leu Pro Val Leu Lys Val Arg Ser Met Leu Leu
625                 630                 635                 640

Glu Thr Pro Gln Gly Arg Ile Gln Ala Lys Lys Trp Ser Arg Val Pro
                645                 650                 655

Phe Ser Val Pro Asp Phe Asp Phe Leu Gln His Cys Ala Glu Asn Leu
                660                 665                 670

Ser Asp Leu Ser Leu Asp
            675
```